US007816526B2

(12) United States Patent
Tanaka et al.

(10) Patent No.: US 7,816,526 B2
(45) Date of Patent: Oct. 19, 2010

(54) CONDENSED HETEROCYCLIC SULFONYL UREA COMPOUND, A HERBICIDE CONTAINING THE SAME, AND A METHOD FOR WEED CONTROL USING THE SAME

(75) Inventors: Yasushi Tanaka, Tsukuba (JP); Yukari Kajiwara, Niiharigun (JP); Makoto Noguchi, Suita (JP); Takeshi Kajiwara, Niiharigun (JP); Takanori Tabuchi, Tsukuba (JP)

(73) Assignee: Sumitomo Chemical Company, Limited, Tokyo (JP)

( * ) Notice: Subject to any disclaimer, the term of this patent is extended or adjusted under 35 U.S.C. 154(b) by 0 days.

(21) Appl. No.: 10/498,805

(22) PCT Filed: Jan. 15, 2003

(86) PCT No.: PCT/JP03/00244

§ 371 (c)(1),
(2), (4) Date: Jun. 15, 2004

(87) PCT Pub. No.: WO03/061388

PCT Pub. Date: Jul. 31, 2003

(65) Prior Publication Data

US 2005/0032650 A1 Feb. 10, 2005

(30) Foreign Application Priority Data

Jan. 18, 2002 (JP) ............................. 2002-010246
Jul. 29, 2002 (JP) ............................. 2002-219786

(51) Int. Cl.
C07D 487/00 (2006.01)
C07D 403/00 (2006.01)
C07D 239/02 (2006.01)
A01N 47/36 (2006.01)
A01N 43/54 (2006.01)

(52) U.S. Cl. ................... 544/279; 544/235; 544/236; 544/296; 544/320; 504/215

(58) Field of Classification Search ................ 544/332, 544/331, 281, 295, 321, 279, 296, 235, 236, 544/320; 504/211, 213, 215; 514/342, 374
See application file for complete search history.

(56) References Cited

U.S. PATENT DOCUMENTS

| | | | | | |
|---|---|---|---|---|---|
| 4,678,499 | A | * | 7/1987 | Pasteris et al. ............... | 504/214 |
| 4,921,527 | A | * | 5/1990 | Tseng ........................ | 504/211 |
| 4,994,571 | A | * | 2/1991 | Miki et al. .................. | 544/331 |
| 5,017,212 | A | * | 5/1991 | Ishida et al. ................ | 504/213 |
| 5,723,479 | A | * | 3/1998 | Sohda et al. ................ | 514/369 |
| 5,932,601 | A | * | 8/1999 | Sohda et al. ................ | 514/376 |
| 5,965,584 | A | * | 10/1999 | Ikeda et al. ................ | 514/342 |
| 5,965,589 | A | * | 10/1999 | Sohda et al. ................ | 514/369 |
| 6,150,383 | A | * | 11/2000 | Ikeda et al. ................ | 514/342 |
| 6,177,452 | B1 | * | 1/2001 | Momose et al. ............. | 514/377 |
| 6,498,179 | B1 | * | 12/2002 | Momose et al. ............. | 514/377 |
| 6,552,058 | B1 | * | 4/2003 | Sohda et al. ................ | 514/376 |
| 6,689,745 | B1 | * | 2/2004 | Itakura et al. ............... | 514/2 |
| 6,777,435 | B1 | * | 8/2004 | Momose et al. ............. | 514/374 |

FOREIGN PATENT DOCUMENTS

| | | |
|---|---|---|
| EP | 238070 | 9/1987 |
| JP | 64-038091 | 2/1989 |
| JP | 01-139582 | 6/1989 |
| JP | 01-316379 | 12/1989 |
| WO | 98/46079 | 10/1998 |

OTHER PUBLICATIONS

Yoshikawa et al, (AN 115:201124, MARPAT, abstract of JP 03072408).*
Yoshikawa et al, (DN 112:114195, CAPLUS, abstract of JP 01207211).*
Yoshikawa et al, !AN 113:128082, MARPAT, abstract of JP 02009805).*
Japanese Office Action (with English translation) dated Dec. 8, 2009 in counterpart Japanese Patent Application No. 2004-524110.
Experimental Chemistry Course Organic Synthesis I-Hydrocarbon Halogen Compound-, $2^{nd}$ edition, Maruzen Company, Limited, pp. 104-110 (1992).
Tamao, et al. "Selective Carbon-Carbon Bond Formation by Cross-Coupling of Grignard Reagents with Organic Halides. Catalysis by Nickel-Phosphine Complexes," Journal of the American Chemical Society, vol. 94, No. 12, pp. 4374-4376 (1972).

(Continued)

Primary Examiner—Sabiha Qazi
(74) Attorney, Agent, or Firm—Wenderoth, Lind & Ponack L.L.P.

(57) ABSTRACT

The present invention provides a compound represented by the formula:

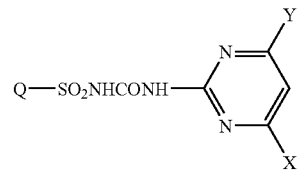

wherein Q represents a fused heterocyclic group, X and Y are the same or different and each represent an optionally halogenated lower alkyl group, an optionally halogenated lower alkoxy group, etc., or a salt thereof, as well as a herbicide comprising the compound or a salt thereof, which exhibits a significant effect for control of sulfonylurea herbicide-resistant weeds in paddy fields and can reduce the number of active ingredients in a combined preparation and a method of controlling sulfonylurea herbicide-resistant weeds which comprises using the same.

2 Claims, No Drawings

OTHER PUBLICATIONS

Japanese Office Action (with English translation) dated Dec. 8, 2009 in counterpart Japanese Patent Application No. 2004-524110.

Experimental Chemistry Course Organic Synthesis I-Hydrocarbon Halogen Compound-, $2^{nd}$ edition, Maruzen Company, Limited, pp. 104-110 (1992).

Tamao, et al. "Selective Carbon-Carbon Bond Formation by Cross-Coupling of Grignard Reagents with Organic Halides. Catalysis by Nickel-Phosphine Complexes," Journal of the American Chemical Society, vol. 94, No. 12, pp. 4374-4376 (1972).

* cited by examiner

CONDENSED HETEROCYCLIC SULFONYL UREA COMPOUND, A HERBICIDE CONTAINING THE SAME, AND A METHOD FOR WEED CONTROL USING THE SAME

This application is a U.S. national stage of International Application No. PCT/JP03/00244 filed Jan. 15, 2003.

TECHNICAL FIELD

This invention relates to a novel herbicide containing a fused heterocyclic sulfonylurea compound, a method for controlling weeds in paddy fields, and a novel fused heterocyclic sulfonylurea compound. This invention relates in particular to a herbicide which upon application to paddy-rice plants during or after planting, has extremely excellent selectivity for paddy-rice plants and exhibits a strong weeding effect on weeds resistant to sulfonylurea herbicides, a method of controlling sulfonylurea herbicide-resistant weeds by using the same, and a novel fused heterocyclic sulfonylurea compound.

BACKGROUND ART

Up to now, a large number of sulfonylurea compounds for paddy fields have been in practical use, and used widely and generally as a combined preparation comprising two or more active ingredients with various kinds of Gramineae weed killers effective against weeds of the Gramineae family, but in recent years, there appear weeds resistant to sulfonylurea herbicides such as bensulfuron-methyl, pyrazosulfuron-ethyl and imazosulfuron, and their control becomes problematic.

It is known that weeds resistant to sulfonylurea herbicides are generally cross-resistant to acetolactate synthase (ALS) inhibitors including sulfonylurea herbicides acting on ALS. However, conventional methods for controlling weeds are those methods of adding active ingredients effective against sulfonylurea herbicide-resistant weeds to an existing combined preparation thereby increasing the number of active ingredients in the combined preparation to control the weeds (for example, JP-A 10-287513, JP-A 11-228307 and JP-A 11-349411). Under these circumstances, there is demand for herbicides having a satisfactory effect on weeds resistant to sulfonylurea herbicides and capable of decreasing the number of active ingredients in a combined preparation.

PURPOSE OF THE INVENTION

An object of this invention is to develop a herbicide which has an excellent weeding effect on weeds resistant to sulfonylurea herbicides without exerting herbicide injury to paddy-rice plants and which can reduce the number of active ingredients in a combined preparation. Another object of this invention is to develop a herbicide which has an excellent weeding effect not only on weeds resistant to sulfonylurea herbicides but also on annual broadleaf weeds and perennial weeds other than the resistant weeds and which has a broad weeding spectrum without exerting any herbicide injury to paddy-rice plants.

SUMMARY OF INVENTION

To develop excellent herbicides having a broad weeding spectrum and free of herbicide injury, the present inventors made extensive study, and as a result, found that the compounds represented by the following formula (I) or salts thereof, though falling under the scope of fused heterocyclic sulfonylurea compounds in JP-A 64-38091 filed by the present applicant, have a higher weeding effect on a broader range of sulfonylurea herbicide-resistant weeds than most other herbicides, and this invention was thereby completed.

It was surprisingly revealed that in those compounds of formula (I) below wherein the substituent group Q is a group represented by Q1 to Q3, the compounds wherein R3 is a hydrogen, exhibit a high weeding effect on weeds sensitive to sulfonylurea herbicides, but significantly reduce their effect on weeds resistant to said herbicides, whereas those compounds wherein R3 represents any one of the substituent groups below and Q is a group represented by Q4 have their high weeding effect not only on weeds sensitive to sulfonylurea herbicides but also on weeds resistant to said herbicides.

That is, this invention provides:

(1) a herbicide for sulfonylurea herbicide-resistant weeds, comprising a compound (also referred to as hereinafter as Compound (I)) represented by the formula:

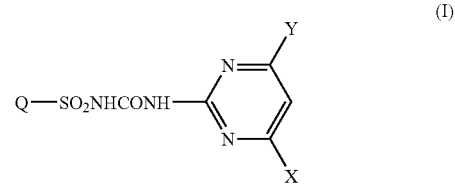

wherein Q represents a fused heterocyclic group represented by the formulae:

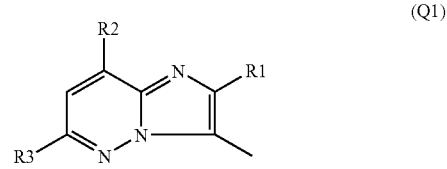

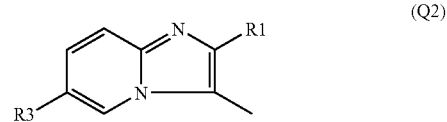

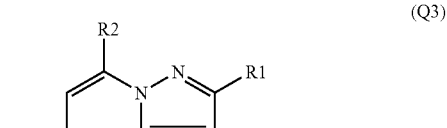

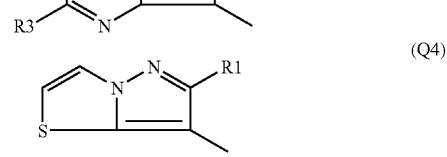

wherein R1 represents a hydrogen atom, a halogen atom, a cyano group, a nitro group, an optionally halogenated lower alkyl group, an optionally halogenated lower alkoxy group, a lower alkylthio group, a lower alkylsulfinyl group, a lower alkylsulfonyl group, an amino group, a lower alkylamino group or a di-lower alkylamino group, R2 represents a hydrogen atom, a halogen atom or an optionally halogenated lower alkyl group, R3 represents a halogen atom, a cyano group, a nitro group, an optionally halogenated lower alkyl group, an optionally halogenated or lower-alkylated lower cycloalkyl group, an optionally halogenated lower alkenyl group, an optionally halogenated lower alkynyl group, an optionally halogenated lower alkoxy group, a lower alkylthio group, a lower alkylsulfinyl group, a lower alkylsulfonyl group, an amino group, a lower alkylamino group or a di-lower alkylamino group, X and Y are the same or different and each represent an optionally halogenated lower alkyl group, an optionally halogenated lower alkoxy group or a halogen atom, or a salt thereof;

(2) the herbicide according to the above-mentioned (1), wherein R1 represents a halogen atom, an optionally halogenated lower alkyl group, a lower alkylthio group, a lower alkylsulfinyl group or a lower alkylsulfonyl group, R3 represents a halogen atom, an optionally halogenated lower alkyl group, an optionally halogenated or lower-alkylated lower cycloalkyl group, an optionally halogenated lower alkoxy group, a lower alkylthio group, a lower alkylsulfinyl group, a lower alkylsulfonyl group, a lower alkylamino group or a di-lower alkylamino group, and X and Y each represent an optionally halogenated lower alkoxy group;

(3) The herbicide according to the above-mentioned (1), wherein R1 represents a halogen atom or an optionally halogenated lower alkyl group, R2 represents a hydrogen atom, R3 represents a halogen atom, an optionally halogenated lower alkyl group, an optionally halogenated or lower-alkylated lower cycloalkyl group, an optionally halogenated lower alkoxy group, a lower alkylthio group, a lower alkylsulfinyl group, a lower alkylsulfonyl group, a lower alkylamino group or a di-lower alkylamino group, and X and Y each represent an optionally halogenated lower alkyl group or an optionally halogenated lower alkoxy group;

(4) the herbicide according to the above-mentioned (1), wherein Q is a fused heterocyclic group represented by the formula Q1 or Q4 above;

(5) a compound represented by the formula:

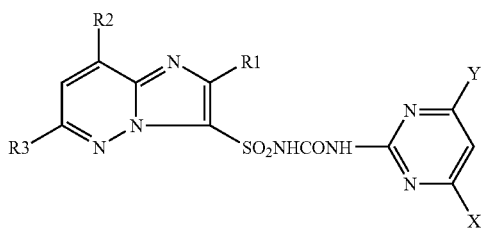

wherein R1 represents a halogen atom or an optionally halogenated lower alkyl group, R2 represents a hydrogen atom, R3 represents an optionally halogenated $C_{2-4}$ alkyl group or an optionally halogenated or lower-alkylated lower cycloalkyl group, and X and Y each represent an optionally halogenated lower alkyl group or an optionally halogenated lower alkoxy group, or a salt thereof (also referred to hereinafter as Compound (Ia));

(6) the compound according to the above-mentioned (5), wherein R1 is a halogen atom, R3 is a $C_{2-4}$ alkyl group or a lower cycloalkyl group, and each of X and Y is a methoxy group, or a salt thereof;

(7) a herbicide for sulfonylurea herbicide-resistant weeds, comprising the compound described in the above-mentioned (5) or a salt thereof;

(8) a herbicide for sulfonylurea herbicide-resistant weeds, comprising the compound described in the above-mentioned (6) or a salt thereof;

(9) the herbicide according to any one of the above-mentioned (1) to (4), (7) and (8), which exhibits a significant effect on sulfonylurea herbicide-resistant weeds;

(10) a method for controlling sulfonylurea herbicide-resistant weeds, which comprises applying the herbicide described in any one of the above-mentioned (1) to (4), (7) and (8); and

(11) a method for controlling weeds in paddy fields, which comprises applying the herbicide described in any one of the above-mentioned (1) to (4), (7) and (8); and the like.

DETAILED DESCRIPTION OF THE INVENTION

Given the term "lower" in the lower alkyl group, lower alkenyl group, lower alkoxy group, lower alkylthio group etc. in this specification, the hydrocarbon moiety is meant to be composed of 1 or 2 to 6 carbon atoms, preferably 1 or 2 to 4 carbon atoms. The hydrocarbon moiety includes, for example, a linear or branched $C_{1-6}$ alkyl group, $C_{2-6}$ alkenyl group, $C_{1-6}$ alkoxy group, $C_{1-6}$ alkylthio group, etc.

In the fused heterocyclic group represented by Q in Compound (I), R1 represents a hydrogen atom, a halogen atom, a cyano group, a nitro group, an optionally halogenated lower alkyl group, an optionally halogenated lower alkoxy group, a lower alkylthio group, a lower alkylsulfinyl group, a lower alkylsulfonyl group, an amino group, a lower alkylamino group or a di-lower alkylamino group.

The "halogen atom" represented by R1 includes, for example, fluorine, chlorine, bromine, iodine etc.

The "lower alkyl group" represented by R1 includes, for example, a linear or branched $C_{1-4}$ alkyl group such as methyl, ethyl, n-propyl, isopropyl, n-butyl, isobutyl, sec-butyl, t-butyl etc. The "halogen" in the "optionally halogenated lower alkyl group" includes, for example, fluorine, chlorine, bromine, iodine etc., and the lower alkyl group may be substituted with 1 or more, preferably 1 to 3 halogens, at substitutable positions.

The "lower alkoxy group" represented by R1 includes a linear or branched $C_{1-4}$ alkoxy group such as methoxy, ethoxy, propoxy, isopropoxy, t-butoxy etc. The "halogen" in the "optionally halogenated lower alkoxy group" includes the same halogen as in the lower alkyl group described above, and the lower alkoxy group may be substituted with 1 or more, preferably 1 to 3 halogens, at substitutable positions.

The "lower alkyl" in the "lower alkylthio group", "lower alkylsulfinyl group", "lower alkylsulfonyl group", "lower alkylamino group" and "di-lower alkylamino group" represented by R1 includes the same group as the "lower alkyl group" described above.

R2 represents a hydrogen atom, a halogen atom or an optionally halogenated lower alkyl group, and the "halogen atom", "halogen" and "lower alkyl group" are exemplified by those represented by R1 described above, and the lower alkyl group may be substituted with 1 or more, preferably 1 to 3 halogens, at substitutable positions.

R3 represents a halogen atom, a cyano group, a nitro group, an optionally halogenated lower alkyl group, an optionally halogenated or lower-alkylated lower cycloalkyl group, an optionally halogenated lower alkenyl group, an optionally halogenated lower alkynyl group, an optionally halogenated lower alkoxy group, a lower alkylthio group, a lower alkylsulfinyl group, a lower alkylsulfonyl group, an amino group, a lower alkylamino group or a di-lower alkylamino group.

The "halogen atom", "halogen", "lower alkyl group" and "lower alkoxy group" are exemplified by those represented by R1 described above. The lower alkyl group and lower alkoxy group may be substituted with 1 or more, preferably 1 to 3 halogens, at substitutable positions. The "lower cycloalkyl group" includes cyclopropyl, cyclobutyl etc., and the "lower alkenyl group" includes ethenyl, 1-propenyl, 2-propenyl, 1,2-propadienyl, 1-butenyl, 2-butenyl, 3-butenyl, 1,3-butadienyl etc., and the "lower alkynyl" includes ethynyl, 1-propynyl, 2-propynyl, 1-butynyl, 2-butynyl etc. In the "lower alkylthio group", "lower alkylsulfinyl group", "lower alkylsulfonyl group", "lower alkylamino group" and "di-lower alkylamino group", the "lower alkyl group" is exemplified by the "lower alkyl group" in R1 described above.

As the fused heterocyclic group represented by Q, an imidazo[1,2-b]pyridazine group represented by formula Q1, a pyrazolo[1,5-a]pyrimidine group represented by formula Q3 and a pyrazolo[1,5-b]thiazole group represented by formula Q4 are preferred because of their high activity against sulfonylurea herbicide-resistant weeds. The group represented by formula Q1 is particularly preferred.

In Compound (I), X and Y are the same or different and each represent an optionally halogenated lower alkyl group, an optionally halogenated lower alkoxy group or a halogen atom. The "halogen", "lower alkyl group", "lower alkoxy group" and "halogen atom" are exemplified by those represented by R1 described above. The lower alkyl group or lower alkoxy group may be substituted with 1 or more, preferably 1 to 3 halogens, at substitutable positions. As X and Y, an optionally halogenated lower alkoxy group is preferred, and methoxy group is more preferred.

As Compound (I), preferred is a compound wherein Q represents Q1 and (a) R1 represents a halogen atom or an optionally halogenated lower alkyl group, R2 represents a hydrogen atom, a halogen atom or an optionally halogenated lower alkyl group, R3 represents a halogen atom, an optionally halogenated lower alkyl group, an optionally halogenated or lower-alkylated lower cycloalkyl group, an optionally halogenated lower alkoxy group, a lower alkylthio group, a lower alkylsulfinyl group, a lower alkylsulfonyl group, a lower alkylamino group or a di-lower alkylamino group and X and Y each represent an optionally halogenated lower alkyl group or an optionally halogenated lower alkoxy group; more preferred is a compound wherein Q represents Q1 and (b) R1 represents a halogen atom or an optionally halogenated lower alkyl group, R2 represents a hydrogen atom, R3 represents a halogen atom, an optionally halogenated lower alkyl group, an optionally halogenated or lower-alkylated lower cycloalkyl group, an optionally halogenated lower alkoxy group, a lower alkylthio group, a lower alkylsulfinyl group, a lower alkylsulfonyl group, a lower alkylamino group or a di-lower alkylamino group, and X and Y each represent an optionally halogenated lower alkoxy group; and particularly preferred is a compound wherein Q represents Q1 and (C) R1 represents a halogen atom, R2 represents a hydrogen atom, R3 represents a $C_{2-4}$ alkyl group or a lower cycloalkyl group, and X and Y each represent a methoxy group, such as Compound (Ia).

Typical examples of Compound (I) include:
(1) Compound (I) wherein Q is Q1, R1 is ethyl, R2 is a hydrogen atom, R3 is methylthio, and each of X and Y is methoxy,
(2) Compound (I) wherein Q is Q1, R1 is methyl, R2 is a hydrogen atom, R3 is ethyl, and each of X and Y is methoxy,
(3) Compound (I) wherein Q is Q1, R1 is methyl, R2 is a hydrogen atom, R3 is ethylthio, and each of X and Y is methoxy,
(4) Compound (I) wherein Q is Q1, R1 is methyl, R2 is a hydrogen atom, R3 is methylthio, and each of X and Y is methoxy,
(5) Compound (I) wherein Q is Q2, R1 is methyl, R2 is ethoxy, and each of X and Y is methoxy,
(6) Compound (I) wherein Q is Q3, R1 is methyl, R2 is a hydrogen atom, R3 is methoxy, and each of X and Y is methoxy,
(7) Compound (I) wherein Q is Q3, R1 is methyl, R2 is a hydrogen atom, R3 is ethoxy, and each of X and Y is methoxy,
(8) Compound (I) wherein Q is Q4, R1 is methylsulfonyl, and each of X and Y is methoxy,
(9) Compound (I) wherein Q is Q1, R1 is methyl, R2 is a hydrogen atom, R3 is n-propyl, and each of X and Y is methoxy,
(10) Compound (I) wherein Q is Q1, R1 is a chlorine atom, R2 is a hydrogen atom, R3 is ethyl, and each of X and Y is methoxy,
(11) Compound (I) wherein Q is Q1, R1 is a chlorine atom, R2 is a hydrogen atom, R3 is n-propyl, and each of X and Y is methoxy,
(12) Compound (I) wherein Q is Q1, R1 is methyl, R2 is a hydrogen atom, R3 is i-propyl, and each of X and Y is methoxy,
(13) Compound (I) wherein Q is Q1, R1 is a chlorine atom, R2 is a hydrogen atom, R3 is i-propyl, and each of X and Y is methoxy,
(14) Compound (I) wherein Q is Q1, R1 is a chlorine atom, R2 is a hydrogen atom, R3 is cyclopropyl, and each of X and Y is methoxy, and
(15) Compound (I) wherein Q is Q1, R1 is a fluorine atom, R2 is a hydrogen atom, R3 is n-propyl, and each of X and Y is methoxy.

Compound (I) can occur as optical isomers, diastereomers and/or geometric isomers, and this invention encompasses such isomers and mixtures thereof.

Acidic groups such as sulfo group, carboxyl group etc. in substituent groups in the molecule of Compound (I) can form agrochemically acceptable basic salts with an inorganic base, organic base etc., and basic nitrogen atoms in the molecule and basic groups such as amino acid groups in substituent groups can form agrochemically acceptable acid addition salts with an inorganic acid, organic acid etc. The inorganic basic salts include, for example, salts with alkali metals (e.g., sodium, potassium etc.), alkaline earth metals (e.g., calcium etc.) and ammonia etc., and the organic basic salts include salts with e.g. dimethylamine, triethylamine, N,N-dimethylaniline, piperazine, pyrrolidine, piperidine, pyridine, 2-phenylethylamine, benzylamine, ethanolamine, diethanolamine, 1,8-diazabicyclo[5,4,0]undecene (abbreviated hereinafter as DBU) etc. The inorganic acid addition salts of Compound (I) include salts with e.g. hydrochloric acid, hydrobromic acid, hydriodic acid, sulfuric acid, nitric acid, phosphoric acid, perchloric acid etc., and the organic acid addition salts of Compound (I) include salts with e.g. formic acid, acetic acid, propionic acid, oxalic acid, succinic acid, benzoic acid, p-toluenesulfonic acid, methanesulfonic acid, trifluoroacetic acid etc.

Compound (I) can be produced according to a method described in e.g. JP-A 64-38091, and its specific method is shown in the Examples described later.

When Compound (I) is in a crystalline form, Compound (I) shows crystalline polymorphism or pseudo-crystalline polymorphism depending on crystallization conditions, and Compound (I) even having a chemical structure giving the same nuclear magnetic resonance spectrum may give a different infrared absorption spectrum. This invention encompasses not only crystalline forms of Compound (I) showing such crystalline polymorphism and pseudo-crystalline polymorphism but also mixed crystals thereof.

Upon application to paddy-rice plants particularly during or after planting, Compound (I) or a salt thereof has extremely excellent selectivity for paddy-rice plants, and exhibits a high weeding effect on weeds resistant to sulfonylurea herbicides.

When Compound (I) or a salt thereof is used as a pesticide, particularly a herbicide, it can be used in a general agrochemical form, that is, in a formulation such as, for example, an emulsion, oil, spray, hydrate, powder, DL (drift-less) powder, granules, finely divided particles, a finely divided agent F, a flowable agent, a dry flowable agent, jumbo granules, tablets etc. by dissolving or suspending one or more of Compound (I) or salts thereof in a suitable liquid carrier depending on the intended use or by mixing them with, or adsorbing them onto, suitable solid carriers. These formulations may be blended if necessary with an emulsifier, a dispersant, a spreading agent, a penetrating agent, a wetting agent, a thickener and a stabilizer, and can be prepared by a method known per se.

The liquid carrier (solvent) used is preferably a solvent such as, for example, water, alcohols (e.g., methanol, ethanol, 1-propanol, 2-propanol, ethylene glycol etc.), ketones (e.g., acetone, methyl ethyl ketone etc.), ethers (e.g., dioxane, tetrahydrofuran, ethylene glycol monomethyl ether, diethylene glycol monomethyl ether, propylene glycol monomethyl ether etc.), aliphatic hydrocarbons (e.g., kerosine, fuel oil, machine oil etc.), aromatic hydrocarbons (e.g., benzene, toluene, xylene, solvent naphtha, methyl naphthalene etc.), halogenated hydrocarbons (e.g., dichloromethane, chloroform, carbon tetrachloride etc.), acid amides (e.g., dimethylformamide, dimethylacetamide etc.), esters (e.g., ethyl acetate, butyl acetate, fatty glycerin ester etc.), nitriles (e.g., acetonitrile, propionitrile etc.) etc., and these may be used alone or as a mixture thereof in a suitable ratio. The solid carriers (diluents and fillers) include plant powders (e.g., soybean powder, tobacco powder, wheat flour, wood flour etc.), mineral powders (e.g., clays such as kaolin, bentonite, acid clay, and clay, talc such as talcum powder and agalmatolite powder, and silica such as diatomaceous earth and mica powder), alumina, sulfur powder, activated carbon etc., and these are used alone or as a mixture thereof in a suitable ratio. The liquid carrier or solid carrier can be used in an amount of usually about 1 to 99% by weight, preferably about 1 to 80% by weight, based on the whole of the formulation.

If necessary, surfactants used as an emulsifier, a spreading agent, a penetrating agent, a dispersant etc. can make use of non-ionic and anionic surfactants such as soaps, polyoxyethylene alkyl aryl ethers (e.g., Neugen™, E·A 142™ (TM: registered trade mark, and so on; manufactured by Dai-ichi Kogyo Seiyaku Co., Ltd.), polyoxyethylene aryl esters (e.g., Nonal™, manufactured by Toho Chemical Co., Ltd.), alkyl sulfates (e.g., Yumal 10™, Yumal 40™, manufactured by Kao Corporation), alkyl sulfonates (e.g., Neogen™, Neogen T™, manufactured by Dai-ichi Kogyo Seiyaku Co., Ltd.; Neopelex™, manufactured by Kao Corporation), polyethylene glycol ethers (e.g., Nonipol 85™, Nonipol 100™, Nonipol 160™, manufactured by Sanyo Chemical Industries, Ltd.) and polyvalent alcohol esters (e.g., Tween 20™, Tween 80™, manufactured by Kao Corporation) The surfactants can be used in an amount of usually about 0.1 to 50% by weight, preferably about 0.1 to 25% by weight, based on the whole of the formulation.

The content of Compound (I) or a salt thereof in the herbicide is preferably about 1 to 90% by weight in an emulsion, a hydrate etc., about 0.01 to 10% by weight in an oil, powder, DL (drift-less) powder, and about 0.05 to 10% by weight in a finely divided agent F and granules, but depending on the intended use, the concentration may be suitably changed. An emulsion, a hydrate and the like are diluted suitably (e.g. 100- to 100,000-fold) with water or the like on the occasion of use and sprayed.

When Compound (I) or a salt thereof is used as a herbicide, the amount thereof is varied depending on the application field, application period, application method, target weeds, cultivated products etc., but generally the amount of the active ingredient (Compound (I) or a salt thereof) is about 0.05 to 50 g, preferably about 0.1 to 5 g/are of paddy field, or about 0.04 to 10 g, preferably about 0.08 to 5 g/are of field.

For application to weeds in fields, Compound (I) or a salt thereof is used preferably as an agent for treating soil before germination or for treating stems, leaves and soil. For example, the herbicide of the present invention can be used safely even after 2 to 3 weeks without developing any herbicide injury.

The herbicide containing Compound (I) or a salt thereof of this invention can be applied simultaneously with 1 or more (preferably 1 to 3) other herbicides, plant growth regulators, bactericides, insecticides, acaricides, nematocides etc., if necessary. Further, the herbicide of this invention can be used as a blend with 1 or more (preferably 1 to 3) of other herbicides, plant growth regulators, bactericides, insecticides, acaricides, nematocides and the like. The other herbicides (weeding active ingredients) include, for example, (1) sulfonylurea herbicides (chlorsulfuron, sulfometuron-methyl, chlorimuron-ethyl, triasulfuron, amidosulfuron, oxasulfuron, tribenuron-methyl, prosulfuron, ethametsulfuron-methyl, triflusulfuron-methyl, thifensulfuron-methyl, flazasulfuron, rimsulfuron, nicosulfuron, flupyrsulfuron, bensulfuron-methyl, pyrazosulfuron-ethyl, imazosulfuron, sulfosulfuron, cinosulfuron, azimsulfuron, metsulfuron-methyl, halosulfuron-methyl, ethoxysulfuron, cyclosulfamuron, iodosulfuron etc.), (2) pyrazol herbicides (pyraflufen-ethyl, pyrazolate, pyrazoxyfen, benzofenap etc.), (3) carbamate herbicides (diallate, butylate, tri-allate, phenmedipham, chlorpropham, asulam, phenisopham, benthiocarb, molinate, esprocarb, pyributicarb, dimepiperate, swep etc.), (4) chloroacetoanilide herbicides (propachlor, metazachlor, alachlor, acetochlor, metolachlor, butachlor, pretilachlor, thenylchlor etc.), (5) diphenyl ether herbicides (acifluorfen, oxyfluorfen, lactofen, fomesafen, aclonifen, chlomethoxynil, bifenox, CNP etc.), (6) triazine herbicides (simazine, atrazine, propazine, cyanazine, ametoryn, simetryn, dimethametryn, prometryn etc.), (7) phenoxy acid or benzoic acid herbicides (2,3,6-TBA, dicamba, quinclorac, quinmerac, clopyralid, picloram, triclopyr, fluroxypyr, benazolin, diclofop-methyl, fluazifop-butyl, haloxyfop-methyl, quizalofop-ethyl, cyhalohop-butyl, 2,4-PA, MCP, MCPB, phenothiol etc.), (8) acid amide or urea herbicides (isoxaben, diflufenican, diuron, linuron, fluometuron, difenoxuron, methyl-daimuron, isoproturon, isouron, tebuthiuron, methabenzthiazuron, propanil, mefenacet, clomeprop, naproanilide, bromobutide, daimuron, cumyluron, etobenzanid, oxazichlomefone etc.), (9) organic phosphorus herbicides (glyphosate, bialaphos, amiprofos-methyl, anilofos, bensulide, piperophos, butamifos, anilofos etc.), (10) dinitroaniline herbicides (bromoxynil, ioxynil, dinoseb, trifluralin, prodiamine etc.), (11) cyclohexanedione herbicides (alloxydim, sethoxydim, cloproxydim, clethodim, cycloxydim, tralkoxydim etc.), (12) imidazoline herbicides (imazamethabenz, imazapyr, imazamethapyr, imazethapyr, imazamox, imazaquin etc.), (13) bipyridium herbicides (paraquat, diquat etc.), (14) other herbicides (bentazon, tridiphane, indanofan, amitrole, carfentrazon-ethyl, sulfentrazon, fenchlorazole-ethyl, fentrazamide, isoxaflutole, clomazone, maleic hydrazide, pyridate, chloridazon, norflurazon, pyrithiobac, bromacil, terbacil, metribuzin, oxaziclomefone, cinmethylin, flumiclorac-pentyl, cinidon-ethyl, flumioxazin, fluthiacet-methyl, azafenidin, benfuresate, oxadiazon, oxadiargyl, pentoxazone, cyhalofop-butyl, cafenstrole, pyriminobac-methyl, bispyribac-sodium, pyribenzoxim, pyriftalid, fentrazamide, indanofan, ACN, benzobicylon, dithiopyr, dalapon, chlorthiamid etc.) etc.

The plant growth regulators (plant growth regulating active ingredients) include, for example, hymexazol, paclobutrazol, uniconazole-P, inabenfide, prohexadione-calcium etc. The bactericides (bactericidal active ingredients) include, for example, (1) polyhaloalkylthio bactericides (captan etc.), (2) organophosphorus bactericides (IBP, EDDP, tolclofos-methyl etc.), (3) benzimidazole bactericides (benomyl, carbendazim, thiophanate-methyl etc.), (4) carboxyamide bactericides (mepronil, flutolanil, thifluzamid, furametpyr, teclofthalam, Pencycuron, carpropamid, diclocymet etc.), (5) acylalanine bactericides (metalaxyl etc.), (6) azole bactericides (triflumizole, ipconazole, pefurazoate, prochloraz etc.), (7) methoxyacrylic acid bactericides (azoxystrobin, metominostrobin etc.), (8) antibiotic bactericides (validamycin A, blasticidin S, kasugamycin, polyoxin etc.), (9) other bactericides (fthalide, probenazole, isoprothiolane, tricyclazole, pyroquiln, ferimzone, acibnzolar S-methyl, diclomezine, oxolinic acid, phenazine oxide, TPN, iprodione etc.) etc. The insecticides (insecticidal active ingredients) include, for example, (1) organophosphorus insecticides (fenthion, fenitrothion, pirimiphos-methyl), diazinon, quinalphos, isoxathion, Pyridafenthion, chlorpyrifos-methyl, vamidothion, malathion, phenthoate, dimethoate, disulfoton, monocrotophos, tetrachlorvinphos, chlorfenvinphos, propaphos, acephate, trichlorphon, EPN, pyraclorfos etc.), (2) carbamate insecticides (carbaryl, metolcarb, isoprocarb, BPMC, propoxur, XMC, carbofuran, carbosulfan, benfuracarb, furathiocarb, methomyl, thiodicarb etc.), (3) synthetic pyrethroid insecticides (cycloprothrin, ethofenprox etc.), (4) nereistoxin insecticides (cartap, bensultap, thiocyclam etc.), (5) neonicotinoid insecticides (imidacloprid, nitenpyram, acetamiprid, thiamethoxam, thiacloprid, dinotefuran, clothianidin etc.), (6) other insecticides (buprofezin, tebufenozide, fipronil, ethiprole etc.) etc. Acaricides (acaricidal active ingredients) include, for example, hexythiazox, pyridaben, fenpyroximate, tebufenpyrad, chlorfenapyr, etoxazole, Pyrimidifen etc. The nematocides (nematocidal active ingredients) include, for example, fosthiazate etc. Such other agrochemical active ingredients (e.g., weeding active ingredients, plant growth regulating active ingredients, bactericidal active ingredients, insecticidal active ingredients, acaricidal active ingredients, nematocidal active ingredients etc.) can be used in an amount of usually about 0.1 to 20% by weight, preferably about 0.1 to 10% by weight, based on the whole of the preparation.

The herbicide containing Compound (I) or a salt thereof of the present invention may be mixed if necessary with synergists (e.g., piperonyl butoxide etc.), incitements (e.g., eugenol etc.), repellents (e.g., creosote etc.), pigments (e.g., Edible Blue No. 1, etc.) and fertilizers (e.g., urea etc.).

EXAMPLES

Hereinafter, this invention is described in more detail by the Reference Examples (Synthesis Examples for synthetic intermediates), Synthesis Examples, Preparation Examples and Test Examples, but this invention is not limited thereto.

As the elution solvent in column chromatography in the Reference Examples and Synthesis Examples, a solvent used for observation in TLC (thin layer chromatography) was used. For observation in TLC, silica gel 60F$_{254}$ TLC plate manufactured by Merck was used, and a UV detector was used for detection. As silica gel for column, silica gel 60 (0.063 to 0.200 mm) manufactured by Merck was used. When a mixed solvent was used as the elution solvent, a mixing ratio of solvents by volume is shown in brackets.

Proton nuclear magnetic resonance spectra ($^1$H NMR) were determined with Bruker AC-200P (200 MHz) and Bruker AV-400 (400 MHz) spectrometers with tetramethylsilane as internal standard, and all delta values are shown in ppm. Fluorine nuclear magnetic resonance spectra ($^{19}$F NMR) were determined with Bruker AC-200P (188 MHz) and Bruker AV-400 (376 MHz) spectrometers with fluorotrichloromethane as internal standard, and all delta values are shown in ppm.

Infrared absorption spectra (IR) were determined with Perkin-Elmer Paragon 100 model FT-IR spectrometer, and absorption band positions are shown in wave-number (cm$^{-1}$). Melting points were measured with Yanagimoto microquantity melting point measuring device.

The abbreviations used in the Reference Examples, Synthesis Examples and tables have the following meanings: Me: methyl group, Et: ethyl group, n-Pr: normal propyl group, i-Pr: isopropyl group, c-Pr: cyclopropyl group, n-Bu: normal butyl group, i-Bu: isobutyl group, TMS: trimethylsilyl group, s: singlet, d: doublet, t: triplet, q: quartet, br: broad, m: multiplet, dd: double doublet, dt: double triplet, tt: triple triplet, dq: double quartet, tq: triple quartet, brs: broad singlet, J: coupling constant, CDCl$_3$: heavy chloroform, DMSO-d$_6$: heavy dimethyl sulfoxide, mp: melting point, dec.: decomposition, Hz: Hertz, THF: tetrahydrofuran, DMF: N,N-dimethylformamide, dppp: 1,3-bis(diphenylphosphino)propane.

Reference Example 1

Synthesis of 6-ethyl-2-methylimidazo[1,2-b]pyridazine

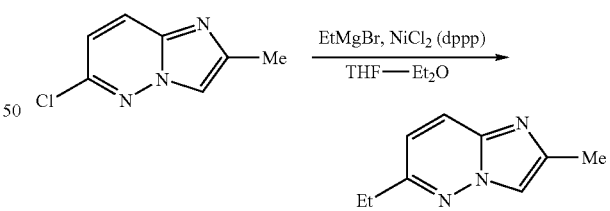

6-Chloro-2-methylimidazo[1,2-b]pyridazine (5.00 g, 29.8 mmol) and [1,3-bis(diphenylphosphino)propane]nickel (II) dichloride (0.08 g, 0.15 mmol) were suspended in dry ether (40 ml)-dry THF (20 ml) and then stirred under ice-cooling, during which a solution of ethylmagnesium bromide in ether (3 M, 15 ml, 45 mmol) was added dropwise thereto over 5 minutes (internal temperature 10° C. or less). The temperature of the reaction solution was increased to room temperature, and the mixture was stirred at the same temperature for 2 hours and under reflux with heating for 3 hours. The reaction solution, while being stirred, was left and cooled to room temperature, and water (30 ml) was added little by little.

Further, the reaction mixture was stirred at room temperature and adjusted to about pH 5 to 6 with conc. hydrochloric acid. The organic layer and the aqueous layer were separated from each other, and the aqueous layer was extracted with ethyl acetate (70 ml×2). The organic layers were combined and washed with water (250 ml×3). The organic layer was dried over magnesium sulfate and concentrated, and the residues were purified by silica gel column chromatography (chloroform:ethyl acetate=2:1→1:1), and the resulting crude oil was further purified by silica gel column chromatography (ethyl acetate), and the title compound was obtained as pale red oil. The yield was 1.32 g (27.4%).

$^1$H NMR (CDCl$_3$, δ): 1.33 (3H, t, J=7.5 Hz), 2.48 (3H, s), 2.82 (2H, q, J=7.5 Hz), 6.87 (1H, d, J=9.2 Hz), 7.65 (1H, s), 7.72 (1H, d, J=9.2 Hz)

IR (Neat, cm$^{-1}$): 2973, 2934, 2876, 1543, 1460, 1382, 1333, 1300, 1263, 1155, 1125, 1057, 1000, 820, 726, 699

Reference Example 2

Synthesis of 6-ethyl-2-methylimidazo[1,2-b]pyridazin-3-ylsulfonamide

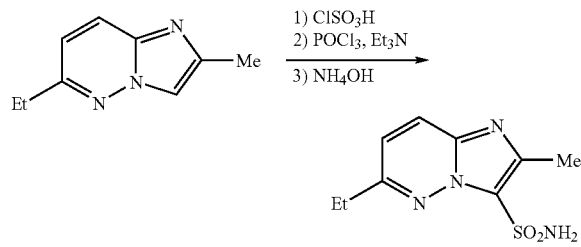

6-Ethyl-2-methylimidazo[1,2-b]pyridazine (2.70 g, 16.7 mmol) was dissolved in 1,2-dichloroethane (30 ml), and chlorosulfonic acid (1.27 g, 18.5 mmol) was added thereto under stirring at room temperature, and the mixture was stirred for 5 hours under reflux. Then, the reaction solution was cooled to about 70° C., and triethylamine (2.38 g, 23.5 mmol) was added dropwise thereto over 1 minute. After dropping, the reaction solution was stirred for 20 minutes under reflux. Thereafter, the reaction solution was cooled to about 70° C., and phosphorus oxychloride (3.86 g, 25.2 mmol) was added dropwise thereto over 1 minute. After dropping, the mixture was stirred for 2 hours under reflux. The reaction solution was left and cooled to about 50° C., and poured into 50 ml warm water (about 50° C.). The mixture was stirred for 5 minutes, and the organic layer was separated. The aqueous layer was extracted with chloroform (50 ml×2). The organic layers were combined, washed with water, dried over magnesium sulfate, and concentrated. The residues were dissolved in acetonitrile (40 ml), and 14 N ammonia water (7 ml) was added thereto under stirring at room temperature, and the mixture was stirred at room temperature for 2 hours. After the reaction was completed, the reaction solution was poured onto iced water (150 ml) and adjusted to about pH 4 with conc. hydrochloric acid, to form crystals which were then collected by filtration, washed with water and dried under reduced pressure. Thereafter, the crystals were purified by silica gel column chromatography (chloroform:acetone=9:1→4:1). The title compound was obtained as white crystals. The yield was 1.8 g (44.7%).

mp 215.0-215.5° C.

$^1$H NMR (DMSO-d$_6$, δ): 1.30 (3H, t, J=7.5 Hz), 2.57 (3H, s), 2.93 (2H, q, J=7.5 Hz), 7.39 (1H, d, J=9.3 Hz), 7.47 (2H, brs), 8.08 (1H, d, J=9.3 Hz)

IR (Nujol, cm$^{-1}$): 3304, 3177, 3090, 1546, 1540, 1507, 1463, 1389, 1362, 1341, 1309, 1201, 1166, 1127, 1086, 1057, 959, 900, 864, 824, 772, 686, 670, 652, 591, 525

Reference Example 3

Synthesis of 2-chloro-6-n-propylimidazo[1,2-b]pyridazine

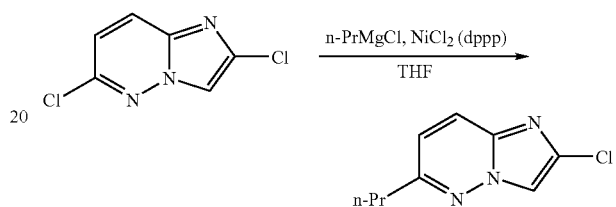

2,6-Dichloroimidazo[1,2-b]pyridazine (1.6 g, 8.5 mmol), [1,3-bis(diphenylphosphino)propane]nickel (II) dichloride (catalytic amount) and dehydrated tetrahydrofuran (20 ml) were introduced into a 100-ml three-necked flask under a nitrogen stream and stirred under ice-cooling, and a solution of propylmagnesium chloride in tetrahydrofuran (2 M, 6.4 ml, 12.8 mmol) was added dropwise thereto at 10° C. or less. After dropping, the mixture was stirred for 1 hour at the same temperature, for 1 hour at room temperature and for 2 hours at 50 to 60° C. After the reaction was completed, the reaction solution was left and cooled, and water (50 ml) was added thereto, and the mixture was stirred and extracted with ethyl acetate (20 ml×2). The organic layers were combined, washed with water, dried over magnesium sulfate and concentrated, and the residues were purified by silica gel column chromatography (hexane:ethyl acetate=2:1) to give the title compound as orange crystals (containing a small amount of impurities). The yield was 0.8 g (48.2%).

mp: not measured.

$^1$H NMR (CDCl$_3$, δ): 1.01 (3H, t, J=7.3 Hz), 1.7-1.9 (2H, m), 2.79 (2H, t, J=7.6 Hz), 6.96 (1H, d, J=9.3 Hz), 7.75 (1H, d, J=9.3 Hz), 7.80 (1H, s)

Reference Example 4

Synthesis of 2-chloro-6-n-propylimidazo[1,2-b]pyridazin-3-ylsulfonamide

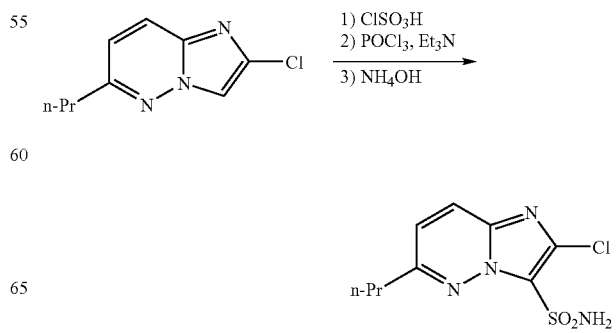

2-Chloro-6-n-propylimidazo[1,2-b]pyridazine (0.8 g, 4.1 mmol) and dichloroethane (10 ml) were introduced into a 200-ml eggplant type flask and stirred at room temperature, and chlorosulfonic acid (0.54 g, 4.5 mmol) was added thereto all at once, and the mixture was stirred for 4 hours under reflux. The reaction solution was cooled to about 70° C., and triethylamine (0.5 g, 5 mmol) was added thereto all at once and stirred until the solid was dissolved, and phosphorus oxychloride (0.79 g, 5 mmol) was added thereto all at once, and the mixture was stirred for 2 hours under reflux with heating. After the reaction was completed, the reaction solution was left and cooled, and water (50 ml) was added thereto and the organic phase was separated. The organic phase was washed with a saturated saline solution, dried over magnesium sulfate and concentrated, and acetonitrile (10 ml) and 28% ammonia water (4 ml) were added to the residue and stirred at room temperature for 2 hours. After the reaction was completed, water (100 ml) was added to the reaction solution which was then adjusted to about pH 2 with dilute hydrochloric acid, and the formed crystals were collected by filtration, washed with water and chloroform and dried under reduced pressure, to give the title compound as pale brown crystals. The yield was 0.49 g (43.5%; 3 steps).

mp 174-5° C.

$^1$H NMR (DMSO-d$_6$, δ): 0.96 (3H, t, J=7.4 Hz), 1.7-1.9 (2H, m), 2.8-3.0 (2H, m), 7.53 (1H, d, J=9.5 Hz), 7.82 (2H, brs), 8.19 (1H, d, J=9.4 Hz)

IR (Nujol, cm$^{-1}$): 3377, 3324, 3189, 1545, 1364, 1322, 1187, 1166, 821, 680, 597

Reference Example 5

Synthesis of 6-n-butyl-2-chloroimidazo[1,2-b]pyridazine

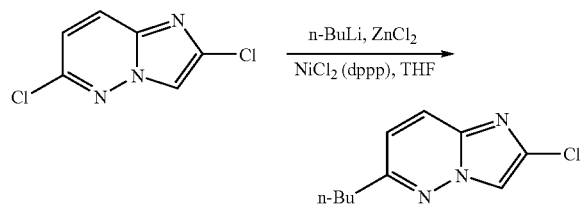

Zinc chloride (2.04 g, 15.0 mmol) was dried at 180° C. for 2 hours under vacuum and then cooled to room temperature, and anhydrous tetrahydrofuran (20.0 mL) was added thereto. n-Butyl lithium (1.6 M, 9.0 mL, 14.4 mmol) was added dropwise thereto over about 30 minutes under ice-cooling and stirred for 30 minutes under ice-cooling, to prepare a solution of n-butylzinc chloride in tetrahydrofuran. Separately, a suspension of 2,6-dichloroimidazo[1,2-b]pyridazine (1.88 g, 10.0 mmol) and [1,3-bis(diphenylphosphino)propane]nickel (II) dichloride (0.16 g, 0.30 mmol) in anhydrous tetrahydrofuran (20.0 mL) was prepared under a nitrogen atmosphere, and the previously prepared solution of n-butylzinc chloride in tetrahydrofuran while being maintained at 3 to 6° C. was added dropwise thereto over 30 minutes. The mixture was stirred for 15 minutes under ice-cooling and for 3 hours at room temperature, then poured into a saturated saline solution and adjusted to pH 2 with dilute hydrochloric acid. The reaction solution was extracted twice with ethyl acetate, and the extracts were combined, dehydrated over anhydrous magnesium sulfate and concentrated under reduced pressure. The residues were purified by silica gel column chromatography (ethyl acetate:hexane=1:4), to give the title compound as pale yellow crystals. The yield was 2.03 g (96.8%).

mp 61.0-63.0° C.

$^1$H NMR (CDCl$_3$, δ): 0.96 (3H, t, J=7.3 Hz), 1.41 (2H, tq, J=7.5, 7.3 Hz), 1.73 (2H, tt, J=7.8, 7.5 Hz), 2.81 (2H, t, J=7.8 Hz), 6.96 (1H, d, J=9.4 Hz), 7.74 (1H, d, J=9.4 Hz), 7.79 (1H, s).

IR (Nujol, cm$^{-1}$): 3115, 3061, 1545, 1466, 1378, 1326, 1276, 817.

Reference Example 6

Synthesis of 6-n-butyl-2-chloroimidazo[1,2-b]pyridazin-3-ylsulfonamide

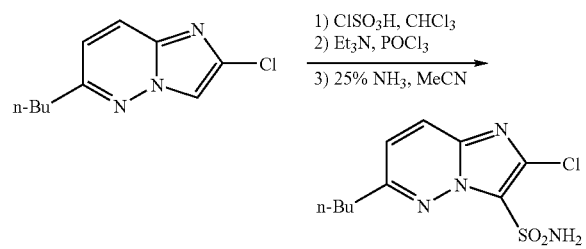

6-n-Butyl-2-chloroimidazo[1,2-b]pyridazine (1.00 g, 4.77 mmol) was dissolved in chloroform (10.0 mL), and chlorosulfonic acid (0.35 mL, 5.27 mmol) was added dropwise to the solution under stirring at room temperature. After the mixture was heated for 5 hours under reflux, it was confirmed by TLC that the starting material remained, so additional chlorosulfonic acid (0.35 mL, 5.27 mmol) was added thereto, and the mixture was heated for 4 hours under reflux. The resulting suspension was left and cooled to room temperature, and triethylamine (2.50 mL, 17.9 mmol) and phosphorus oxychloride (2.00 mL, 21.5 mmol) were added thereto, and the mixture was heated again for 4 hours under reflux. The reaction solution was cooled to room temperature, poured into water and extracted 3 times with chloroform, and the extracts were combined, dehydrated over anhydrous magnesium sulfate and concentrated under reduced pressure to give 3.24 g dark red liquid. This liquid was dissolved in acetonitrile (10.0 mL) and added dropwise to a solution of 25% ammonia water (5.00 g, 73.5 mmol) in acetonitrile (15.0 mL) under ice-cooling. The mixture was stirred for 30 minutes under ice-cooling and for 1 hour at room temperature, and the acetonitrile was then distilled away under reduced pressure. The residues were adjusted to pH 2 with dilute hydrochloric acid and extracted twice with chloroform, and the chloroform layers were combined, dehydrated over anhydrous magnesium sulfate and concentrated under reduced pressure. The residues were purified by silica gel column chromatography (ethyl acetate:hexane=1:1→chloroform:ethanol=20:1), to give the title compound as white crystals. The yield was 0.92 g (66.8%).

mp 165.5-166.5° C.

$^1$H NMR (DMSO-d$_6$, δ): 0.93 (3H, t, J=7.3 Hz), 1.37 (2H, tq, J=7.5, 7.3 Hz), 1.72 (2H, tt, J=7.9, 7.5 Hz), 2.93 (2H, t, J=7.9 Hz), 7.53 (1H, d, J=9.4 Hz), 7.80 (2H, s), 8.18 (1H, d, J=9.4 Hz).

IR (Nujol, cm$^{-1}$): 3412, 3360, 3287, 3197, 1546, 1464, 1376, 1321, 1172.

Reference Example 7

Synthesis of N'-(2,6-dichloroimidazo[1,2-b]pyridazin-3-ylsulfonyl)-N,N-diisobutylformamidine

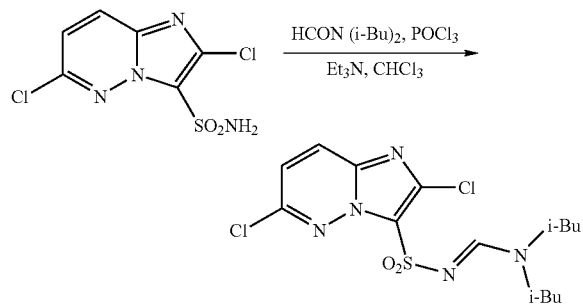

N,N-Diisobutylformamide (5.44 g, 34.5 mmol) was dissolved in chloroform (25.0 mL) and cooled in an ice-sodium chloride bath, and phosphorus oxychloride (3.22 mL, 34.5 mmol) was added dropwise thereto at −2° C. or less. After the mixture was stirred at −2° C. or less for 30 minutes, 2,6-dichloroimidazo[1,2-b]pyridazin-3-ylsulfonamide (6.15 g, 23.0 mmol) was added thereto. After the mixture was stirred at −10° C. for 10 minutes, triethylamine (19.3 mL, 138 mmol) was added dropwise over 20 minutes to the solution at 5° C. or less. The mixture was stirred for 1 hour at 0° C. or less and for 1 hour at room temperature, then poured into an aqueous saturated sodium bicarbonate and extracted 5 times with chloroform. The extracts were combined, dehydrated over anhydrous magnesium sulfate and concentrated under reduced pressure. The residues were purified by silica gel column chromatography (ethyl acetate:hexane=1:1) to give the title compound as pale yellow crystals. The yield was 5.58 g (59.6%).

mp 151.0-154.0° C.

$^1$H NMR (CDCl$_3$, δ): 0.76 (6H, d, J=6.7 Hz), 0.97 (6H, d, J=6.7 Hz), 1.90-2.10 (2H, m), 3.23 (2H, d, J=7.6 Hz), 3.28 (2H, d, J=7.7 Hz), 7.26 (1H, d, J=9.5 Hz), 7.90 (1H, d, J=9.5 Hz), 8.51 (1H, s).

IR (Nujol, cm$^{-1}$): 1615, 1456, 1324, 1311, 1146, 910, 858, 654.

Reference Example 8

Synthesis of N'-(2-chloro-6-cyclopropylimidazo[1,2-b]pyridazin-3-ylsulfonyl)-N,N-diisobutylformamidine

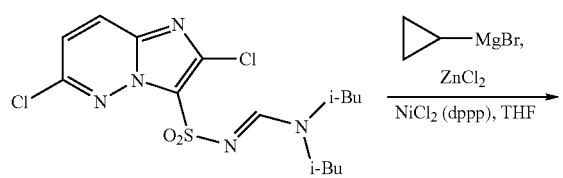

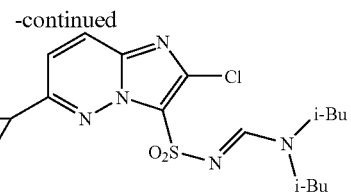

Magnesium metal powder (0.27 g, 11.1 mmol) was mixed with iodine (5 mg), heated with a dryer under a nitrogen atmosphere and cooled to room temperature, and anhydrous tetrahydrofuran (15.0 mL) was added thereto. Cyclopropyl bromide (1.33 g, 1.10 mmol), while being kept at 28 to 33° C., was added dropwise to the mixture under stirring at room temperature, and then the mixture was stirred at room temperature for 30 minutes to prepare a pale yellowish gray solution of cyclopropylmagnesium bromide in tetrahydrofuran. Separately, zinc chloride (1.50 g, 11.0 mmol) dried at 180° C. for 4 hours under vacuum was dissolved in anhydrous tetrahydrofuran (10.0 mL) under a nitrogen atmosphere and then kept at 0° C. or less in an ice-sodium chloride bath, during which the previously prepared solution of cyclopropylmagnesium bromide in tetrahydrofuran was added dropwise thereto. The mixture was stirred at about −10° C. for 15 minutes, and [1,3-bis(diphenylphosphino)propane]nickel (II) dichloride (0.27 g, 0.50 mmol) was added as powder to the resulting suspension, and then a solution of N'-(2,6-dichloroimidazo[1,2-b]pyridazin-3-ylsulfonyl)-N,N-diisobutylformamidine (2.03 g, 5.00 mmol) dissolved in anhydrous tetrahydrofuran (10.0 mL) was added dropwise thereto. The mixture was stirred at −10° C. for 2 hours, then at room temperature for 16 hours, poured into an aqueous saturated saline solution, adjusted to pH 2 with dilute hydrochloric acid and extracted 4 times with chloroform. The extracts were combined, dehydrated over anhydrous magnesium sulfate and concentrated under reduced pressure, and the residues were purified by silica gel column chromatography (ethyl acetate:hexane=1:1), whereby 0.64 g (31.5%) of the starting material N'-(2,6-dichloroimidazo[1,2-b]pyridazin-3-ylsulfonyl)-N,N-diisobutylformamidine was recovered and simultaneously the title compound was obtained as pale yellow crystals. The yield was 0.94 g (45.7%).

mp 154.0-160.0° C.

$^1$H NMR (CDCl$_3$, δ): 0.74 (6H, d, J=6.7 Hz), 0.95 (6H, d, J=6.7 Hz), 1.00-1.10 (2H, m), 1.10-1.25 (2H, m), 1.85-2.10 (2H, m), 2.10-2.20 (1H, m), 3.19 (2H, d, J=7.5 Hz), 3.28 (2H, d, J=7.5 Hz), 6.98 (1H, d, J=9.4 Hz), 7.78 (1H, d, J=9.4 Hz), 8.45 (1H, s)

IR (Nujol)ν(cm$^{-1}$): 1613, 1464, 1334, 1318, 1143, 909, 859, 661.

Reference Example 9

Synthesis of N'-(2-chloro-6-ethenylimidazo[1,2-b]pyridazin-3-ylsulfonyl)-N,N-diisobutylformamidine

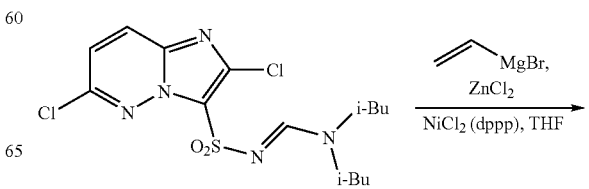

-continued

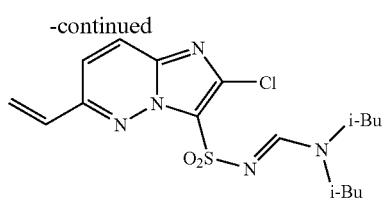

The title compound was obtained as pale yellow crystals by the same reaction as in Reference Example 8 except that a solution of commercially available vinyl magnesium bromide in tetrahydrofuran was used in place of the solution of cyclopropylmagnesium bromide in tetrahydrofuran, and [1,3-bis(diphenylphosphino)propane]nickel (II) dichloride was used in an amount of 3 mol-% relative to the starting material N'-(2,6-dichloroimidazo[1,2-b]pyridazin-3-ylsulfonyl)-N,N-diisobutylformamidine. The yield was 80.4%.

mp 194.0-198.0° C.

$^1$H NMR (CDCl$_3$, δ): 0.71 (6H, d, J=6.7 Hz), 0.94 (6H, d, J=6.6 Hz), 1.85-2.10 (2H, m), 3.17 (2H, d, J=7.5 Hz), 3.26 (2H, d, J=7.7 Hz), 5.77 (1H, d, J=11.1 Hz), 6.16 (1H, d, J=17.8 Hz), 6.82 (1H, dd, J=17.8, 11.1 Hz), 7.46 (1H, d, J=9.5 Hz), 7.89 (1H, d, J=9.5 Hz), 8.50 (1H, s).

IR (Nujol, cm$^{-1}$): 1614, 1456, 1350, 1319, 1145, 913, 859, 664, 612.

Reference Example 10

Synthesis of N'-(2-chloro-6-(1-propenyl)imidazo[1,2-b]pyridazin-3-ylsulfonyl)-N,N-diisobutylformamidine

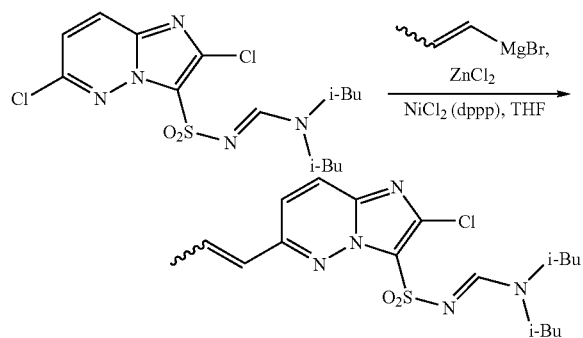

The title compound was obtained as a mixture of E and Z (E:Z=5:3) in the form of pale yellow crystals by the same reaction as in Reference Example 8 except that a solution of commercially available 1-propenylmagnesium bromide in tetrahydrofuran was used in place of the solution of cyclopropylmagnesium bromide in tetrahydrofuran, and [1,3-bis(diphenylphosphino)propane]nickel (II) dichloride was used in an amount of 3 mol-% relative to the starting material N'-(2,6-dichloroimidazo[1,2-b]pyridazin-3-ylsulfonyl)-N,N-diisobutylformamidine. The yield was 100%.

mp: not be measured because of a mixture of E and Z.

$^1$H NMR (CDCl$_3$, δ): [E isomer] 0.72 (6H, d, J=6.6 Hz), 0.94 (6H, d, J=6.6 Hz), 1.85-2.10 (2H, m), 2.00 (3H, dd, J=6.9, 1.5 Hz), 3.17 (2H, d, J=7.6 Hz), 3.26 (2H, d, J=7.7 Hz), 6.51 (1H, dq, J=16.0, 1.5 Hz), 6.71 (1H, dq, J=16.0, 6.9 Hz), 7.35 (1H, d, J=9.5 Hz), 7.82 (1H, d, J=9.5 Hz), 8.50 (1H, s).

$^1$H NMR (CDCl$_3$, δ): [Z isomer] 0.72 (6H, d, J=6.6 Hz), 0.92 (6H, d, J=6.6 Hz), 1.85-2.10 (2H, m), 2.21 (3H, dd, J=7.3, 1.8 Hz), 3.12 (2H, d, J=7.5 Hz), 3.25 (2H, d, J=7.7 Hz), 6.23 (1H, dq, J=11.9, 7.3 Hz), 6.40 (1H, dq, J=11.9, 1.8 Hz), 7.19 (1H, d, J=9.5 Hz), 7.85 (1H, d, J=9.5 Hz), 8.43 (1H, s).

IR (Nujol, cm$^{-1}$): 1609, 1456, 1351, 1319, 1144, 911.

Reference Example 11

Synthesis of N'-(2-chloro-6-ethynylimidazo[1,2-b]pyridazin-3-ylsulfonyl)-N,N-diisobutylformamidine

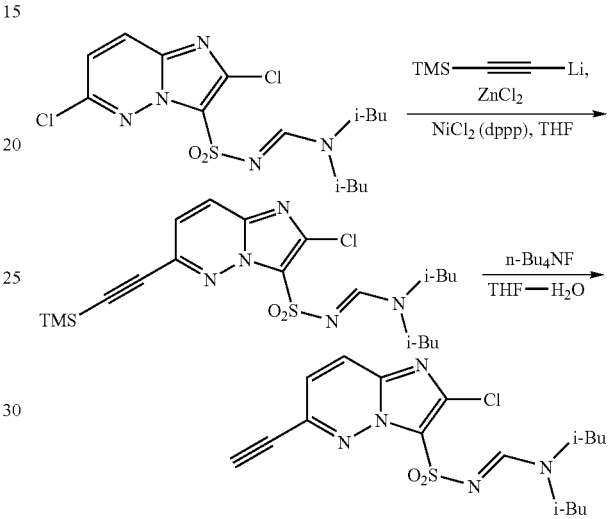

(a) N'-(2-Chloro-6-(trimethylsilylethynyl)imidazo[1,2-b]pyridazin-3-ylsulfonyl)-N,N-diisobutylformamidine was obtained as pale yellow crystals by the same reaction as in Reference Example 8 except that a solution of lithium trimethylsilyl acetylide in tetrahydrofuran was used in place of the solution of cyclopropylmagnesium bromide in tetrahydrofuran, and [1,3-bis(diphenylphosphino)propane]nickel (II) dichloride was used in an amount of 3 mol-% relative to the starting material N'-(2,6-dichloroimidazo[1,2-b]pyridazin-3-ylsulfonyl)-N,N-diisobutylformamidine. The yield was 32.9%.

mp 180.0-182.0° C.

$^1$H NMR (CDCl$_3$, δ): 0.30 (9H, s), 0.73 (6H, d, J=6.7 Hz), 0.97 (6H, d, J=6.6 Hz), 1.85-2.10 (2H, m), 3.24 (2H, d, J=7.6 Hz), 3.27 (2H, d, J=7.7 Hz), 7.30 (1H, d, J=9.4 Hz), 7.86 (1H, d, J=9.4 Hz), 8.56 (1H, s).

IR (Nujol, cm$^{-1}$): 1614, 1455, 1339, 1314, 1302, 1140, 914, 864, 839.

(b) N'-(2-Chloro-6-(trimethylsilylethynyl)imidazo[1,2-b]pyridazin-3-ylsulfonyl)-N,N-diisobutylformamidine (2.31 g, 4.63 mmol) was dissolved in a mixed solvent of tetrahydrofuran-water (10:1), and tetrabutylammonium fluoride hydrate (1.50 g, 5.04 mmol) was added to the solution with stirring under ice-cooling. After the mixture was stirred for 20 minutes under ice-cooling, the tetrahydrofuran was distilled away under reduced pressure, and the residues were dissolved in ethyl acetate. The ethyl acetate solution was washed twice with water, dehydrated over anhydrous magnesium sulfate, concentrated to dryness under reduced pressure to give the title compound as pale yellow crystals. The yield was 1.96 g (100%).

mp 166.0-167.5° C.

$^1$H NMR (DMSO-d$_6$, δ): 0.68 (6H, d, J=6.6 Hz), 0.88 (6H, d, J=6.6 Hz), 1.85-2.10 (2H, m), 3.19 (2H, d, J=7.6 Hz), 3.33 (2H, d, J=7.6 Hz), 4.94 (1H, s), 7.68 (1H, d, J=9.4 Hz), 8.30 (1H, d, J=9.4 Hz), 8.45 (1H, s).

IR (Nujol, cm$^{-1}$): 3270, 2120, 1613, 1453, 1347, 1332, 1316, 1147, 870, 664.

Reference Example 12

Synthesis of 2-chloro-6-cyclopropylimidazo[1,2-b]pyridazin-3-ylsulfonamide

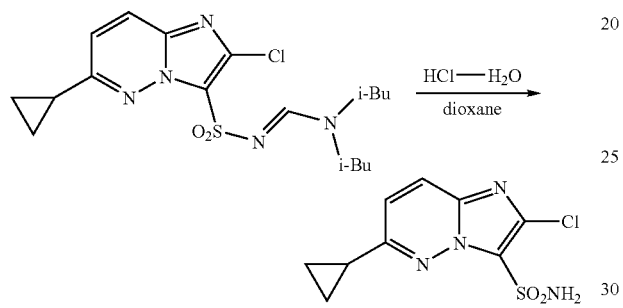

N'-(2-Chloro-6-cyclopropylimidazo[1,2-b]pyridazin-3-ylsulfonyl)-N,N-diisobutylformamidine (0.93 g, 2.26 mmol) was dissolved in dioxane (9.00 mL), and 36% conc. hydrochloric acid (9.0 mL, 107 mmol) was added dropwise to the solution under stirring at 100° C. The mixture was stirred for 15 hours at 100 to 105° C., then left and cooled to room temperature and concentrated under reduced pressure until crystals occurred. Water (30.0 mL) was poured into the residues, and the crystals were completely precipitated, then filtered, washed with water and washed with methanol, to give the title compound as white crystals. The yield was 0.31 g (50.4%).

mp 194.0-196.0° C.

NMR (DMSO-d$_6$, δ): 1.10-1.25 (4H, m), 2.30-2.45 (1H, m), 7.36 (1H, d, J=9.4 Hz), 7.78 (2H, brs), 8.12 (1H, d, J=9.4 Hz).

IR (Nujol, cm$^{-1}$): 3348, 3247, 1553, 1468, 1455, 1358, 1316, 1170, 908, 825, 662.

Reference Example 13

Synthesis of 2-chloro-6-ethenylimidazo[1,2-b]pyridazin-3-ylsulfonamide

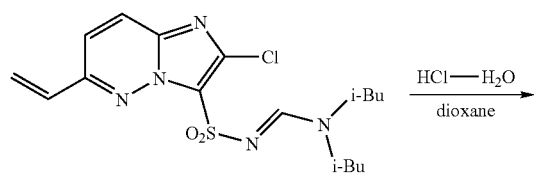

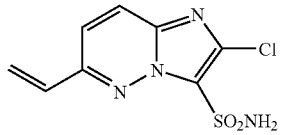

The same reaction was carried out in the same manner as in Reference Example 12 except that N'-(2-chloro-6-ethenylimidazo[1,2-b]pyridazin-3-ylsulfonyl)-N,N-diisobutylformamidine was used in place of N'-(2-chloro-6-cyclopropylimidazo[1,2-b]pyridazin-3-ylsulfonyl)-N,N-diisobutylformamidine. The resulting crystals were purified by silica gel column chromatography (chloroform:methanol=10:1), to give the title compound as white crystals. The yield was 42.1%.

mp 229.0-233.0° C.

$^1$H NMR (DMSO-d$_6$, δ): 5.87 (1H, d, J=11.2 Hz), 6.50 (1H, d, J=17.9 Hz), 6.86 (1H, dd, J=17.9, 11.2 Hz), 7.89 (2H, s), 7.96 (1H, d, J=9.6 Hz), 8.26 (1H, d, J=9.6 Hz).

IR (Nujol, cm$^{-1}$): 3316, 3183, 1466, 1368, 1321, 1167.

Reference Example 14

Synthesis of (E)-2-chloro-6-(1-propenyl)imidazo[1,2-b]pyridazin-3-ylsulfonamide

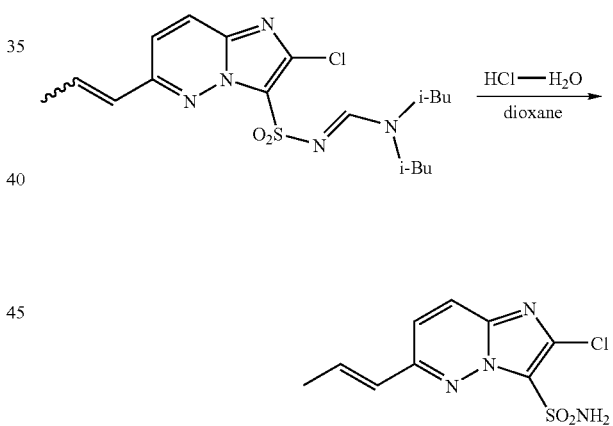

The reaction was carried out in the same manner as in Reference Example 12 except that N'-(2-chloro-6-(1-propenyl)imidazo[1,2-b]pyridazin-3-ylsulfonyl)-N,N-diisobutylformamidine as a mixture of E and Z was used in place of N'-(2-chloro-6-cyclopropylimidazo[1,2-b]pyridazin-3-ylsulfonyl)-N,N-diisobutylformamidine. The resulting crystals were purified by silica gel column chromatography (chloroform:methanol=20:1), to give the title compound as white crystals. The yield was 70.1%.

mp 225.0-229.0° C.

$^1$H NMR (DMSO-d$_6$, δ): 1.98 (3H, dd, J=6.8, 1.7 Hz), 6.71 (1H, dq, J=16.0, 1.7 Hz), 7.01 (1H, dq, J=16.0, 6.8 Hz), 7.83 (2H, s), 7.84 (1H, d, J=9.5 Hz), 8.19 (1H, d, J=9.6 Hz).

IR (Nujol, cm$^{-1}$): 3323, 3179, 1662, 1550, 1466, 1360, 1325, 1173.

Reference Example 15

Synthesis of 2-chloro-6-(2-chloroethenyl)imidazo[1,2-b]pyridazin-3-ylsulfonamide

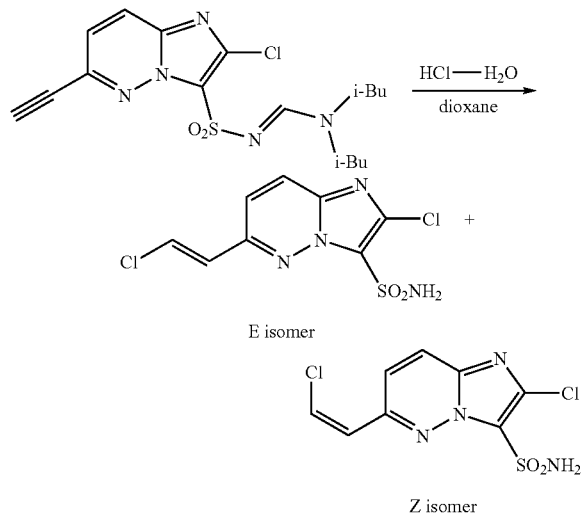

E isomer

Z isomer

The reaction was carried out in the same manner as in Reference Example 12 except that N'-(2-chloro-6-ethynylimidazo[1,2-b]pyridazin-3-ylsulfonyl)-N,N-diisobutylformamidine was used in place of N'-(2-chloro-6-cyclopropylimidazo[1,2-b]pyridazin-3-ylsulfonyl)-N,N-diisobutylformamidine. The resulting crystals were purified by silica gel column chromatography (ethyl acetate:hexane=1:1), to give E and Z isomers of the title compound as white crystals. The yield of the E isomer was 7.5%, and the yield of the Z isomer was 72.4%. Physical values of the E isomer:

mp>240° C. (decomp)

$^1$H NMR (DMSO-d$_6$, δ): 7.37 (1H, d, J=13.8 Hz), 7.82 (1H, d, J=9.6 Hz), 7.91 (1H, d, J=13.8 Hz), 7.93 (2H, brs), 8.29 (1H, d, J=9.6 Hz).

IR (Nujol, cm$^{-1}$): 3329, 3182, 1616, 1467, 1361, 1324, 1169, 945.

Physical Values of the Z Isomer:

mp 197.0-200.0° C.

$^1$H NMR (DMSO-d$_6$, δ): 7.14 (1H, d, J=8.3 Hz), 7.20 (1H, d, J=8.3 Hz), 7.83 (2H, brs), 8.06 (1H, d, J=9.6 Hz), 8.33 (1H, d, J=9.6 Hz).

IR (Nujol, cm$^{-1}$): 3370, 3260, 1632, 1465, 1364, 1308, 1187, 1164, 842.

Reference Example 16

Synthesis of 2-chloro-6-ethynylimidazo[1,2-b]pyridazin-3-ylsulfonamide

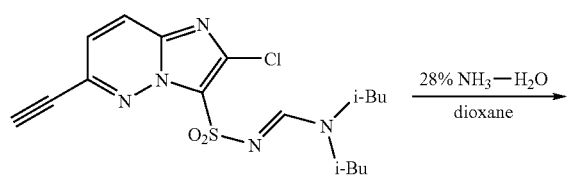

N'-(2-Chloro-6-ethynylimidazo[1,2-b]pyridazin-3-ylsulfonyl)-N,N-diisobutylformamidine (792 mg, 2.00 mmol) was suspended in dioxane (10.0 mL), and 28% ammonia water (4.00 g, 65.8 mmol) was added dropwise to the suspension under stirring at room temperature. The mixture was stirred at room temperature for 3 days, then concentrated to remove ammonia, and adjusted to pH 1 with conc. hydrochloric acid. The reaction solution was diluted with water and extracted with ethyl acetate, and the extract was dehydrated over anhydrous magnesium sulfate and concentrated under reduced pressure. The residues were purified by silica gel column chromatography (ethyl acetate:hexane=1:1) to give the title compound as pale yellow crystals. The yield was 71 mg (13.8%).

mp>234° C. (dec.)

$^1$H NMR (DMSO-d$_6$, δ): 4.92 (1H, s), 7.69 (1H, d, J=9.4 Hz), 8.02 (2H, brs), 8.32 (1H, d, J=9.4 Hz).

IR (Nujol, cm$^{-1}$): 3359, 3294, 3242, 2123, 1464, 1356, 1312, 1170.

Reference Example 17

Synthesis of 2-chloro-6-n-propylimidazo[1,2-b]pyridazine

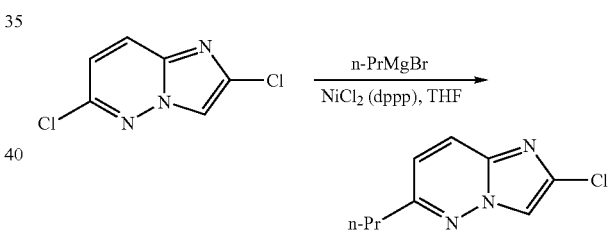

2,6-Dichloroimidazo[1,2-b]pyridazine (10.0 g, 53.2 mmol) and [1,3-bis(diphenylphosphino)propane]nickel (II) dichloride (0.43 g, 0.80 mmol) were added to tetrahydrofuran (80.0 ml) under a nitrogen stream, and a solution of n-propylmagnesium bromide in tetrahydrofuran (2 M, 31.9 ml, 63.8 mmol) was added dropwise over 60 minutes to the mixture under ice-cooling. The mixture was stirred for 10 minutes under ice-cooling, and the reaction mixture was warmed to room temperature and stirred for 2 hours at room temperature. Cold water (700 ml) was added to the reaction mixture which was then acidified with conc. hydrochloric acid, and the precipitated solids were collected by filtration, and the insoluble solids were washed with dilute hydrochloric acid and then with water. On one hand, the filtrate was extracted with ethyl acetate, and the extracts were combined and washed with dilute hydrochloric acid, a saturated saline solution, an aqueous saturated sodium bicarbonate solution and a saturated saline solution in this order. The resulting organic layer was dried over anhydrous magnesium sulfate, filtrated and concentrated. The concentrated residues and the solids collected by filtration were purified by silica gel column chromatography (ethyl acetate:hexane=3:7), to give the title compound as white crystals. The yield was 9.21 g (88.5%).

mp 73.9-80.0° C.

$^1$H NMR (CDCl$_3$, δ): 1.01 (3H, t, J=7.4 Hz), 1.78 (2H, m), 2.79 (2H, t, J=7.6 Hz), 6.96 (1H, d, J=9.3 Hz), 7.75 (1H, d, J=9.3 Hz), 7.80 (1H, s).

IR (Nujol, cm$^{-1}$): 3122, 1466, 1377, 1314, 1302.

Reference Example 18

Synthesis of 2-chloro-6-isobutylimidazo[1,2-b]pyridazine

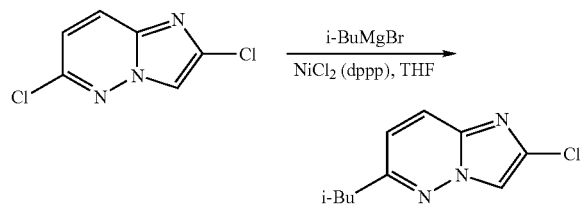

The reaction was carried out in the same manner as in Reference Example 17 except that a solution of isobutylmagnesium bromide in tetrahydrofuran was used in place of the solution of n-propylmagnesium bromide in tetrahydrofuran. The resulting crude product was purified by silica gel column chromatography (ethyl acetate:hexane=1:4), to give the title compound as pale yellow crystals. The yield was 1.27 g (60.6%).

mp 71.0-72.5° C.

$^1$H NMR (CDCl$_3$, δ): 0.98 (6H, d, J=6.6 Hz), 2.09 (1H, m), 2.68 (2H, d, J=7.3 Hz), 6.94 (1H, d, J=9.3 Hz), 7.75 (1H, d, J=9.3 Hz), 7.81 (1H, s).

IR (Nujol, cm$^{-1}$): 3126, 3059, 1545, 1466, 1369, 1331, 1320, 1279, 803.

Reference Example 19

Synthesis of 2-chloro-6-isobutylimidazo[1,2-b]pyridazin-3-ylsulfonamide

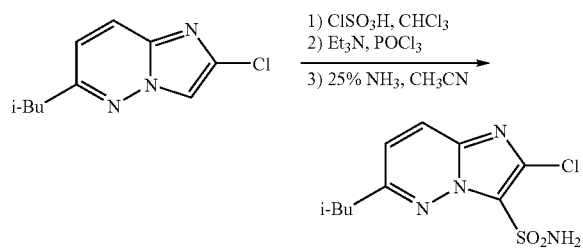

The reaction was carried out in the same manner as in Reference Example 6 except that 2-chloro-6-isobutylimidazo[1,2-b]pyridazine was used in place of 2-chloro-6-n-butylimidazo[1,2-b]pyridazine. The resulting reaction mixture was purified by silica gel column chromatography (ethyl acetate:hexane=1:1), to give the title compound as white crystals. The yield was 1.12 g (64.0%).

mp 168.0-169.5° C.

$^1$H NMR (DMSO-d$_6$, δ): 0.93 (6H, d, J=6.6 Hz), 2.14 (1H, m), 2.82 (2H, d, J=7.4 Hz), 7.51 (1H, d, J=9.4 Hz), 7.80 (2H, s), 8.19 (1H, d, J=9.4 Hz).

IR (Nujol, cm$^{-1}$): 3316, 3180, 3117, 1548, 1469, 1362, 1336, 1321, 1200, 1173, 849, 678.

Reference Example 20

Synthesis of 2-chloro-6-n-propylimidazo[1,2-b]pyridazin-3-ylsulfonyl chloride

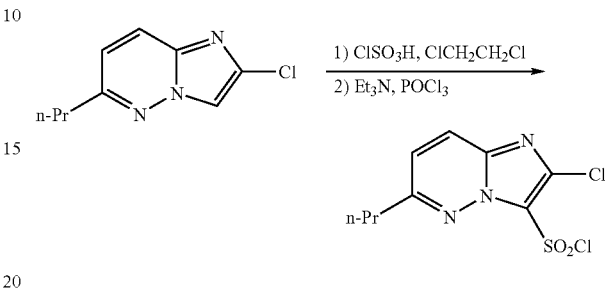

2-Chloro-6-n-propylimidazo[1,2-b]pyridazine (5.00 g, 25.6 mmol) was dissolved in 1,2-dichloroethane (30.0 ml), and chlorosulfonic acid (3.40 ml, 51.1 mmol) was added to the solution at room temperature. The mixture was heated for 8.5 hours under reflux, and then cooled to room temperature, and triethylamine (7.84 ml, 56.2 mmol) and phosphorus oxychloride (5.24 ml, 56.2 mmol) were added thereto and heated for 4 hours under reflux. Cold water was added to the reaction mixture which was then extracted with chloroform. The extracts were combined, dried over anhydrous magnesium sulfate, filtered and concentrated. The concentrated residues were purified by silica gel column chromatography (ethyl acetate:hexane=3:7) to give the title compound as pale yellow crystals. The yield was 7.40 g (98.4%).

mp 94.2-95.5° C.

$^1$H NMR (CDCl$_3$, δ): 1.06 (3H, t, J=7.4 Hz), 1.88 (2H, m), 2.99 (2H, t, J=7.6 Hz), 7.36 (1H, d, J=9.4 Hz), 7.95 (1H, d, J=9.4 Hz).

IR (Nujol, cm$^{-1}$): 1464, 1436, 1386, 1314, 1166, 620, 573, 562, 550.

Reference Example 21

Synthesis of 2-fluoro-6-n-propylimidazo[1,2-b]pyridazin-3-ylsulfonyl fluoride

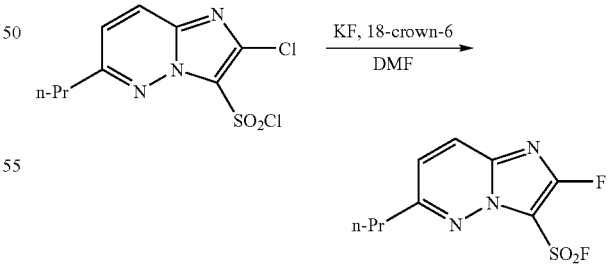

Dry potassium fluoride (7.30 g, 130 mmol), 18-crown-6 (1.33 g, 5.03 mmol) and 2-chloro-6-n-propylimidazo[1,2-b]pyridazin-3-ylsulfonyl chloride (7.40 g, 25.2 mmol) were heated in DMF (100 ml) for 3 hours under reflux and then left overnight at room temperature. The reaction mixture was concentrated under reduced pressure, and cold water was added to the concentrated residues which were then extracted with chloroform. The extracts were combined, dried over anhydrous magnesium sulfate, filtered and concentrated. The concentrated residues were purified by silica gel column chromatography (ethyl acetate:hexane=3:7), to give 5.28 g mixture containing the unreacted starting material. Hence, dry potassium fluoride (7.30 g, 130 mmol), 18-crown-6 (1.22 g, 4.61 mmol) and 5.28 g of the reaction mixture were heated in DMF (50.0 ml) for 5 hours under reflux and then stirred at 150° C. overnight. The reaction mixture was cooled, concentrated under reduced pressure, and cold water was added to the concentrated residues which were then extracted with chloroform. The extracts were combined, dried over anhydrous magnesium sulfate, filtered and concentrated, and the concentrated residues were purified by silica gel column chromatography (ethyl acetate:hexane=3:7), to give the title compound as white crystals. The yield was 2.02 g (30.7%).

$^1$H NMR (CDCl$_3$, δ): 1.05 (3H, t, J=7.3 Hz), 1.85 (2H, m), 2.95 (2H, t, J=7.7 Hz), 7.37 (1H, d, J=9.4 Hz), 7.93 (1H, d, J=9.4 Hz).

IR (Nujol, cm$^{-1}$): 1538, 1434, 1310, 1240, 1220, 1188, 799, 765, 695, 613, 595.

Reference Example 22

Synthesis of 2-fluoro-6-n-propylimidazo[1,2-b]pyridazin-3-ylsulfonamide

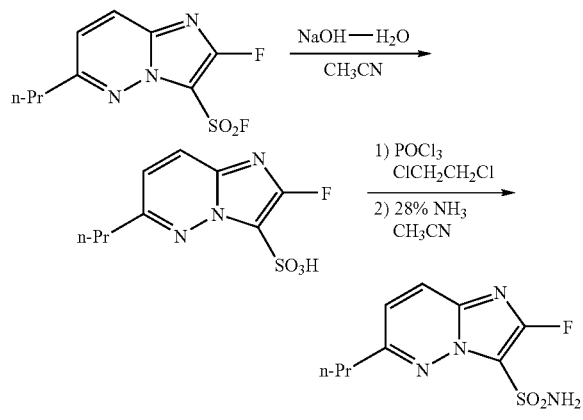

(a) 2-Fluoro-6-n-propylimidazo[1,2-b]pyridazin-3-ylsulfonyl fluoride (1.00 g, 3.83 mmol) was diluted with acetonitrile (20.0 ml), and a solution of sodium hydroxide (0.23 g, 5.75 mmol) in water (8.0 ml) was added thereto and stirred at room temperature for 4 hours. Because the reaction was not completed, additional sodium hydroxide (0.08 g, 2.00 mmol) was added, and the mixture was stirred at room temperature for 1 hour. The reaction mixture was concentrated under reduced pressure, and water was added to the concentrated residue which was then acidified with conc. hydrochloric acid. Acetone was added to the concentrated residue, and the insoluble solids were removed by filtration, and the filtrate was concentrated under reduced pressure to give 1.18 g yellowish brown oily matter containing 2-fluoro-6-n-propylimidazo[1,2-b]pyridazin-3-ylsulfonic acid.

(b) The oily matter (1.18 g) containing 2-fluoro-6-n-propylimidazo[1,2-b]pyridazin-3-ylsulfonic acid was dissolved in 1,2-dichloroethane (5.0 ml), and phosphorus oxychloride (0.70 ml, 7.66 mmol) was added thereto at room temperature, and the mixture was heated for 4 hours under reflux. Because the reaction was not completed, additional phosphorus oxychloride (0.70 ml, 7.66 mmol) was added thereto, and the mixture was heated for 2 hours under reflux. The reaction mixture was cooled, and cold water was added to the reaction mixture which was then extracted with chloroform. The extracts were combined, dried over anhydrous magnesium sulfate, filtered and concentrated. The concentrated residue was diluted with acetonitrile (2.0 ml), added dropwise to a solution of 28% ammonia water (8.0 ml) in acetonitrile (5.0 ml) under ice-cooling and stirred for 3 hours at room temperature. The reaction mixture was diluted with water and then acidified by dropwise addition of conc. hydrochloric acid. The precipitated solids were collected by filtration and washed with water, and the solids were purified by silica gel column chromatography (acetone:chloroform=2:5), to give the title compound as pale yellowish white crystals. The yield was 0.33% (33.4%).

mp 147.8-148.0° C.

$^1$H NMR (DMSO-d$_6$, δ): 0.97 (3H, t, J=7.4 Hz), 1.76 (2H, m), 2.89 (2H, t, J=7.7 Hz), 7.56 (1H, d, J=9.4 Hz), 7.84 (2H, s), 8.19 (1H, d, J=9.4 Hz).

IR (Nujol, cm$^{-1}$): 3318, 1540, 1465, 1412, 1351, 1305, 1170, 609.

$^{19}$F NMR (DMSO-d$_6$, δ): −114.3

Reference Example 23

Synthesis of 2-ethylthio-6-n-propylimidazo[1,2-b]pyridazin-3-ylsulfonamide

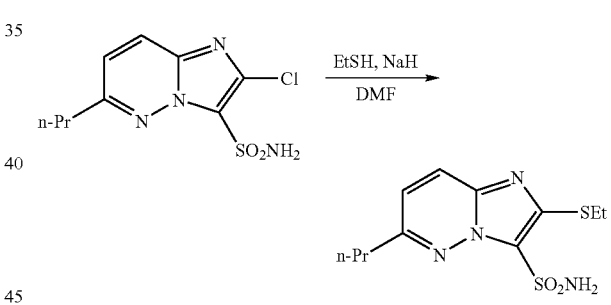

Sodium hydride (60%, 0.73 g, 18.2 mmol) was suspended in DMF (10.0 ml) under ice-cooling, and ethanethiol (1.35 ml, 18.2 mmol) was added dropwise thereto, and the mixture was stirred at 0° C. for 2 hours. 2-Chloro-6-propylimidazo[1,2-b]pyridazin-3-ylsulfonamide (1.00 g, 3.64 mmol) was added thereto and heated at 110° C. for 2.5 hours under stirring. The reaction mixture was left, cooled, diluted with water and acidified by dropwise addition of conc. hydrochloric acid. The precipitated solids were collected by filtration and washed with water, and the solids were suspended in a mixed solvent of chloroform and ethyl acetate, and the insoluble solids were collected by filtration, and the solids were washed with chloroform to give the title compound as gray crystals. The yield was 0.45 g (41.2%).

mp 175.9-177.2° C.

$^1$H NMR (DMSO-d$_6$, δ): 0.95 (3H, t, J=7.4 Hz), 1.34 (3H, t, J=7.3 Hz), 1.75 (2H, m), 2.87 (2H, t, J=7.7 Hz), 3.19 (2H, q, J=7.3 Hz), 7.41 (1H, d, J=9.3 Hz), 7.56 (2H, s), 8.12 (1H, d, J=9.3 Hz).

IR (Nujol, cm$^{-1}$): 3309, 3188, 3059, 1466, 1430, 1348, 1325, 1165, 599.

Reference Example 24

Synthesis of 2-ethylsulfonyl-6-n-propylimidazo[1,2-b]pyridazin-3-ylsulfonamide

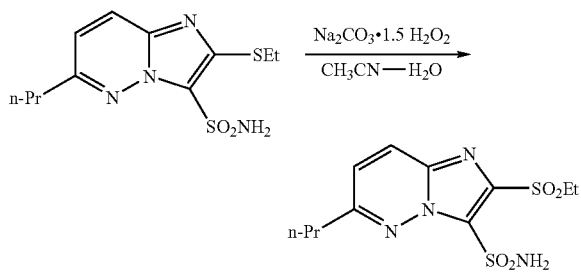

2-Ethylthio-6-n-propylimidazo[1,2-b]pyridazin-3-ylsulfonamide (0.30 g, 1.00 mmol) was suspended in acetonitrile (1.0 ml) and water (4.0 ml), and sodium percarbonate (effective oxygen concentration, 12.2%; 0.33 g; 2.50 mmol) was added thereto at 45° C. and stirred at 50 to 60° C. for 2.5 hours. The reaction mixture was poured into water and acidified with dilute hydrochloric acid, and the precipitated insoluble solids were collected by filtration and washed with water, to give the title compound as white crystals. The yield was 0.25 g (75.3%).

mp 232.3-233.0° C.

$^1$H NMR (DMSO-d$_6$, δ): 0.97 (3H, t, J=7.3 Hz), 1.21 (3H, t, J=7.3 Hz), 1.78 (2H, m), 2.96 (2H, t, J=7.7 Hz), 3.62 (2H, q, J=7.3 Hz), 7.62 (1H, d, J=9.4 Hz), 7.96 (2H, s), 8.37 (1H, d, J=9.4 Hz).

IR (Nujol, cm$^{-1}$): 3354, 3269, 1464, 1351, 1318, 1166, 1137, 743, 711, 452.

Reference Example 25

Synthesis of ethyl 6-n-propylimidazo[1,2-b]pyridazin-2-ylcarboxylate

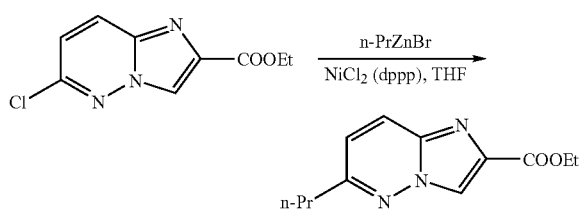

Ethyl 6-chloroimidazo[1,2-b]pyridazin-2-ylcarboxylate (1.00 g, 4.43 mmol) and [1,3-bis(diphenylphosphino)propane]nickel (II) dichloride (0.24 g, 0.44 mmol) were added to tetrahydrofuran (8.0 ml) under a nitrogen stream, and a solution of n-propylzinc bromide in tetrahydrofuran (0.5 M, 13.3 ml, 6.65 mmol) was added dropwise thereto with stirring under ice-cooling. The mixture was stirred for 20 minutes under ice-cooling and for 0.5 hour at room temperature, and cold water (50.0 ml) was added to the reaction mixture which was then acidified with dilute hydrochloric acid. The reaction solution was extracted with ethyl acetate, and the extracts were combined and washed with dilute hydrochloric acid and a saturated saline solution. The resulting organic layer was dried over anhydrous magnesium sulfate, filtered and concentrated. The concentrated residue was purified by silica gel column chromatography (acetone:hexane=1:3) to give the title compound as white crystals. The yield was 0.77 g (74.8%).

mp 54.0-54.5° C.

$^1$H NMR (CDCl$_3$, δ): 1.02 (3H, t, J=7.4 Hz), 1.44 (3H, t, J=7.1 Hz), 1.80 (2H, m), 2.81 (2H, t, J=7.6 Hz), 4.47 (2H, q, J=7.1 Hz), 7.00 (1H, d, J=9.5 Hz), 7.90 (1H, d, J=9.5 Hz), 8.43 (1H, s).

IR (Nujol, cm$^{-1}$): 3121, 1716, 1541, 1306, 1238, 1228, 1195.

Reference Example 26

Synthesis of 6-n-propylimidazo[1,2-b]pyridazin-2-ylcarboxyamide

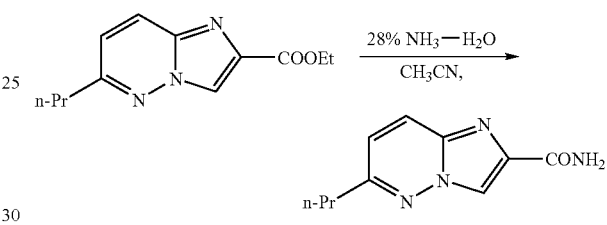

sealed in a tube

Ethyl 6-n-propylimidazo[1,2-b]pyridazin-2-ylcarboxylate (4.90 g, 21.0 mmol) was diluted with acetonitrile (7.0 ml), and 28% ammonia water (10.0 ml) was added thereto and stirred at 100° C. for 7 hours in a sealed tube. The reaction mixture was cooled to room temperature and diluted with water (20.0 ml), and the insoluble solids were collected by filtration and washed with water to give the title compound as white crystals. The yield was 3.39 g (79.0%).

mp 223.5-224.2° C.

$^1$H NMR (CDCl$_3$, δ): 1.02 (3H, t, J=7.4 Hz), 1.79 (2H, m), 2.81 (2H, t, J=7.6 Hz), 5.64 (1H, brs), 7.01 (1H, d, J=9.4 Hz), 7.21 (1H, brs), 7.81 (1H, d, J=9.4 Hz), 8.43 (1H, s).

IR (Nujol, cm$^{-1}$): 3437, 3175, 3104, 1632, 1542, 1319, 1294, 812, 682.

Reference Example 27

Synthesis of 6-n-propylimidazo[1,2-b]pyridazin-2-ylcarbonitrile

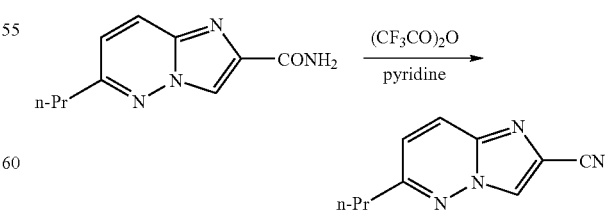

6-n-Propylimidazo[1,2-b]pyridazin-2-ylcarboxyamide (3.38 g, 16.5 mmol) was dissolved in pyridine (10.0 ml), and trifluoroacetic anhydride (3.51 ml, 24.8 mmol) was added to the solution with stirring under ice-cooling, and the mixture was stirred for 0.5 hour under ice-cooling and for 0.5 hour at room temperature. The reaction mixture was acidified by adding water and conc. hydrochloric acid, and the insoluble solids were separated by filtration into solids and an aqueous solution. The solids were suspended in ether and stirred, and insolubles were removed, whereby an ether extract was obtained. The aqueous solution was saturated with sodium chloride and then extracted with ethyl acetate to give an ethyl acetate extract. The ether extract and ethyl acetate extract were concentrated and purified by silica gel column chromatography (ethyl acetate:chloroform=2:5) to give the title compound as white crystals. The yield was 2.41 g (78.2%).

mp 81.8-82.4° C.

$^1$H NMR (CDCl$_3$, δ): 1.02 (3H, t, J=7.4 Hz), 1.80 (2H, m), 2.83 (2H, t, J=7.6 Hz), 7.08 (1H, d, J=9.4 Hz), 7.88 (1H, d, J=9.4 Hz), 8.30 (1H, s).

IR (Nujol, cm$^{-1}$): 3108, 2235, 1544, 1466, 1326, 1292, 1132, 984, 818.

Reference Example 28

Synthesis of 2-cyano-6-n-propylimidazo[1,2-b]pyridazin-3-ylsulfonamide

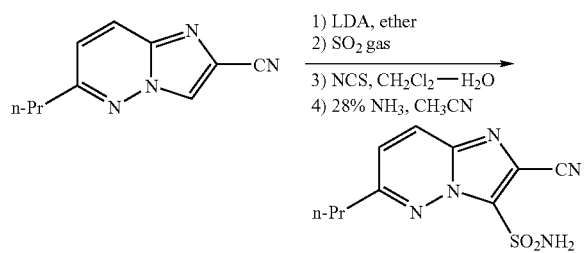

A solution of lithium diisopropylamide in heptane-tetrahydrofuran-ethyl benzene (2.0 M, 3.22 ml, 6.44 mmol) was diluted with ether (30.0 ml), and a solution of 6-n-propylimidazo[1,2-b]pyridazin-2-ylcarbonitrile (1.00 g, 5.37 mmol) in ether (20.0 ml) was added dropwise thereto over 12 minutes at −60° C. or less, and the mixture was stirred at −60° C. for 1.5 hours. The unreacted starting material remained without being dissolved, so tetrahydrofuran (20.0 ml) was added thereto and stirred at −60° C. for 1.5 hours. A sulfur dioxide gas generated from sodium hydrogen sulfite and conc. sulfuric acid was introduced thereinto at −60° C. or less over 0.5 hour and stirred at −60° C. or less for 20 minutes, and thereafter, the temperature of the mixture was increased gradually to 0° C. The precipitated solids were collected by filtration, and the solids were washed with ether. The resulting solids were added to a solution of N-chlorosuccinimide (1.15 g, 8.59 mmol) in dichloromethane (20.0 ml) and water (20.0 ml) and stirred for 1 hour under ice-cooling. The organic layer was separated, and the aqueous layer was extracted with chloroform. The organic layers were combined, dried over anhydrous magnesium sulfate and filtered, and the filtrate was concentrated. The concentrated residue was diluted with acetonitrile (10.0 ml), and 28% ammonia water (2.0 ml) was added thereto under ice-cooling and stirred at the same temperature for 0.5 hour. The reaction mixture was concentrated, then water was added thereto, insoluble solids were collected by filtration, and the solids were washed with water. The resulting solids were washed with chloroform to give the title compound as white crystals. The yield was 0.20 g (14.0%).

mp 237.4-243.8° C.

$^1$H NMR (DMSO-d$_6$, δ): 0.97 (3H, t, J=7.3 Hz), 1.78 (2H, m), 2.82 (2H, t, J=7.7 Hz), 7.64 (1H, d, J=9.6 Hz), 8.20 (2H, brs), 8.33 (1H, d, J=9.6 Hz)

IR (Nujol, cm$^{-1}$): 3316, 3185, 2243, 1550, 1464, 1361, 1175, 606.

Reference Example 29

Synthesis of 3-chloro-6-isopropylpyridazine

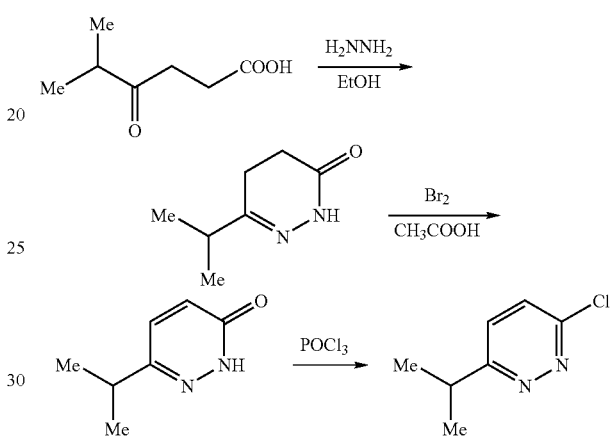

(a) 5-Methyl-4-oxohexanoic acid (3.60 g, 25.0 mmol) and anhydrous hydrazine (0.80 g, 26.0 mmol) were heated for 3 hours in ethanol (36.0 ml) under stirring. After the reaction solution was concentrated under reduced pressure, hexane was added to the residues to precipitate crystals, and the crystals were collected by filtration to give 4,5-dihydro-6-isopropyl-3 (2H)-pyridazinone as crystals. The yield was 3.10 g.

(b) 4,5-Dihydro-6-isopropyl-3 (2H)-pyridazinone (3.10 g) was dissolved in acetic acid (30.0 ml), and bromine (3.50 g, 22.0 mmol) was added dropwise to the solution over 10 minutes under heating at 100° C. with stirring. After the reaction solution was heated for 1 hour under reflux, the acetic acid was distilled away under reduced pressure, and water (100 ml) was added to the residues which were then extracted 5 times with ethyl acetate. The extracts were combined, dried over anhydrous magnesium sulfate and concentrated to give a crude product of 6-isopropyl-3 (2H)-pyridazinone. The yield was 3.30 g.

(c) 6-Isopropyl-3 (2H)-pyridazinone (3.30 g) and phosphorus oxychloride (15.0 ml) were heated for 1 hour under reflux. After an excess of phosphorus oxychloride was distilled away, ice-water (200 ml) was added to the residues which were then adjusted to pH 6 with 20% aqueous sodium hydroxide solution. The reaction solution was extracted 3 times with ethyl acetate, and the extracts were combined, dried over anhydrous magnesium sulfate and concentrated. The residues were purified by silica gel column chromatography (ethyl acetate:chloroform=1:2) to give the title compound as pale red crystals. The yield was 1.60 g (40.8% based on 5-methyl-4-oxohexanoic acid). mp 32-33° C.

$^1$H NMR (CDCl$_3$, δ) 1.35-1.40 (6H, m), 3.33 (1H, sept, J=7.0 Hz), 7.34 (1H, d, J=8.8 Hz), 7.44 (1H, d, J=8.8 Hz).

Reference Example 30

Synthesis of 3-amino-6-isopropylpyridazine

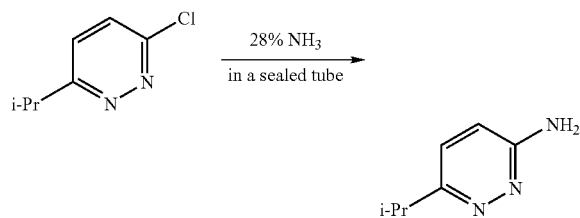

3-Chloro-6-isopropylpyridazine (1.60 g, 10.2 mmol) and 28% ammonia water (15.0 ml) were introduced into a sealed tube reactor and stirred under pressure and heating at 140° C. for 24 hours and at 165° C. for 25 hours. The reaction solution was left and cooled, poured into water (30.0 ml), adjusted to pH 9, and extracted 3 times with ethyl acetate. The extracts were combined, dried over anhydrous sodium sulfate, and concentrated under reduced pressure to give crude crystals. The crystals, while being washed with diisopropyl ether-hexane, were filtered to give the title compound as pale brown crystals. The yield was 0.41 g (29.3%).

mp 131-132° C.

$^1$H NMR (CDCl$_3$, δ): 1.30 (6H, d, J=7.0 Hz), 3.17 (1H, sept, J=7.0 Hz), 4.69 (2H, brs), 6.72 (1H, d, J=9.1 Hz), 7.12 (1H, d, J=9.1 Hz).

IR (Nujol, cm$^{-1}$): 3312, 3139, 1645, 1608, 1555, 1056, 850, 840, 651.

Reference Example 31

Synthesis of 6-isopropyl-2-methylimidazo[1,2-b]pyridazine

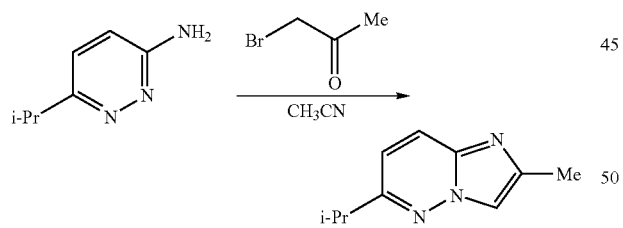

3-Amino-6-isopropylpyridazine (0.41 g, 2.99 mmol) and bromoacetone (0.53 g, 3.10 mmol) were mixed with acetonitrile (5.0 ml) and heated for 6 hours under reflux. After the reaction was completed, water (20.0 ml) was poured into the reaction solution and adjusted to pH 9 with 20% aqueous sodium hydroxide solution. The reaction solution was extracted twice with ethyl acetate, and the extracts were combined, dried over anhydrous sodium sulfate and concentrated. The residues were purified by silica gel column chromatography (ethyl acetate:chloroform=1:1) to give the title compound as brown oil. The yield was 0.30 g (57.2%).

$^1$H NMR (CDCl$_3$, δ): 1.33 (6H, d, J=7.0 Hz), 2.48 (3H, d, J=0.8 Hz), 3.09 (1H, sept, J=7.0 Hz), 6.90 (1H, d, J=9.4 Hz), 7.65-7.67 (1H, m), 7.74 (1H, d, J=9.4 Hz).

IR (Neat, cm$^{-1}$): 1539, 1327, 1289, 1123, 1084, 1042, 989, 815, 727.

Reference Example 32

Synthesis of 6-isopropyl-2-methylimidazo[1,2-b]pyridazin-3-ylsulfonamide

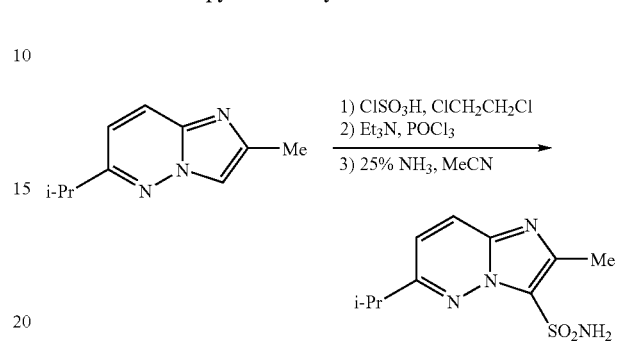

The title compound was obtained as pale brown crystals by the same reaction as in Reference Example 4 except that 6-isopropyl-2-methylimidazo[1,2-b]pyridazine was used in place of 2-chloro-6-n-propylimidazo[1,2-b]pyridazine. The yield was 27.6%.

mp 199-200° C.

$^1$H NMR (DMSO-d$_6$, δ): 1.32 (6H, d, J=6.9 Hz), 2.57 (3H, s), 3.2-3.4 (1H, m), 7.44 (2H, brs), 7.47 (1H, d, J=9.5 Hz), 8.11 (1H, d, J=9.5 Hz).

IR (Nujol, cm$^{-1}$): 3338, 3067, 1543, 1347, 1332, 1162, 1047, 828, 763, 740, 606.

Reference Example 33

Synthesis of 6-chloro-2-n-propylimidazo[1,2-b]pyridazine

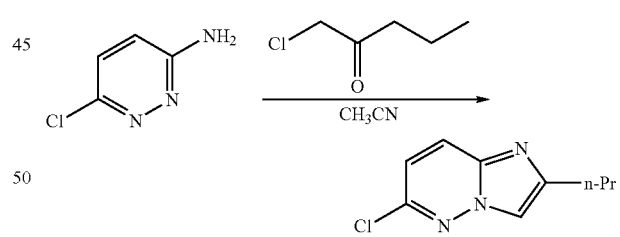

A crude product was obtained by the same reaction as in Reference Example 31 except that 3-amino-6-chloropyridazine was used in place of 3-amino-6-isopropylpyridazine, and 1-chloro-2-pentanone was used in place of bromoacetone. This product was purified by silica gel column chromatography (ethyl acetate:chloroform=1:2), to give the title compound as flesh-color crystals. The yield was 43.7%.

$^1$H NMR (CDCl$_3$, δ): 1.00 (3H, t, J=7.4 Hz), 1.7-1.9 (2H, m), 2.79 (2H, t, J=7.6 Hz), 6.99 (1H, d, J=9.4 Hz), 7.71 (1H, s), 7.80 (1H, d, J=9.4 Hz).

IR (Nujol, cm$^{-1}$): 1608, 1518, 1455, 1328, 1286, 1133, 1091, 987, 940, 818, 764, 708, 603, 508.

Reference Example 34

Synthesis of 6-chloro-2-n-propylimidazo[1,2-b]pyridazin-3-ylsulfonamide

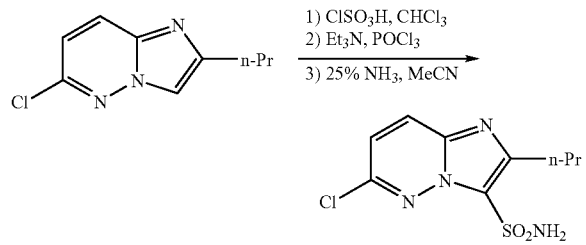

The title compound was obtained as white crystals in the same manner as in Reference Example 6 except that 6-chloro-2-n-propylimidazo[1,2-b]pyridazine was used in place of 2-chloro-6-n-butylimidazo[1,2-b]pyridazine. The yield was 45.1%.

mp 155-156° C. (dec.)

$^1$H NMR (DMSO-d$_6$, δ): 0.94 (3H, t, J=7.3 Hz), 1.7-1.8 (2H, m), 2.98 (2H, t, J=7.4 Hz), 7.59 (1H, d, J=9.5 Hz), 7.75 (2H, brs), 8.30 (1H, d, J=9.5 Hz).

IR (Nujol, cm$^{-1}$): 3404, 3259, 1524, 1359, 1298, 1180, 1164, 1142, 818, 737, 612.

Reference Example 35

Synthesis of 2-chloro-6-isopropylimidazo[1,2-b]pyridazine

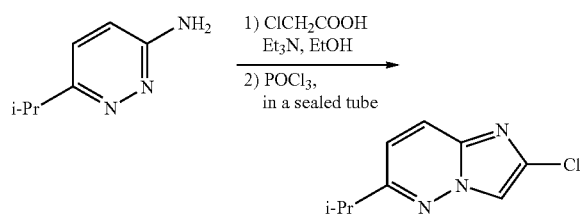

Chloroacetic acid (0.32 g, 3.3 mmol), triethylamine (0.33 g, 3.3 mmol), ethanol (5.0 ml) and water (5.0 ml) were mixed and 3-amino-6-isopropylpyridazine (0.45 g, 3.28 mmol) was added thereto with stirring at room temperature, and after the mixture was heated at 80 to 90° C. for 5 hours under stirring, the reaction solution was concentrated to dryness. The resulting solids and phosphorus oxychloride (5.0 ml) were stirred at 150° C. for 12 hours in a sealed tube reactor. The reaction solution was left and cooled to room temperature and poured into water (50.0 ml) of 40 to 50° C., to decompose an excess of phosphorus oxychloride. The reaction solution was adjusted to pH 7 with 20% aqueous sodium hydroxide solution and extracted 3 times with ethyl acetate, and the extracts were combined, dried over anhydrous magnesium sulfate and concentrated. The residues were purified by silica gel column chromatography (ethyl acetate:chloroform=1:2), to give the title compound as pale yellow crystals. The yield was 0.15 g (23.4%).

mp 69-71° C.

$^1$H NMR (CDCl$_3$, δ): 1.34 (6H, d, J=7.0 Hz), 3.11 (1H, sept, J=7.0 Hz), 6.99 (1H, d, J=9.4 Hz), 7.75-7.8 (2H, m).

IR (Nujol, cm$^{-1}$): 3128, 3050, 1545, 1347, 1327, 1306, 1275, 1257, 1192, 1140, 1088, 1044, 961.

Reference Example 36

Synthesis of 2-chloro-6-isopropylimidazo[1,2-b]pyridazin-3-ylsulfonamide

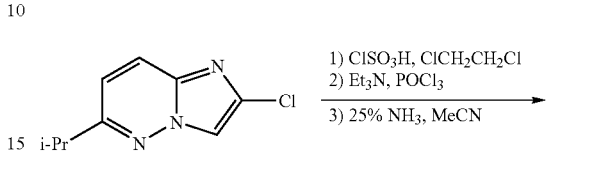

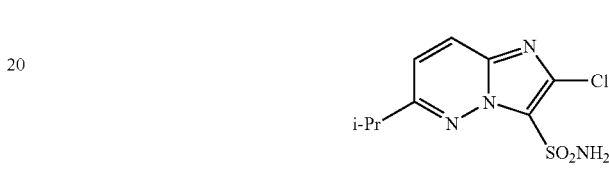

The title compound was obtained as pale brown crystals by the same reaction as in Reference Example 4 except that 2-chloro-6-isopropylimidazo[1,2-b]pyridazine was used in place of 2-chloro-6-n-propylimidazo[1,2-b]pyridazine. The yield was 28.5%.

mp 179-180° C. (dec.)

$^1$H NMR (DMSO-d$_6$, δ): 1.33 (6H, d, J=6.9 Hz), 3.28 (1H, sept, J=6.9 Hz), 7.61 (1H, d, J=9.5 Hz), 7.77 (2H, brs), 8.21 (1H, d, J=9.5 Hz).

IR (Nujol, cm$^{-1}$): 3347, 1549, 1460, 1379, 1366, 1357, 1331, 1317, 1254, 1174, 1166, 1069, 1036, 903, 826.

Reference Example 37

Synthesis of 2-chloro-6-ethylimidazo[1,2-b]pyridazine

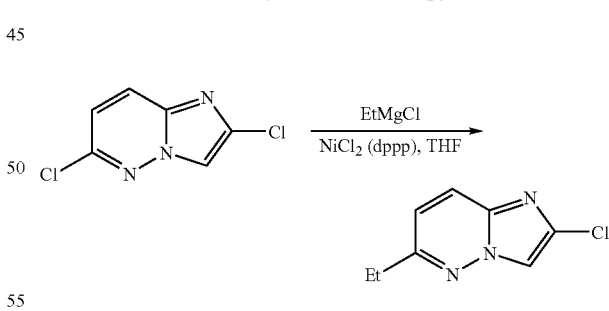

The title compound was obtained as pale yellow crystals by the same reaction as in Reference Example 3 except that a solution of ethylmagnesium chloride in tetrahydrofuran was used in place of the solution of propylmagnesium chloride in tetrahydrofuran. The yield was 66.2%.

$^1$H NMR (CDCl$_3$, δ): 1.35 (3H, t, J=7.6 Hz), 2.85 (2H, q, J=7.6 Hz), 6.97 (1H, d, J=9.3 Hz), 7.75 (1H, d, J=9.3 Hz), 7.80 (1H, s).

IR (Nujol, cm$^{-1}$): 3121, 3058, 1544, 1471, 1318, 1280, 1262, 1189, 1142, 1121, 1059, 983, 953, 822.

Reference Example 38

Synthesis of 2-chloro-6-ethylimidazo[1,2-b]pyridazin-3-ylsulfonamide

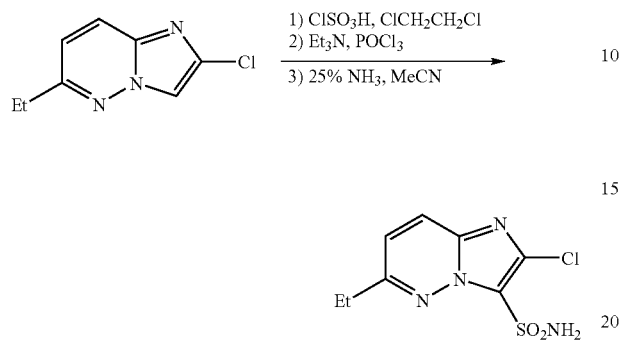

The title compound was obtained as pale brown crystals by the same reaction as in Reference Example 4 except that 2-chloro-6-ethylimidazo[1,2-b]pyridazine was used in place of 2-chloro-6-n-propylimidazo[1,2-b]pyridazine. The yield was 74.1%.

mp 204-205° C.

$^1$H NMR (DMSO-$d_6$, δ): 1.31 (3H, t, J=7.6 Hz), 2.95 (2H, q, J=7.6 Hz), 7.54 (1H, d, J=9.4 Hz), 7.82 (2H, brs), 8.19 (1H, d, J=9.4 Hz).

IR (Nujol, cm$^{-1}$): 3317, 3211, 1365, 1356, 1325, 1172, 829, 668.

Reference Example 39

Synthesis of 2-methyl-6-n-propylimidazo[1,2-b]pyridazine

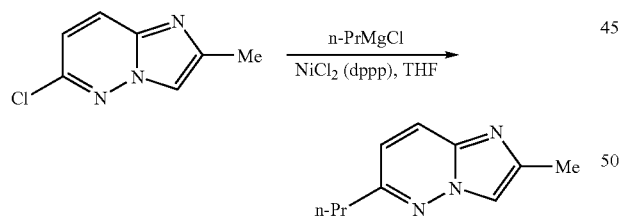

The title compound was obtained as pale reddish oil by the same reaction as in Reference Example 1 except that a solution of n-propylmagnesium chloride in ether was used in place of the solution of ethylmagnesium bromide in ether, and as the solvent, a tetrahydrofuran solvent was used in place of the mixed solvent of ether and tetrahydrofuran. The yield was 19.1%.

$^1$H NMR (CDCl$_3$, δ): 1.00 (3H, t, J=7.4 Hz), 1.7-1.9 (2H, m), 2.48 (3H, d, J=0.7 Hz), 2.77 (2H, t, J=7.5 Hz), 6.85 (1H, d, J=9.2 Hz), 7.66 (1H, d, J=0.7 Hz), 7.72 (1H, d, J=9.2 Hz).

IR (Nujol, cm$^{-1}$): 2961, 1541, 1464, 1326, 1296, 1153, 1124, 989, 816, 726.

Reference Example 40

Synthesis of 2-methyl-6-n-propylimidazo[1,2-b]pyridazin-3-ylsulfonamide

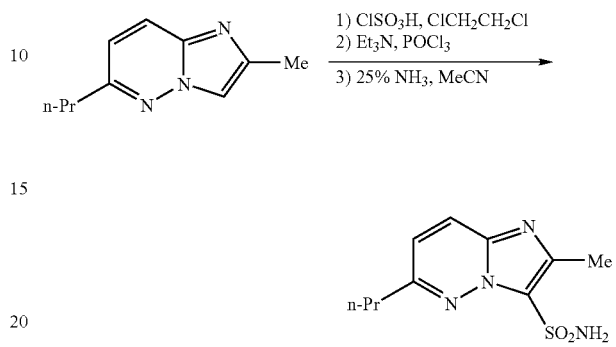

The title compound was obtained as pale brown crystals by the same reaction as in Reference Example 4 except that 2-methyl-6-n-propylimidazo[1,2-b]pyridazine was used in place of 2-chloro-6-n-propylimidazo[1,2-b]pyridazine. The yield was 14.6%.

mp 178-179° C. (dec.)

$^1$H NMR (DMSO-$d_6$, δ): 0.96 (3H, t, J=7.3 Hz), 1.7-1.9 (2H, m), 2.56 (3H, s), 2.8-2.9 (2H, m), 7.39 (1H, d, J=9.3 Hz), 7.46 (2H, brs), 8.08 (1H, d, J=9.3 Hz).

IR (Nujol, cm$^{-1}$): 3384, 3327, 1543, 1508, 1420, 1348, 1327, 1309, 1162, 827.

Reference Example 41

Synthesis of 6-chloro-2-ethylimidazo[1,2-b]pyridazin-3-ylsulfonamide

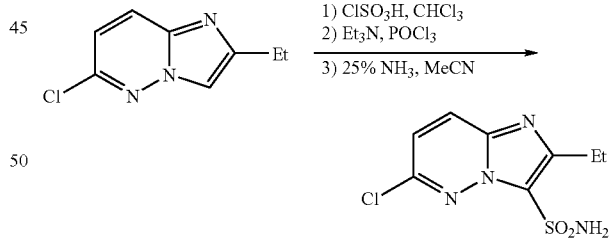

The title compound was obtained as white crystals by the same reaction as in Reference Example 6 except that 6-chloro-2-ethylimidazo[1,2-b]pyridazine was used in place of 2-chloro-6-n-butylimidazo[1,2-b]pyridazine. The yield was 11.5%.

mp 201-203° C.

$^1$H NMR (DMSO-$d_6$, δ): 1.27 (3H, t, J=7.5 Hz), 3.01 (2H, q, J=7.5 Hz), 7.59 (1H, d, J=9.5 Hz), 7.74 (2H, s), 8.30 (1H, d, J=9.5 Hz).

IR (Nujol, cm$^{-1}$): 3347, 1520, 1503, 1462, 1448, 1346, 1298, 1171, 1134, 1076, 819, 737.

Reference Example 42

Synthesis of 2-ethyl-6-ethylthioimidazo[1,2-b]pyridazin-3-ylsulfonamide

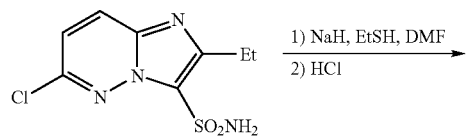

60% sodium hydride (0.19 g, 4.75 mmol) was suspended in DMF (5.0 ml) and ethanethiol (0.29 g, 4.6 mmol) was added thereto with stirring. After evolution of hydrogen was ceased, 6-chloro-2-ethylimidazo[1,2-b]pyridazin-3-ylsulfonamide (0.30 g, 1.15 mmol) was added thereto and stirred at 50° C. for 3 hours. After the reaction was completed, the reaction solution was poured into water (50.0 ml) and adjusted to pH 2 with dilute hydrochloric acid, and the precipitated crystals were filtered, washed with water and washed with ether, to give the title compound as pale yellow crystals. The yield was 0.19 g (57.3%).

mp 164-165° C.

$^1$H NMR (DMSO-d$_6$, δ): 1.26 (3H, t, J=7.5 Hz), 1.37 (3H, t, J=7.3 Hz), 2.98 (2H, q, J=7.5 Hz), 3.31 (2H, q, J=7.3 Hz), 7.31 (1H, d, J=9.5 Hz), 7.39 (2H, s), 8.01 (1H, d, J=9.5 Hz).

IR (Nujol, cm$^{-1}$): 3384, 1353, 1336, 1301, 1163.

Reference Example 43

Synthesis of 6-methylthio-2-n-propylimidazo[1,2-b]pyridazin-3-ylsulfonamide

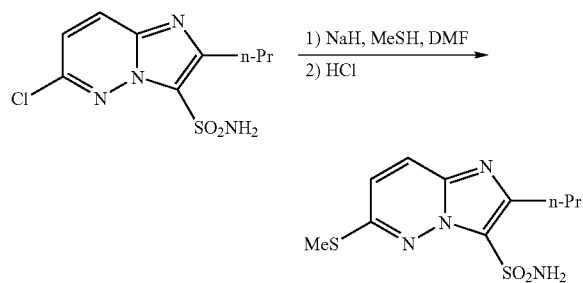

The title compound was obtained as pale yellow crystals by the same reaction as in Reference Example 42 except that 6-chloro-2-n-propylimidazo[1,2-b]pyridazin-3-ylsulfonamide was used in place of 6-chloro-2-ethylimidazo[1,2-b]pyridazin-3-ylsulfonamide, and methanethiol was used in place of ethanethiol. The yield was 73.3%.

mp 185-187° C.

$^1$H NMR (DMSO-d$_6$, δ): 0.93 (3H, t, J=7.4 Hz), 1.6-1.8 (2H, m), 2.67 (3H, s), 2.94 (2H, t, J=7.4 Hz), 7.36 (1H, d, J=9.5 Hz), 7.39 (2H, brs), 8.01 (1H, d, J=9.5 Hz).

IR (Nujol, cm$^{-1}$): 3378, 1536, 1446, 1307, 1171, 823, 616.

Reference Example 44

Synthesis of 6-ethoxy-2-n-propylimidazo[1,2-b]pyridazin-3-ylsulfonamide

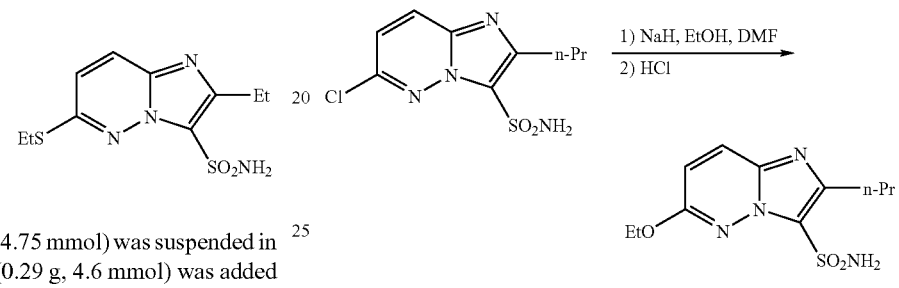

The title compound was obtained as pale yellow crystals by the same reaction as in Reference Example 42 except that 6-chloro-2-n-propylimidazo[1,2-b]pyridazin-3-ylsulfonamide was used in place of 6-chloro-2-ethylimidazo[1,2-b]pyridazin-3-ylsulfonamide, and ethanol was used in place of ethanethiol. The yield was 77.7%.

mp 170-176° C.

$^1$H NMR (DMSO-d$_6$, δ): 0.93 (3H, t, J=7.4 Hz), 1.39 (3H, t, J=7.0 Hz), 1.6-1.8 (2H, m), 2.91 (2H, t, J=7.4 Hz), 4.48 (2H, q, J=7.0 Hz), 7.06 (1H, d, J=9.7 Hz), 7.40 (2H, brs), 8.06 (1H, d, J=9.7 Hz).

IR (Nujol, cm$^{-1}$): 3351, 1551, 1504, 1346, 1166, 823, 629.

Reference Example 45

Synthesis of 6-dimethylamino-2-n-propylimidazo[1,2-b]pyridazin-3-ylsulfonamide

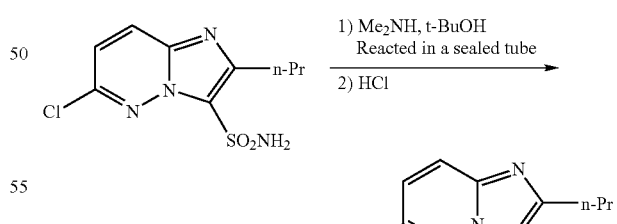

A mixture of 6-chloro-2-n-propylimidazo[1,2-b]pyridazin-3-ylsulfonamide (0.50 g, 1.81 mmol), 50% aqueous dimethylamine (1.0 ml) and t-butanol (5.0 ml) was heated at 100° C. for 8 hours with stirring in a sealed tube reactor. The reaction solution was left and cooled to room temperature, poured into water (50.0 ml) and adjusted to pH 6 with dilute hydrochloric acid, to precipitate crystals which were then filtered and washed with water, to give the title compound as pale yellow crystals. The yield was 0.38 g (74.0%).

mp 215-217° C.

$^1$H NMR (DMSO-d$_6$, δ): 0.92 (3H, t, J=7.3 Hz), 1.6-1.8 (2H, m), 2.87 (2H, t, J=7.4 Hz), 3.00 (6H, s), 7.13 (2H, brs), 7.20 (1H, d, J=10.0 Hz), 7.86 (1H, d, J=10.0 Hz).

IR (Nujol, cm$^{-1}$): 3340, 1565, 1501, 1345, 1318, 1163, 810, 623.

Reference Example 46

Synthesis of 6-chloro-2-trifluoromethylimidazo[1,2-b]pyridazin-3-ylsulfonamide

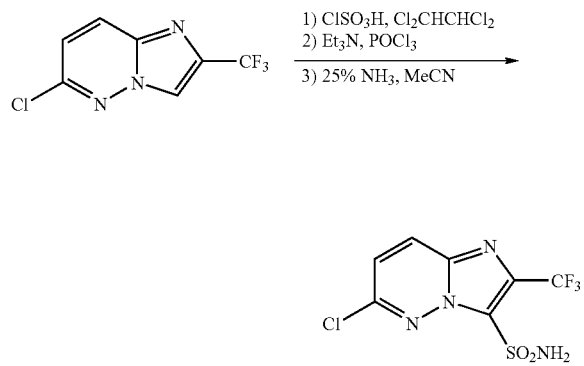

6-Chloro-2-trifluoromethylimidazo[1,2-b]pyridazine (6.00 g, 27.1 mmol) was dissolved in 1,1,2,2-tetrachloroethane (60.0 ml), and chlorosulfonic acid (97%, 2.80 ml, 40.7 mmol) was added to the solution with stirring at room temperature. The mixture was heated for 8 hours under reflux and then cooled to room temperature, and triethylamine (4.39 g, 43.4 mmol) and phosphorus oxychloride (7.47 g, 48.7 mmol) were added dropwise thereto. The reaction mixture was heated at 120° C. for 3 hours with stirring and then cooled to 50° C., and water (150 ml) was added thereto. After the reaction solution was partitioned, the aqueous layer was extracted twice with chloroform, and the organic layers were combined, washed twice with water, dried over anhydrous magnesium sulfate and concentrated under reduced pressure. The residues were dissolved in acetonitrile (100 ml) and stirred at room temperature, during which ammonia water (14 M, 9.00 ml, 126 mmol) was added thereto. The reaction solution was stirred at room temperature for 2 hours, poured into ice-water (400 ml) and adjusted to pH 2 with conc. hydrochloric acid, to precipitate crystals which were then filtered and washed with water. The crystals were dried and then purified by silica gel chromatography (ethyl acetate:chloroform=1:9→1:4→1:2), to give the title compound as colorless crystals. The yield was 3.80 g (46.6%).

mp 223.0-223.5° C.

$^1$H NMR (DMSO-d$_6$, δ): 7.77 (1H, d, J=9.6 Hz), 8.20 (2H, brs), 8.52 (1H, d, J=9.6 Hz).

$^{19}$F NMR (DMSO-d$_6$, δ): −58.48

IR (Nujol, cm$^{-1}$): 3177, 3104, 3089, 3069, 1568, 1530, 1452, 1385, 1371, 1361, 1307, 1243, 1173, 1157, 1133, 1119, 1041, 928, 840.

Reference Example 47

Synthesis of 6-ethylthio-2-trifluoromethylimidazo[1,2-b]pyridazin-3-ylsulfonamide

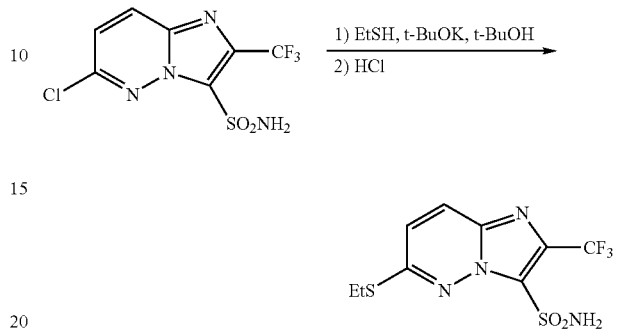

6-Chloro-2-trifluoromethylimidazo[1,2-b]pyridazin-3-ylsulfonamide (1.00 g, 3.33 mmol) was suspended in t-butyl alcohol (20.0 ml) and stirred at room temperature, during which potassium t-butoxide (80%, 1.40 g, 9.98 mmol) and ethanethiol (0.54 ml, 7.29 mmol) were added thereto. After the mixture was heated for 4 hours under reflux, the reaction solution was left and cooled to room temperature, poured into ice-water (200 ml) and adjusted to pH 3. The precipitated crystals were filtered and washed with water to give the title compound as colorless crystals. The yield was 0.54 g (50.0%).

mp 208-210° C.

$^1$H NMR (DMSO-d$_6$, δ): 1.38 (3H, t, J=7.3 Hz), 3.35 (2H, q, J=7.3 Hz), 7.48 (1H, d, J=9.6 Hz), 7.83 (2H, brs), 8.18 (1H, d, J=9.6 Hz).

$^{19}$F NMR (DMSO-d$_6$, δ): −58.22

IR (Nujol, cm$^{-1}$): 3368, 3198, 3100, 3061, 1598, 1540, 1532, 1455, 1375, 1360, 1320, 1210, 1182, 1162, 1130, 1112, 1038, 973, 916, 820.

Reference Example 48

Synthesis of 6-ethoxy-2-trifluoromethylimidazo[1,2-b]pyridazin-3-ylsulfonamide

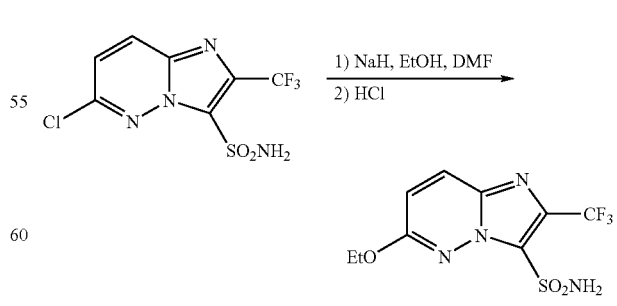

The title compound was obtained as pale yellow crystals by the same reaction as in Reference Example 42 except that 6-chloro-2-trifluoromethylimidazo[1,2-b]pyridazin-3-ylsulfonamide was used in place of 6-chloro-2-ethylimidazo[1,2-b]pyridazin-3-ylsulfonamide, and ethanol was used in place of ethanethiol. The yield was 83.1%.

mp 191-192° C.

$^1$H NMR (DMSO-d$_6$, δ): 1.41 (3H, t, J=7.0 Hz), 4.55 (2H, q, J=7.0 Hz), 7.25 (1H, d, J=9.8 Hz), 7.88 (2H, brs), 8.26 (1H, d, J=9.8 Hz).

$^{19}$F NMR (DMSO-d$_6$, δ): −58.17

IR (Nujol, cm$^{-1}$): 3370, 3266, 1618, 1558, 1522, 1493, 1473, 1388, 1371, 1324, 1315, 1296, 1234, 1203, 1180, 1165, 1147, 1122, 1041, 1024, 1003, 906, 828, 732.

Reference Example 49

Synthesis of 6-methylthio-2-trifluoromethylimidazo[1,2-b]pyridazin-3-ylsulfonamide

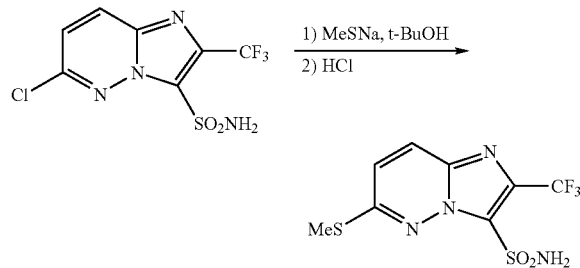

The title compound was obtained as colorless crystals by the same reaction as in Reference Example 47 except that an aqueous solution of methanethiol sodium salt was used in place of the combination of potassium t-butoxide and ethanethiol. The yield was 87.5%.

mp 272-273° C.

$^1$H NMR (DMSO-d$_6$, δ): 2.71 (3H, s), 7.53 (1H, d, J=9.6 Hz), 7.84 (2H, brs), 8.18 (1H, d, J=9.6 Hz).

$^{19}$F NMR (DMSO-d$_6$, δ): −58.25

IR (Nujol, cm$^{-1}$): 3356, 3260, 3095, 3029, 1557, 1538, 1523, 1449, 1372, 1360, 1307, 1206, 1182, 1168, 1144, 1115, 1037, 929, 823.

Reference Example 50

Synthesis of 2-ethyl-6-methylimidazo[1,2-b]pyridazine

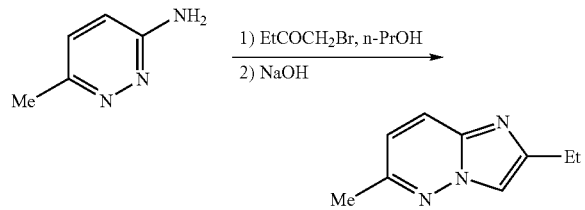

3-Amino-6-methylpyridazine (4.00 g, 27.5 mmol) and 1-bromo-2-butanone (90%, 7.38 g, 44.0 mmol) were heated in 1-propanol (40.0 ml) for 13 hours under reflux. The reaction solution was cooled to room temperature and concentrated under reduced pressure, and then the residues were dissolved in acetone (50.0 ml) and neutralized with 20% aqueous sodium hydroxide solution. The reaction solution was concentrated under reduced pressure, and then the residues were dissolved in chloroform, dried over anhydrous magnesium sulfate and concentrated. The residues were purified by silica gel column chromatography (isopropanol:hexane=1:2), to give the title compound as gray crystals. The yield was 2.33 g (39.4%).

mp 53-55° C.

$^1$H NMR (CDCl$_3$, δ): 1.35 (3H, t, J=7.5 Hz), 2.53 (3H, s), 2.84 (2H, q, J=7.5 Hz), 6.84 (1H, d, J=9.2 Hz), 7.65 (1H, s), 7.72 (1H, d, J=9.2 Hz).

Reference Example 51

Synthesis of 2-ethyl-6-methylimidazo[1,2-b]pyridazin-3-ylsulfonamide

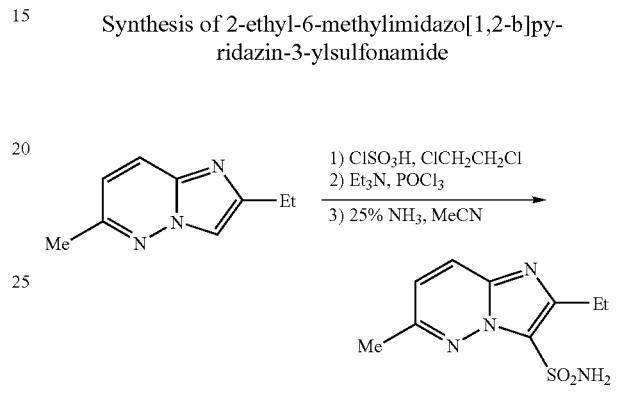

The title compound was obtained as pale brown crystals by the same reaction as in Reference Example 2 except that 2-ethyl-6-methylimidazo[1,2-b]pyridazine was used in place of 6-ethyl-2-methylimidazo[1,2-b]pyridazine. The yield was 44.0%.

mp 198-199° C.

$^1$H NMR (DMSO-d$_6$, δ): 1.25 (3H, t, J=7.5 Hz), 2.62 (3H, s), 2.99 (2H, q, J=7.5 Hz), 7.34 (1H, d, J=9.3 Hz), 7.49 (2H, brs), 8.08 (1H, d, J=9.3 Hz).

IR (Nujol, cm$^{-1}$): 3312, 3195, 3061, 1578, 1546, 1489, 1397, 1383, 1363, 1342, 1306, 1202, 1169, 1133, 1083, 1036, 990, 906, 853, 818.

Reference Example 52

Synthesis of 2-ethyl-6-dimethylaminoimidazo[1,2-b]pyridazin-3-ylsulfonamide

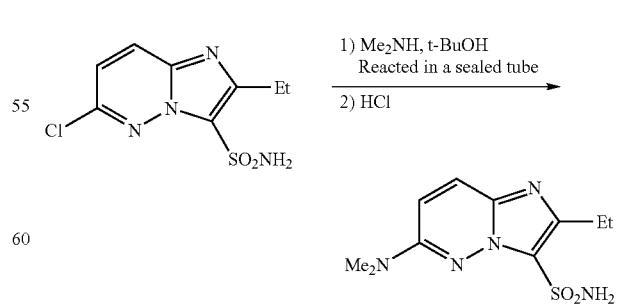

The title compound was obtained as colorless crystals by the same reaction as in Reference Example 45 except that 6-chloro-2-ethylimidazo[1,2-b]pyridazin-3-ylsulfonamide was used in place of 6-chloro-2-n-propylimidazo[1,2-b]pyridazin-3-ylsulfonamide. The yield was 87.4%.

mp 211-213° C.

$^1$H NMR (DMSO-$d_6$, δ): 1.22 (3H, t, J=7.5 Hz), 2.91 (2H, q, J=7.5 Hz), 3.10 (6H, s), 7.14 (2H, brs), 7.19 (1H, d, J=10.0 Hz), 7.85 (1H, d, J=10.0 Hz).

IR (Nujol, cm$^{-1}$): 3318, 2695, 1629, 1604, 1556, 1504, 1462, 1429, 1406, 1375, 1363, 1349, 1334, 1323, 1312, 1276, 1221, 1183, 1163, 1148, 1100, 1061, 1049, 970.

Reference Example 53

Synthesis of 2-ethyl-6-methylthioimidazo[1,2-b]pyridazin-3-ylsulfonamide

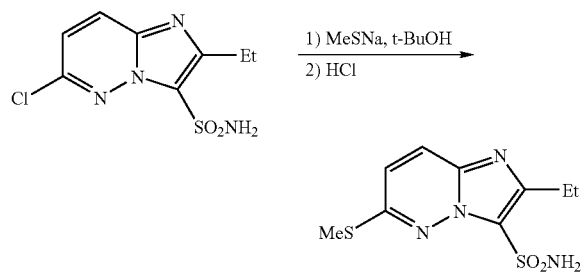

The title compound was obtained as colorless crystals by the same reaction as in Reference Example 47 except that 6-chloro-2-ethylimidazo[1,2-b]pyridazin-3-ylsulfonamide was used in place of 6-chloro-2-trifluoromethylimidazo[1,2-b]pyridazin-3-ylsulfonamide, and an aqueous solution of methanethiol sodium salt was used in place of the combination of potassium t-butoxide and ethanethiol. The yield was 78.3%.

mp 196-197° C.

$^1$H NMR (DMSO-$d_6$, δ) 1.26 (3H, t, J=7.5 Hz), 2.67 (3H, s), 2.98 (2H, q, J=7.5 Hz), 7.36 (1H, d, J=9.5 Hz), 7.40 (2H, brs), 8.00 (1H, d, J=9.5 Hz).

Reference Example 54

Synthesis of 2-ethyl-6-methylsulfonylimidazo[1,2-b]pyridazin-3-ylsulfonamide

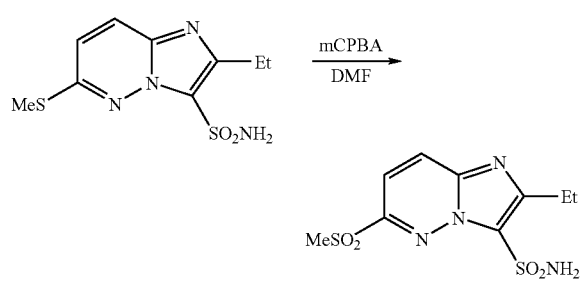

2-Ethyl-6-methylthioimidazo[1,2-b]pyridazin-3-ylsulfonamide (1.10 g, 4.04 mmol) was dissolved in DMF (10.0 ml) and stirred under ice-cooling, during which m-chloroperbenzoic acid (abbreviated into mCPBA) (70%, 2.48 g, 10.1 mmol) was added thereto. The mixture was stirred under ice-cooling for 1 hour and at room temperature for 3 hours, and then the reaction solution was poured into water (50.0 ml), and 25% ammonia water (1.0 ml) was added thereto. After the reaction solution was stirred for 5 minutes, the precipitated crystals were filtered and washed with water, to give the title compound as colorless crystals. The yield was 1.04 g (84.5%).

mp 225-226° C.

$^1$H NMR (DMSO-$d_6$, δ): 1.29 (3H, t, J=7.5 Hz), 3.09 (2H, q, J=7.5 Hz), 3.63 (3H, s), 7.89 (2H, brs), 7.94 (1H, d, J=9.5 Hz), 8.53 (1H, d, J=9.5 Hz).

IR (Nujol, cm$^{-1}$): 3615, 3352, 3015, 1608, 1547, 1523, 1505, 1455, 1411, 1396, 1369, 1339, 1313, 1266, 1210, 1171, 1158, 1130, 1117, 1082, 1000, 969, 919, 826.

Reference Example 55

Synthesis of 2-ethyl-6-methoxyimidazo[1,2-b]pyridazin-3-ylsulfonamide

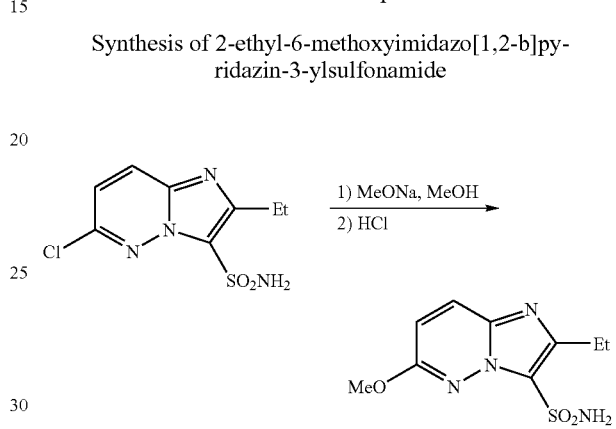

6-Chloro-2-ethylimidazo[1,2-b]pyridazin-3-ylsulfonamide (1.50 g, 5.75 mmol) was suspended in methanol (30.0 ml) and stirred at room temperature, during which sodium methoxide (28%, 3.34 g, 17.3 mmol) was added thereto. The mixture was heated for 5 hours under reflux, and then the reaction solution was poured into ice-water (200 ml) and adjusted to pH 2 with conc. hydrochloric acid. The precipitated crystals were filtered and washed with water, to give the title compound as colorless crystals. The yield was 1.02 g (69.3%).

mp 213-214° C.

$^1$H NMR (DMSO-$d_6$, δ): 1.24 (3H, t, J=7.5 Hz), 2.96 (2H, q, J=7.5 Hz), 4.05 (3H, s), 7.08 (1H, d, J=9.6 Hz), 7.42 (2H, brs), 8.06 (1H, d, J=9.6 Hz).

Reference Example 56

Synthesis of 2-ethyl-6-ethoxyimidazo[1,2-b]pyridazin-3-ylsulfonamide

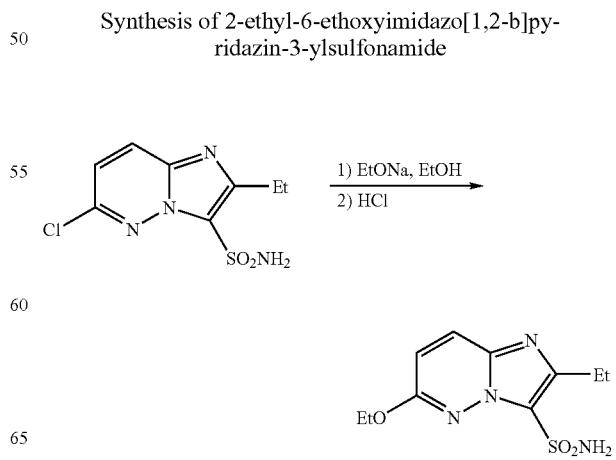

The title compound was obtained as pale orange crystals by the same reaction as in Reference Example 55 except that a combination of sodium ethoxide and ethanol was used in place of the combination of sodium methoxide and methanol. The yield was 68.0%.

mp 200-202° C.

$^1$H NMR (DMSO-$d_6$, δ): 1.25 (3H, t, J=7.5 Hz), 1.39 (3H, t, J=7.1 Hz), 2.96 (2H, q, J=7.5 Hz), 4.49 (2H, q, 7.1 Hz), 7.05 (1H, d, J=9.7 Hz), 7.40 (2H, brs), 8.06 (1H, d, J=9.7 Hz).

IR (Nujol, cm$^{-1}$): 3320, 1340, 1280, 1210, 1165, 825.

Reference Example 57

Synthesis of 6-ethoxy-2-methylimidazo[1,2-b]pyridazin-3-ylsulfonamide

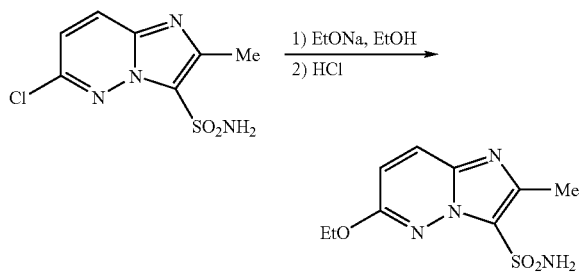

The title compound was obtained as white crystals by the same reaction as in Reference Example 55 except that 6-chloro-2-methylimidazo[1,2-b]pyridazin-3-ylsulfonamide was used in place of 6-chloro-2-ethylimidazo[1,2-b]pyridazin-3-ylsulfonamide, and a combination of sodium ethoxide and ethanol was used in place of the combination of sodium methoxide and methanol. The yield was 92.0%.

mp 225-226° C.

$^1$H NMR (DMSO-$d_6$, δ): 1.39 (3H, t, J=7.5 Hz), 2.55 (3H, s), 4.50 (2H, q, J=7.5 Hz), 7.03 (1H, d, J=9.6 Hz), 7.38 (2H, brs), 8.02 (1H, d, J=9.6 Hz).

IR (Nujol, cm$^{-1}$): 3355, 1349, 1293, 1222, 1172, 826.

Reference Example 58

Synthesis of 6-ethylthio-2-methylimidazo[1,2-b]pyridazin-3-ylsulfonamide

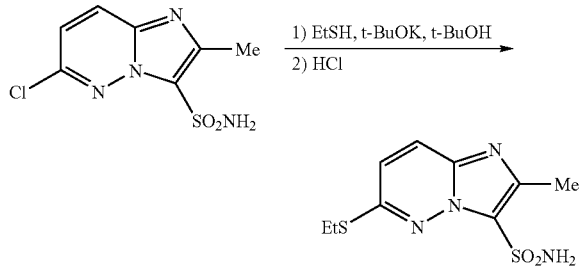

The title compound was obtained as pale brown crystals by the same reaction as in Reference Example 47 except that 6-chloro-2-methylimidazo[1,2-b]pyridazin-3-ylsulfonamide was used in place of 6-chloro-2-trifluoromethylimidazo[1,2-b]pyridazin-3-ylsulfonamide. The yield was 62.0%.

mp 217-219° C.

$^1$H NMR (DMSO-$d_6$, δ): 1.36 (3H, t, J=7.2 Hz), 2.56 (3H, s), 3.30 (2H, q, J=7.2 Hz), 7.29 (1H, d, J=9.3 Hz), 7.38 (2H, brs), 7.97 (1H, d, J=9.3 Hz).

IR (Nujol, cm$^{-1}$): 3380, 1343, 1303, 1169, 1141, 1068, 816.

Reference Example 59

Synthesis of 2-methyl-6-methylsulfonylimidazo[1,2-b]pyridazin-3-ylsulfonamide

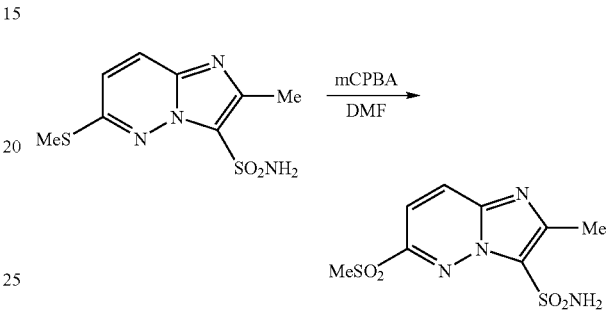

The title compound was obtained as pale yellow crystals by the same reaction as in Reference Example 54 except that 2-methyl-6-methylthioimidazo[1,2-b]pyridazin-3-ylsulfonamide was used in place of 2-ethyl-6-methylthioimidazo[1,2-b]pyridazin-3-ylsulfonamide. The yield was 84.0%.

mp 245-246° C.

$^1$H NMR (DMSO-$d_6$, δ): 2.69 (3H, s), 3.63 (3H, s), 7.88 (2H, brs), 7.88 (1H, d, J=9.6 Hz), 8.50 (1H, d, J=9.6 Hz).

IR (Nujol, cm$^{-1}$): 3380, 1348, 1323, 1174, 1122, 778, 723.

Reference Example 60

Synthesis of 2-chloro-6-isopropoxyimidazo[1,2-b]pyridazin-3-ylsulfonamide

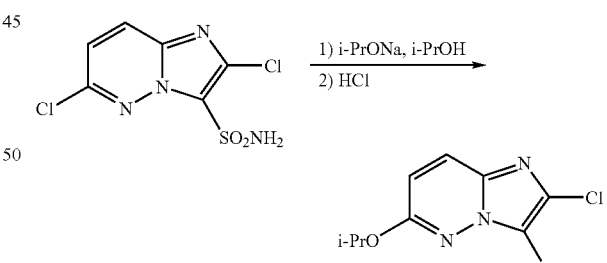

The title compound was obtained as white crystals by the same reaction as in Reference Example 55 except that 2,6-dichloroimidazo[1,2-b]pyridazin-3-ylsulfonamide was used in place of 6-chloro-2-ethylimidazo[1,2-b]pyridazin-3-ylsulfonamide, and a combination of sodium isopropoxide and isopropanol was used in place of the combination of sodium methoxide and methanol. The yield was 82.6%.

mp 213-214° C.

$^1$H NMR (DMSO-$d_6$, δ): 1.40 (6H, d, J=6.0 Hz), 5.48 (1H, sept, J=6.0 Hz), 7.10 (1H, d, J=9.6 Hz), 7.74 (2H, s), 8.09 (1H, d, J=9.6 Hz).

Reference Example 61

Synthesis of 2-chloro-6-ethylaminoimidazo[1,2-b]pyridazin-3-ylsulfonamide

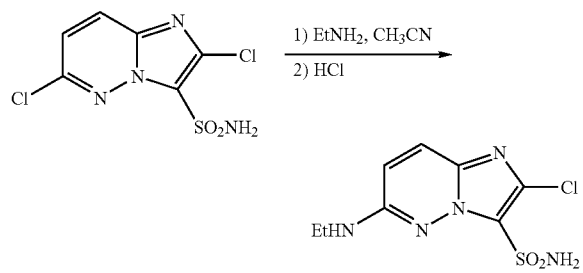

2,6-Dichloroimidazo[1,2-b]pyridazin-3-ylsulfonamide (2.00 g, 7.50 mmol) and ethylamine (50%, 10.0 ml) were stirred in acetonitrile (100 ml) at 70° C. for 8 hours. The reaction mixture was concentrated to dryness, dissolved in ice-water (50.0 ml), and adjusted to pH 6 with conc. hydrochloric acid. The precipitated crystals were filtered and washed with water to give the title compound as pale yellow crystals. The yield was 1.10 g (53.3%).

mp 218-220° C.

$^1$H NMR (DMSO-d$_6$, δ): 1.22 (3H, t), 3.23-3.67 (2H, m), 6.90 (1H, d), 7.27 (2H, brs), 7.67 (1H, d).

Reference Example 62

Synthesis of 6-chloro-2,8-dimethylimidazo[1,2-b]pyridazine

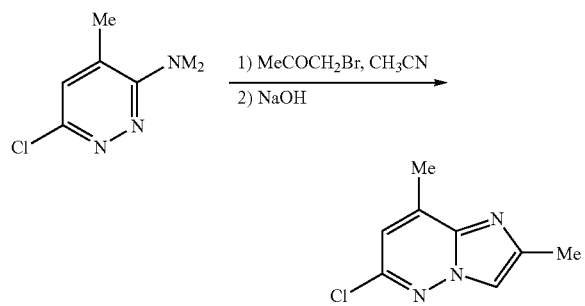

3-Amino-6-chloro-4-methylpyridazine (5.50 g, 38.3 mmol) and bromoacetone (6.90 g, 40.0 mmol) were heated in acetonitrile (50.0 ml) for 8 hours under reflux. The reaction solution was concentrated under reduced pressure, and water (100 ml) was added to the residues which were then adjusted to pH 9 with 20% aqueous sodium hydroxide and extracted twice with ethyl acetate. The extracts were combined, dried over anhydrous magnesium sulfate and concentrated, and the residues were purified by silica gel column chromatography (ethyl acetate:chloroform=1:2), to give the title compound as white crystals. The yield was 3.80 g (54.6%).

mp 109-110° C.

$^1$H NMR (CDCl$_3$, δ): 2.49-2.50 (3H, m), 2.63-2.64 (3H, m), 6.83-6.85 (1H, m), 7.66 (1H, s).

IR (Nujol, cm$^{-1}$): 3129, 1592, 1532, 1289, 1113, 1092, 985, 928, 843, 772.

Reference Example 63

Synthesis of 6-chloro-2,8-dimethylimidazo[1,2-b]pyridazin-3-ylsulfonamide

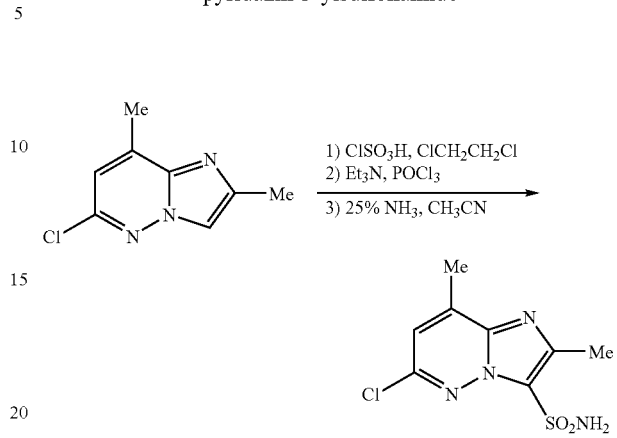

The title compound was obtained as white crystals by the same reaction as in Reference Example 2 except that 6-chloro-2,8-dimethylimidazo[1,2-b]pyridazine was used in place of 6-ethyl-2-methylimidazo[1,2-b]pyridazine. The yield was 51.1%.

mp 247-248° C.

$^1$H NMR (DMSO-d$_6$, δ): 2.59 (6H, s), 7.5-7.6 (1H, m), 7.71 (2H, brs).

IR (Nujol, cm$^{-1}$): 3324, 3160, 3063, 1557, 1509, 1459, 1377, 1340, 1295, 1170, 1134, 1067, 933, 910, 863, 724, 613.

Reference Example 64

Synthesis of 2,8-dimethyl-6-dimethylaminoimidazo[1,2-b]pyridazin-3-ylsulfonamide

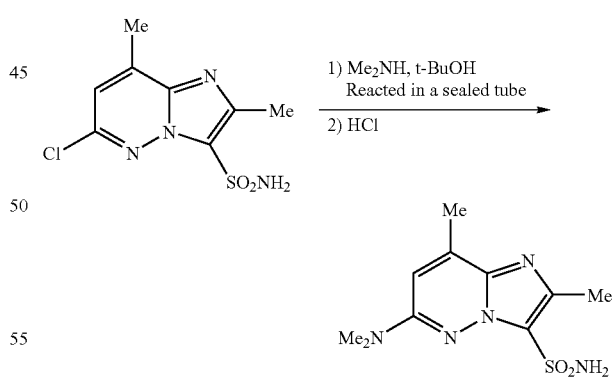

The title compound was obtained as pale yellow crystals by the same reaction as in Reference Example 45 except that 6-chloro-2,8-dimethylimidazo[1,2-b]pyridazin-3-ylsulfonamide was used in place of 6-chloro-2-n-propylimidazo[1,2-b]pyridazin-3-ylsulfonamide. The yield was 85.9%.

mp 248-249° C.

$^1$H NMR (DMSO-d$_6$, δ): 2.4-2.5 (6H, m), 3.08 (6H, s), 7.08 (1H, s), 7.12 (2H, brs)

Reference Example 65

Synthesis of 2,8-dimethyl-6-methylthioimidazo[1,2-b]pyridazin-3-ylsulfonamide

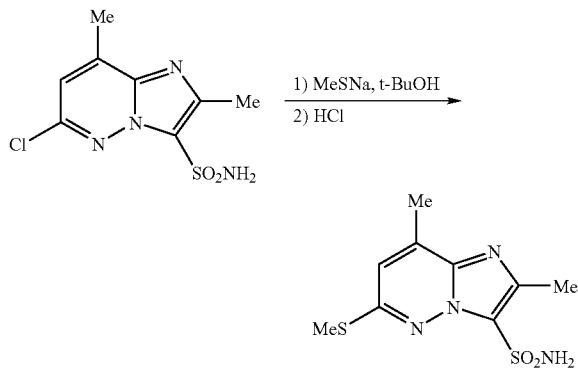

The title compound was obtained as pale yellow crystals by the same reaction as in Reference Example 47 except that 6-chloro-2,8-dimethylimidazo[1,2-b]pyridazin-3-ylsulfonamide was used in place of 6-chloro-2-trifluoromethylimidazo[1,2-b]pyridazin-3-ylsulfonamide, and an aqueous solution of methanethiol sodium salt was used in place of the combination of ethanethiol and potassium t-butoxide. The yield was 62.2%.

mp 233-234° C.

$^1$H NMR (DMSO-$d_6$, δ): 2.50 (3H, s), 2.55 (3H, s), 2.64 (3H, s), 7.24-7.25 (1H, m), 7.38 (2H, brs).

IR (Nujol, cm$^{-1}$): 3373, 1346, 1292, 1179, 1138, 1127, 858, 730, 611.

Synthesis Example 1

Synthesis of 1-(4,6-dimethoxypyrimidin-2-yl)-3-(6-ethyl-2-methylimidazo[1,2-b]pyridazin-3-ylsulfonyl)urea (Compound No. 13)

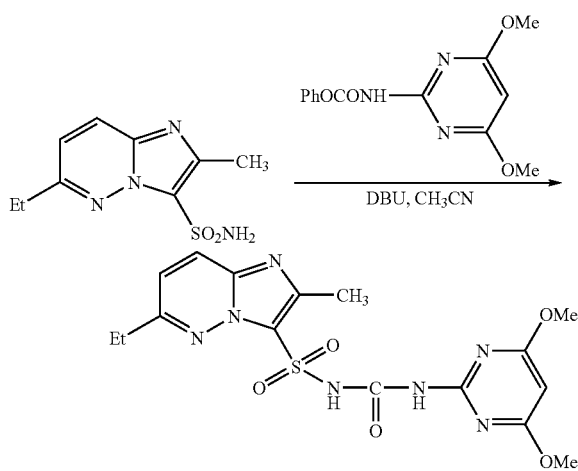

As shown in the above reaction scheme, 6-ethyl-2-methylimidazo[1,2-b]pyridazin-3-ylsulfonamide (0.60 g, 2.50 mmol) and phenyl N-(4,6-dimethoxypyrimidin-2-yl)carbamate (0.76 g, 2.76 mmol) were suspended in acetonitrile (10 ml) and stirred under ice-cooling, during which DBU (0.46 g, 3.02 mmol) was added thereto. The temperature of the reaction solution was increased to room temperature, and the mixture was stirred at the same temperature for 4 hours. The reaction solution was poured into ice-water (150 ml) and adjusted to pH 3 with conc. hydrochloric acid. The reaction mixture was stirred at room temperature for 5 minutes, and the precipitated crystals were washed with water, acetonitrile and diethyl ether in this order, and collected by filtration. The crystals were dried under reduced pressure to give the title compound as colorless crystals. The yield was 0.55 g (52%), and the melting point was 172 to 174° C.

$^1$H NMR (DMSO-$d_6$, δ ppm): 1.02 (3H, t, J=7.5 Hz), 2.64 (3H, s), 2.69 (2H, q, J=7.5 Hz), 3.97 (6H, s), 6.03 (1H, s), 7.44 (1H, d, J=9.4 Hz), 8.15 (1H, d, J=9.4 Hz), 10.56 (1H, s), 13.21 (1H, brs)

Synthesis Example 2

Synthesis of 1-(4,6-dimethoxypyrimidin-2-yl)-3-(2-ethyl-6-ethylthioimidazo[1,2-b]pyridazin-3-ylsulfonyl)urea (Compound No. 7)

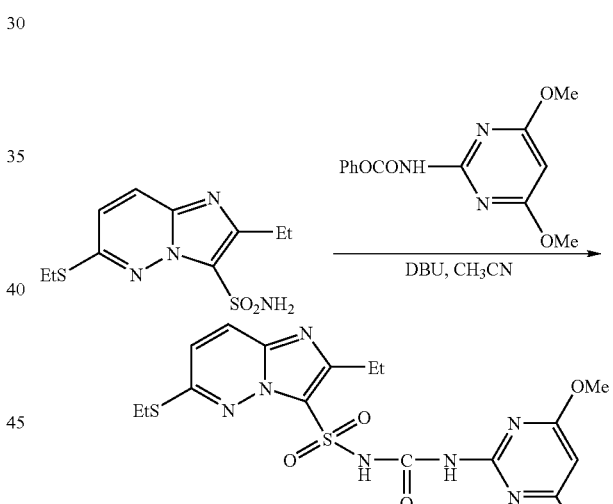

As shown in the above reaction scheme, 2-ethyl-6-ethylthioimidazo[1,2-b]pyridazin-3-ylsulfonamide (0.19 g, 0.66 mmol) and phenyl N-(4,6-dimethoxypyrimidin-2-yl)carbamate (0.20 g, 0.73 mmol) were suspended in acetonitrile (5 ml) and stirred at room temperature, during which DBU (0.11 g, 0.73 mmol) was added thereto. After the mixture was stirred at room temperature for 2 hours, the reaction solution was poured into water (50 ml) and adjusted to pH 2 with dilute hydrochloric acid. The precipitated crystals were collected by filtration, and washed with water and ether in this order. The crystals were dried under reduced pressure to give the title compound as colorless crystals. The yield was 0.18 g (58%), and the melting point was 160 to 165° C. (dec.).

$^1$H NMR (DMSO-d$_6$, δ ppm): 1.21 (3H, t, J=7.5 Hz), 1.31 (3H, t, J=7.5 Hz), 3.0-3.2 (4H, m), 3.93 (6H, s), 6.06 (1H, s), 7.42 (1H, d, J=9.5 Hz), 8.09 (1H, d, J=9.6 Hz), 10.59 (1H, brs), 12.9 (1H, brs).

Synthesis Example 3

Synthesis of 1-(4,6-dimethoxypyrimidin-2-yl)-3-(6-ethoxy-2-methylimidazo[1,2-a]pyridin-3-ylsulfonyl) urea (Compound No. 32)

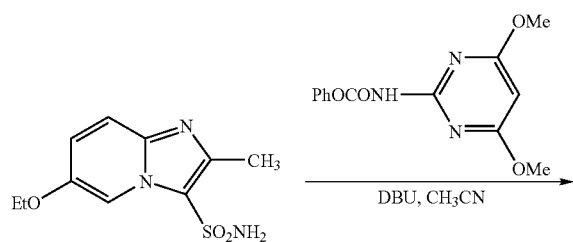

As shown in the above reaction scheme, 6-ethoxy-2-methylimidazo[1,2-a]pyridin-3-sulfonamide (0.04 g, 0.156 mmol) and phenyl N-(4,6-dimethoxypyrimidin-2-yl) carbamate (0.048 g, 0.172 mmol) were suspended in acetonitrile (1 ml) and stirred at room temperature, during which DBU (0.026 g, 0.172 mmol) was added thereto. After the mixture was stirred at room temperature for 2 hours, the reaction solution was poured into water (20 ml) and adjusted to pH 3 with dilute hydrochloric acid. The precipitated crystals were collected by filtration, and washed with water and ether in this order. The crystals were dried under reduced pressure to give the title compound as pale brown crystals. The yield was 0.06 g (87%), and the melting point was 159 to 164° C. (dec.).

$^1$H NMR (DMSO-d$_6$, δ ppm): 1.38 (3H, t, J=7.0 Hz), 2.56 (3H, s), 3.92 (6H, s), 4.05 (2H, q, J=6.9 Hz), 6.00 (1H, s), 7.3-7.5 (1H, m), 7.65 (1H, d, J=9.7 Hz), 8.3-8.4 (1H, m), 10.54 (1H, brs), 12.7-13.0 (1H, brs).

The compounds shown in Tables 1 to 4 below and Compound No. 35 were synthesized in the same manner as described above. As control compounds used in test examples shown later, Comparative Compounds 1 and 2 were also synthesized. In the tables, Compound Nos. 13, 7 and 32 described above are also shown.

TABLE 1

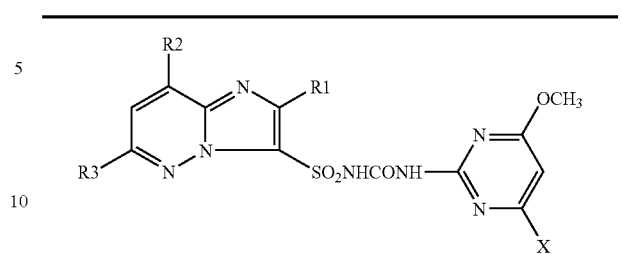

| Compound No. | R1 | R2 | R3 | X | mp (° C.) |
|---|---|---|---|---|---|
| 1 | C$_2$H$_5$ | H | CH$_3$ | OCH$_3$ | 182-184 |
| 2 | C$_2$H$_5$ | H | Cl | OCH$_3$ | 174-175 |
| 3 | Cl | H | NHC$_2$H$_5$ | OCH$_3$ | 169-171 |
| 4 | C$_2$H$_5$ | H | N(CH$_3$)$_2$ | OCH$_3$ | 174-176 |
| 5 | C$_2$H$_5$ | H | OC$_2$H$_5$ | OCH$_3$ | 180-181 |
| 6 | C$_2$H$_5$ | H | OCH$_3$ | OCH$_3$ | 118-123 (dec.) |
| 7 | C$_2$H$_5$ | H | SC$_2$H$_5$ | OCH$_3$ | 160-165 (dec.) |
| 8 | C$_2$H$_5$ | H | SCH$_3$ | OCH$_3$ | 146-148 |
| 9 | C$_2$H$_5$ | H | SO$_2$CH$_3$ | OCH$_3$ | 206-208 |
| 10 | CF$_3$ | H | OC$_2$H$_5$ | OCH$_3$ | 169-171 |
| 11 | CF$_3$ | H | SC$_2$H$_5$ | OCH$_3$ | 179-180 |
| 12 | CF$_3$ | H | SCH$_3$ | OCH$_3$ | 266-267 |
| 13 | CH$_3$ | H | C$_2$H$_5$ | OCH$_3$ | 172-174 |
| 14 | CH$_3$ | H | N(CH$_3$)$_2$ | OCH$_3$ | 183-185 (dec.) |
| 15 | CH$_3$ | CH$_3$ | N(CH$_3$)$_2$ | OCH$_3$ | 266-268 (dec.) |
| 16 | CH$_3$ | H | OC$_2$H$_5$ | OCH$_3$ | 168-170 (dec.) |
| 17 | CH$_3$ | H | OCH$_3$ | OCH$_3$ | 241 |
| 18 | CH$_3$ | H | SC$_2$H$_5$ | OCH$_3$ | 163-165 |
| 19 | CH$_3$ | H | SCH$_3$ | OCH$_3$ | 178-180 (dec.) |
| 20 | CH$_3$ | CH$_3$ | SCH$_3$ | OCH$_3$ | 191-193 (dec.) |
| 21 | CH$_3$ | H | SO$_2$CH$_3$ | OCH$_3$ | 246-248 (dec.) |
| 22 | Cl | H | N(CH$_3$)$_2$ | OCH$_3$ | 193-195 |
| 23 | Cl | H | OC$_2$H$_5$ | OCH$_3$ | 168-169 |
| 24 | Cl | H | OC$_3$H$_7$(i) | OCH$_3$ | 178-180 |
| 25 | Cl | H | SC$_2$H$_5$ | OCH$_3$ | 180-182 |
| 26 | Cl | H | SCH$_3$ | OCH$_3$ | 163-165 |
| 27 | Cl | H | SCH$_3$ | CH$_3$ | 172-174 |
| 28 | n-C$_3$H$_7$ | H | Cl | OCH$_3$ | 183-188 (dec.) |
| 29 | n-C$_3$H$_7$ | H | N(CH$_3$)$_2$ | OCH$_3$ | 203-206 (dec.) |
| 30 | n-C$_3$H$_7$ | H | OC$_2$H$_5$ | OCH$_3$ | 177-178 (dec.) |
| 31 | n-C$_3$H$_7$ | H | SCH$_3$ | OCH$_3$ | 176-178 (dec.) |
| Comparison 1 | CH$_3$ | H | H | OCH$_3$ | 173-175 (dec.) |
| Comparison 2 | Cl | H | H | OCH$_3$ | 189-190 |

TABLE 2

| Compound No. | R1 | R2 | X | Melting point (° C.) |
|---|---|---|---|---|
| 32 | CH$_3$ | OC$_2$H$_5$ | OCH$_3$ | 159-164 (dec.) |

TABLE 3

| Compound No. | R1 | R2 | R3 | X | Melting point (°C.) |
|---|---|---|---|---|---|
| 33 | CH₃ | H | OCH₃ | OCH₃ | 211-213 |
| 34 | CH₃ | H | OC₂H₅ | OCH₃ | −185 |

TABLE 4

| Compound No. | R1 | X | Melting point (°C.) |
|---|---|---|---|
| 35 | SO₂CH₃ | OCH₃ | 190-201 |

NMR data (DMSO-$d_6$, δ ppm)

Compound No. 1:
1.32 (3H, t, J=7.5 Hz), 2.37 (3H, s), 3.06 (2H, q, J=7.5 Hz), 3.99 (6H, s), 6.02 (1H, s), 7.38 (1H, d, J=9.3 Hz), 8.14 (1H, d, J=9.3 Hz), 10.55 (1H, s), 13.26 (1H, brs).

Compound No. 2:
1.33 (3H, t, J=7.5 Hz), 3.09 (2H, q, J=7.5 Hz), 3.99 (6H, s), 6.00 (1H, s), 7.63 (1H, d, J=9.6 Hz), 8.35 (1H, d, J=9.6 Hz), 10.58 (1H, brs), 13.37 (1H, brs).

Compound No. 3:
1.00 (3H, t), 2.80-3.23 (2H, m), 3.96 (6H, s), 5.98 (1H, s), 6.93 (1H, d), 7.38 (1H, s), 7.80 (1H, d), 10.60 (1H, brs), 13.02 (1H, brs).

Compound No. 4:
1.28 (3H, t, J=7.5 Hz), 2.94 (6H, s), 2.98 (2H, q, J=7.5 Hz), 3.92 (6H, s), 6.01 (1H, s), 7.22 (1H, d, J=10.0 Hz), 7.90 (1H, d, J=10.0 Hz), 10.53 (1H, s), 12.85 (1H, brs).

Compound No. 5:
1.24 (3H, t, J=7.0 Hz), 1.31 (3H, t, J=7.5 Hz), 3.03 (2H, q, J=7.5 Hz), 3.94 (6H, s), 4.17 (2H, q, J=7.0 Hz), 6.04 (1H, s), 7.11 (1H, d, J=9.7 Hz), 8.12 (1H, d, J=9.7 Hz), 10.57 (1H, brs), 13.00 (1H, brs).

Compound No. 6:
1.30 (3H, t, J=7.5 Hz), 3.03 (2H, q, J=7.5 Hz), 3.80 (3H, s), 3.92 (6H, s), 6.02 (1H, s), 7.15 (1H, d, J=9.7 Hz), 8.10 (1H, d, J=9.7 Hz), 10.56 (1H, s), 13.01 (1H, brs).

Compound No. 7: See Synthesis Example 2.

Compound No. 8:
1.31 (3H, t, J=7.5 Hz), 2.47 (3H, s), 3.06 (2H, q, J=7.5 Hz), 3.93 (6H, s), 6.04 (1H, s), 7.45 (1H, d, J=9.6 Hz), 8.09 (1H, d, J=9.6 Hz), 10.57 (1H, brs), 12.96 (1H, brs).

Compound No. 9:
1.36 (3H, t, J=7.5 Hz), 3.18 (2H, q, J=7.5 Hz), 3.26 (3H, s), 3.95 (6H, s), 5.99 (1H, s), 7.99 (1H, d, J=9.5 Hz), 8.58 (1H, d, J=9.5 Hz), 10.56 (1H, s), 13.34 (1H, brs).

Compound No. 10:
1.24 (3H, t, J=7.0 Hz), 3.94 (6H, s), 4.20 (2H, q, J=7.0 Hz), 6.06 (1H, s), 7.31 (1H, d, J=9.8 Hz), 8.34 (1H, d, J=9.8 Hz), 10.70 (1H, brs), 13.26 (1H, brs).

Compound No. 11:
1.24 (3H, t, J=7.3 Hz), 3.08 (2H, q, J=7.3 Hz), 3.94 (6H, s), 5.94 (1H, s), 7.58 (1H, d, J=9.6 Hz), 8.28 (1H, d, J=9.6 Hz), 1.69 (1H, brs), 13.21 (1H, brs).

Compound No. 12:
2.49 (3H, s), 3.93 (6H, s), 6.04 (1H, s), 7.63 (1H, d, J=9.6 Hz), 8.29 (1H, d, J=9.6 Hz), 10.69 (1H, brs), 13.23 (1H, brs).

Compound No. 13: See Synthesis Example 1.

Compound No. 14:
2.55 (3H, s), 2.94 (6H, s), 3.92 (6H, s), 6.00 (1H, s), 7.21 (1H, d, J=9.9 Hz), 7.85 (1H, d, J=9.9 Hz), 10.52 (1H, brs), 12.85 (1H, brs)

Compound No. 15:
2.46 (3H, s), 2.55 (3H, s), 2.92 (6H, s), 3.92 (6H, s), 6.02 (1H, s), 7.10-7.11 (1H, m), 10.52 (1H, s), 12.83 (1H, s).

Compound No. 16:
1.26 (3H, t, J=7.5 Hz), 2.63 (3H, s), 3.96 (6H, s), 4.21 (2H, q, J=7.5 Hz), 6.02 (1H, s), 7.11 (1H, d, J=9.9 Hz), 8.10 (1H, d, J=9.9 Hz), 10.54 (1H, brs), 13.00 (1H, brs).

Compound No. 17:
2.60 (3H, s), 3.81 (3H, s), 3.92 (6H, s), 6.01 (1H, s), 7.14 (1H, d, J=9.7 Hz), 8.10 (1H, d, J=9.7 Hz), 10.56 (1H, s), 13.01 (1H, brs).

Compound No. 18:
1.23 (3H, t, J=7.5 Hz), 2.63 (3H, s), 3.08 (2H, q, J=7.5 Hz), 3.95 (6H, s), 5.99 (1H, s), 7.35 (1H, d, J=9.6 Hz), 8.02 (1H, d, J=9.6 Hz), 10.50 (1H, brs), 12.90 (1H, brs).

Compound No. 19:

Compound No. 20:
2.44 (3H, s), 2.50 (3H, s), 2.62 (3H, s), 3.93 (6H, s), 6.03 (1H, s), 7.32 (1H, s), 10.56 (1H, s), 12.93 (1H, s).

Compound No. 21:
2.75 (3H, s), 3.28 (3H, s), 3.96 (6H, s), 5.98 (1H, s), 7.98 (1H, d, J=9.0 Hz), 8.56 (1H, d, J=9.0 Hz), 10.53 (1H, s), 13.31 (1H, brs).

Compound No. 22:
2.97 (6H, s), 3.92 (6H, s), 5.96 (1H, s), 7.26 (1H, d, J=10.0 Hz), 7.88 (1H, d, J=10.0 Hz), 10.50 (1H, brs), 12.90 (1H, brs).

Compound No. 25:
1.24 (3H, t, J=7.3 Hz), 3.07 (2H, q, J=7.3 Hz), 3.94 (6H, s), 6.04 (1H, s), 7.52 (1H, d, J=9.6 Hz), 8.12 (1H, d, J=9.6 Hz), 10.67 (1H, brs), 13.10 (1H, brs).

Compound No. 26:
2.47 (3H, s), 3.93 (6H, s), 6.03 (1H, s), 7.57 (1H, d, J=9.6 Hz), 8.13 (1H, d, J=9.6 Hz), 10.65 (1H, brs), 13.12 (1H, brs).

Compound No. 27:
2.39 (3H, s), 2.48 (3H, s), 3.92 (3H, s), 6.58 (1H, s), 7.53 (1H, d, J=9.5 Hz), 8.10 (1H, d, J=9.5 Hz), 10.74 (1H, brs), 13.75 (1H, brs).

Compound No. 28:

0.98 (3H, t, J=7.4 Hz), 1.7-1.9 (2H, m), 3.04 (2H, t, J=7.4 Hz), 3.99 (6H, s), 6.01 (1H, s), 7.63 (1H, d, J=9.5 Hz), 8.35 (1H, d, J=9.5 Hz), 10.58 (1H, s), 13.38 (1H, s).

Compound No. 29:

0.95 (3H, t, J=7.3 Hz), 1.7-1.9 (2H, m), 2.9-3.0 (8H, m), 3.92 (6H, s), 6.03 (1H, s), 7.23 (1H, d, J=10.0 Hz), 7.90 (1H, d, J=10.0 Hz), 10.54 (1H, s), 12.9 (1H, s).

Compound No. 30:

0.97 (3H, t, J=7.3 Hz), 1.22 (3H, t, J=7.1 Hz), 1.7-1.9 (2H, m), 2.98 (2H, t, J=7.4 Hz), 3.93 (6H, s), 4.15 (2H, q, J=7.0 Hz), 6.05 (1H, s), 7.12 (1H, d, J=9.7 Hz), 8.13 (1H, d, J=9.7 Hz), 10.58 (1H, s), 13.0 (1H, s).

Compound No. 31:

0.97 (3H, t, J=7.3 Hz), 1.7-1.9 (2H, m), 2.45 (3H, s), 3.00 (2H, t, J=7.5 Hz), 3.93 (6H, s), 6.05 (1H, s), 7.45 (1H, d, J=9.6 Hz), 8.09 (1H, d, J=9.5 Hz), 10.58 (1H, s), 12.9-13.0 (1H, brs).

Compound No. 32: See Synthesis Example 3.

Synthesis Example 4

Synthesis of 1-(2-chloro-6-n-propylimidazo[1,2-b]pyridazin-3-ylsulfonyl)-3-(4,6-dimethoxypyrimidin-2-yl)urea (Compound No. 38)

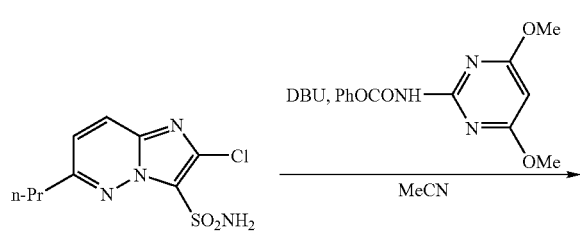

-continued

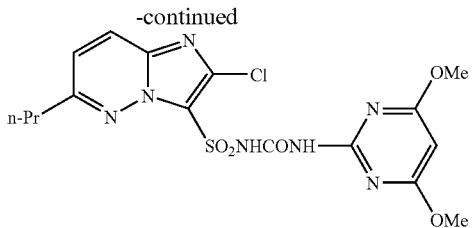

2-Chloro-6-n-propylimidazo[1,2-b]pyridazin-3-ylsulfonamide (0.49 g, 1.78 mmol), phenyl N-(4,6-dimethoxypyrimidin-2-yl)carbamate (0.55 g, 2 mmol) and acetonitrile (5 ml) were introduced into a 25-ml eggplant type flask and stirred at room temperature, and DBU (0.31 g, 2 mmol) was added all at once thereto, and the mixture was stirred at room temperature for 3 hours. After the reaction was completed, the reaction solution was poured into water (50 ml) and adjusted to about pH 2 with dilute hydrochloric acid, whereby crystals were formed. The crystals were collected by filtration, washed with water, acetone and ether in this order and dried under reduced pressure to give the title compound as pale brown crystals.

The yield was 0.71 g (89.5%).

mp 199-201° C. (dec.)

$^1$H NMR (DMSO-$d_6$, δ): 0.70 (3H, t, J=7.3 Hz), 1.4-1.5 (2H, m), 2.6-2.7 (2H, m), 3.97 (6H, s), 6.08 (1H, s), 7.57 (1H, d, J=9.4 Hz), 8.26 (1H, d, J=9.4 Hz), 10.68 (1H, brs), 13.4-13.5 (1H, m).

IR (Nujol, cm$^{-1}$): 3643, 1720, 1703, 1607, 1573, 1453, 1359, 1324, 1290, 1199, 1162, 1016, 888, 840, 629, 589, 514.

Compound Nos. 36, 37 and 39 to 52 shown in Table 5 below were synthesized in the same manner as described above. In the table, Compound No. 38 described above is also shown.

TABLE 5

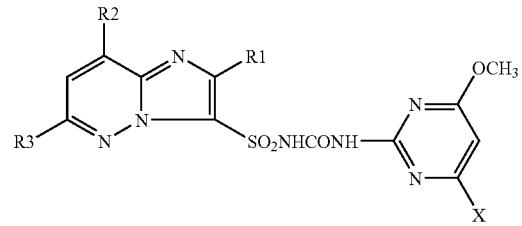

| Compound No. | R1 | R2 | R3 | X | mp (° C.) |
|---|---|---|---|---|---|
| 36 | CH$_3$ | H | n-C$_3$H$_7$ | OCH$_3$ | 180-184 (dec.) |
| 37 | Cl | H | C$_2$H$_5$ | OCH$_3$ | 162-166 |
| 38 | Cl | H | n-C$_3$H$_7$ | OCH$_3$ | 199-201 (dec.) |
| 39 | CH$_3$ | H | i-C$_3$H$_7$ | OCH$_3$ | 164-165 (dec.) |
| 40 | Cl | H | i-C$_3$H$_7$ | OCH$_3$ | 197-199 |
| 41 | Cl | H | n-C$_4$H$_9$ | OCH$_3$ | 164-167 |
| 42 | Cl | H | i-C$_4$H$_9$ | OCH$_3$ | 171-174 |
| 43 | Cl | H | CH$_2$=CH | OCH$_3$ | 140-144 |
| 44 | Cl | H | c-C$_3$H$_5$ | OCH$_3$ | 166-169 |
| 45 | Cl | H | (E)—CH$_3$CH=CH | OCH$_3$ | 170-174 |
| 46 | F | H | n-C$_3$H$_7$ | OCH$_3$ | 177.3-178.5 |
| 47 | CN | H | n-C$_3$H$_7$ | OCH$_3$ | 167.6-170.0 |
| 48 | SC$_2$H$_5$ | H | n-C$_3$H$_7$ | OCH$_3$ | 169.9-170.4 |
| 49 | SO$_2$C$_2$H$_5$ | H | n-C$_3$H$_7$ | OCH$_3$ | 228.4-230.8 |
| 50 | Cl | H | (E)—Cl—CH=CH | OCH$_3$ | 170.0-172.5 |

TABLE 5-continued

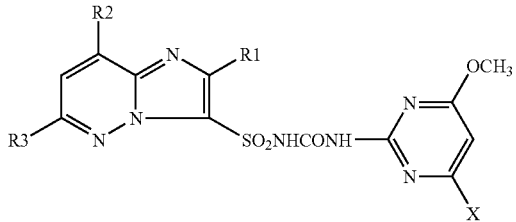

| Compound No. | R1 | R2 | R3 | X | mp (° C.) |
|---|---|---|---|---|---|
| 51 | Cl | H | (Z)—Cl—CH=CH | OCH$_3$ | 171.0-174.0 |
| 52 | Cl | H | HC≡C | OCH$_3$ | >200 (dec.) |

NMR data (DMSO-d$_6$, δ ppm)

Compound No. 36:
0.71 (3H, t, J=7.4 Hz), 1.4-1.5 (2H, m), 2.6-2.7 (5H, m), 3.97 (6H, s), 6.05 (1H, s), 7.43 (1H, d, J=9.4 Hz), 8.15 (1H, d, J=9.4 Hz), 10.5-10.6 (1H, br), 13.2-13.3 (1H, br).

Compound No. 37:
1.02 (3H, t, J=7.5 Hz), 2.70 (2H, q, J=7.5 Hz), 3.96 (6H, s), 6.06 (1H, s), 7.58 (1H, d, J=9.4 Hz), 8.26 (1H, d, J=9.4 Hz), 10.66 (1H, brs), 13.39 (1H, brs).

Compound No. 38: See Synthesis Example 4.

Compound No. 39:
1.09 (6H, d, J=6.9 Hz), 2.64 (3H, s), 2.96 (1H, sept, J=6.9 Hz), 3.95 (6H, s), 6.04 (1H, s), 7.51 (1H, d, J=9.4 Hz), 8.17 (1H, d, J=9.4 Hz), 10.56 (1H, brs), 13.1-13.2 (1H, br).

Compound No. 40:
1.09 (6H, d, J=7.0 Hz), 2.97 (1H, sept, J=7.0 Hz), 3.95 (6H, s), 6.06 (1H, s), 7.65 (1H, d, J=9.5 Hz), 8.28 (1H, d, J=9.5 Hz), 10.66 (1H, brs), 13.31 (1H, brs).

Compound No. 41:
0.71 (3H, t, J=7.4 Hz), 1.09 (2H, sext, J=7.4 Hz), 1.39 (2H, tt, 7.7, 7.4 Hz), 2.66 (2H, t, J=7.7 Hz), 3.97 (6H, s), 6.07 (1H, s), 7.58 (1H, d, J=9.4 Hz), 8.26 (1H, d, J=9.4 Hz), 10.68 (1H, brs), 13.42 (1H, brs).

Compound No. 42:
0.66 (6H, d, J=6.6 Hz), 1.88 (1H, m), 2.53 (2H, d, J=7.4 Hz), 3.97 (6H, s), 6.09 (1H, s), 7.56 (1H, d, J=9.4 Hz), 8.26 (1H, d, J=9.4 Hz), 10.68 (1H, brs), 13.42 (1H, brs).

Compound No. 43:
3.96 (6H, s), 5.77 (1H, d, J=11.0 Hz), 6.05 (1H, s), 6.35 (1H, d, J=17.7 Hz), 6.58 (1H, dd, J=17.7, 11.0 Hz), 7.97 (1H, d, J=9.6 Hz), 8.32 (1H, d, J=9.6 Hz), 10.62 (1H, brs), 13.34 (1H, brs).

Compound No. 44:
0.75-0.90 (2H, m), 0.90-1.05 (2H, m), 2.05-2.15 (1H, m), 3.96 (6H, s), 6.06 (1H, s), 7.53 (1H, d, J=9.5 Hz), 8.19 (1H, d, J=9.5 Hz), 10.64 (1H, brs), 13.21 (1H, brs).

Compound No. 45:
1.83 (3H, dd, J=6.8, 1.6 Hz), 3.97 (6H, s), 6.10 (1H, s), 6.20 (1H, dq, J=16.0, 1.6 Hz), 6.83 (1H, dq, J=16.0, 6.8 Hz), 7.84 (1H, d, J=9.6 Hz), 8.25 (1H, d, J=9.6 Hz), 10.63 (1H, brs), 13.36 (1H, brs).

Compound No. 46:
0.72 (3H, t, J=7.3 Hz), 1.48 (2H, m), 2.67 (2H, t, J=7.6 Hz), 3.97 (6H, s), 6.06 (1H, s), 7.60 (1H, d, J=9.4 Hz), 8.27 (1H, d, J=9.4 Hz), 10.66 (1H, s), 13.40 (1H, s).

Compound No. 47:
0.73 (3H, t, J=7.4 Hz), 1.51 (2H, m), 2.71 (2H, t, J=7.6 Hz), 3.97 (6H, s), 6.08 (1H, s), 7.66 (1H, d, J=9.5 Hz), 8.40 (1H, d, J=9.5 Hz), 10.75 (1H, brs), 13.4-13.8 (1H, br).

Compound No. 48:
0.68 (3H, t, J=7.3 Hz), 1.37 (3H, t, J=7.3 Hz), 1.43 (2H, m), 2.58 (2H, t, J=7.7 Hz), 3.23 (2H, q, J=7.3 Hz), 3.96 (6H, s), 6.06 (1H, s), 7.45 (1H, d, J=9.3 Hz), 8.18 (1H, d, J=9.3 Hz), 10.57 (1H, s), 13.24 (1H, s).

Compound No. 49:
0.72 (3H, t, J=7.3 Hz), 1.18 (3H, t, J=7.3 Hz), 1.45 (2H, m), 2.65 (2H, t, J=7.9 Hz), 3.74 (2H, q, J=7.3 Hz), 3.98 (6H, s), 6.11 (1H, s), 7.66 (1H, d, J=9.4 Hz), 8.45 (1H, d, J=9.4 Hz), 10.77 (1H, s), 13.60 (1H, s).

Compound No. 50:
3.96 (6H, s), 6.09 (1H, s), 6.73 (1H, d, J=13.7 Hz), 7.60 (1H, d, J=13.7 Hz), 7.88 (1H, d, J=9.6 Hz), 8.36 (1H, d, J=9.6 Hz), 10.61 (1H, brs), 13.31 (1H, brs).

Compound No. 51:
3.94 (6H, s), 6.03 (1H, s), 6.85 (1H, d, J=8.2 Hz), 7.01 (1H, d, J=8.2 Hz), 7.92 (1H, d, J=9.5 Hz), 8.38 (1H, d, J=9.5 Hz), 10.62 (1H, brs), 13.21 (1H, brs).

Compound No. 52:
3.99 (6H, s), 4.81 (1H, s), 5.98 (1H, s), 7.71 (1H, d, J=9.4 Hz), 8.37 (1H, d, J=9.4 Hz), 10.64 (1H, brs), 13.52 (1H, brs).

Preparation Example 1

10.6 parts of Compound No. 23 in Table 1, 5 parts of ethylene glycol, 0.1 part of butyl parabene, 0.2 part of silicone emulsion (Antifoam E20, Kao Corporation), 0.5 part of colloidal, water-containing aluminum silicate (Kunipia F, Kunimine Kogyo Co., Ltd.), 0.3 part of sodium carboxymethyl cellulose (Cellogen 7A, Dai-ichi Kogyo Seiyaku Co., Ltd.), 1 part of polyoxyalkylene allyl phenyl ether sulfate (Neugen EA-177, Dai-ichi Kogyo Seiyaku Co., Ltd.), 1 part of polyoxyalkylene distyryl phenyl ether (New Cargen FS-7, Takemoto Oil & Fat Co., Ltd.), 0.5 part of rosin glycerin ester (Solpoal 7518, Toho Chemical Industry Co., Ltd.) and 20.8 parts of water were mixed and milled in a wet system by Dynomill KDL (Sinmal Enterprise) to produce a uniform suspension, and then 2 parts of a sodium naphthalene sulfonate condensate (New Cargen PS-P, Takemoto Oil & Fat Co., Ltd.), 2 parts of didecyl dimethyl ammonium chloride (Catiogen DDM, Dai-ichi Kogyo Seiyaku Co., Ltd.), 15 parts of polyoxyethylene monolaurate (Emanon 1112, Kao. Corporation) and 41 parts of water were added thereto, to produce a uniform flowable agent.

Preparation Example 2

10.6 parts of Compound No. 37 in Table 5, 5 parts of ethylene glycol, 0.1 part of butyl parabene, 0.2 part of silicone emulsion (Antifoam E20, Kao Corporation), 0.5 part of colloidal water-containing aluminum silicate (Kunipia F, Kunimine Kogyo Co., Ltd.), 0.3 part of sodium carboxymethyl cellulose (Cellogen 7A, Dai-ichi Kogyo Seiyaku Co., Ltd.), 1 part of polyoxyalkylene allyl phenyl ether sulfate (Neugen EA-177, Dai-ichi Kogyo Seiyaku Co., Ltd.), 1 part of polyoxyalkylene distyryl phenyl ether (New Cargen FS-7, Takemoto Oil & Fat Co., Ltd.), 0.5 part of rosin glycerin ester (Solpoal 7518, Toho Chemical Industry Co., Ltd.) and 20.8 parts of water were mixed and milled in a wet system by Dynomill KDL (Sinmal Enterprise) to produce a uniform suspension, and then 2 parts of a sodium naphthalene sulfonate condensate (New Cargen PS-P, Takemoto Oil & Fat Co., Ltd.), 2 parts of didecyl dimethyl ammonium chloride (Catiogen DDM, Dai-ichi Kogyo Seiyaku Co., Ltd.), 12 parts of polyoxyethylene monolaurate (Emanon 1112, Kao Corporation) and 44 parts of water were added thereto, to produce a uniform flowable agent.

Preparation Example 3

10.6 parts of Compound No. 44 in Table 5, 10 parts of ethylene glycol, 0.1 part of butyl parabene, 0.2 part of silicone emulsion (Antifoam E20, Kao Corporation), 0.8 part of colloidal water-containing aluminum silicate (Kunipia F, Kunimine Kogyo Co., Ltd.), 2 parts of polyoxyalkylene allyl phenyl ether sulfate (Neugen EA-177, Dai-ichi Kogyo Seiyaku Co., Ltd.), 2 parts of polyoxyalkylene distyryl phenyl ether (New Cargen FS-7, Takemoto Oil & Fat Co., Ltd.), 1 part of rosin glycerin ester (Solpoal 7518, Toho Chemical. Industry Co., Ltd.) and 73.3 parts of water were mixed and milled in a wet system by Dynomill KDL (Sinmal Enterprise), to produce a uniform suspension (flowable agent).

Preparation Example 4

1.1 parts of Compound No. 38 in Table 5, 30 parts of bentonite (Kunigel V2, Kunimine Kogyo Co., Ltd.), 66.4 parts of calcium carbonate (Tancal O-430, Asahi Komatsu Co., Ltd.), 2 parts of sodium polyacrylate (Toxanone GR-31A, Sanyo Chemical Industries, Ltd.) and 0.5 part of sodium dioctylsulfosuccinate (Sanmoline OT, Sanyo Chemical Industries, Ltd.) were mixed, and water was added thereto, and the mixture was kneaded. Thereafter, this kneaded product was extruded and granulated through a Φ1.2 mm screen and dried at 60° C. to give granules having a particle diameter of 0.5 to 1.7 mm.

Test Example 1

A 5 cm×5 cm Jiffy Pot™ was charged with paddy soil, then water was introduced into each pot, seeds of sulfonylurea herbicide-sensitive *Scirpus juncoides* var. *ohwianus*, sulfonylurea herbicide-sensitive *Lindernia procumbens* (Krock.) Philcox, sulfonylurea herbicide-sensitive *Lindernia dubia* subsp. *major* Pennell, sulfonylurea herbicide-resistant *Scirpus juncoides* var. *ohwianus*, sulfonylurea herbicide-resistant *Lindernia procumbens* (Krock.) Philcox and sulfonylurea herbicide-resistant *Lindernia dubia* subsp. *major* Pennell were sowed therein and cultivated for a prescribed period under flooding conditions. When the plants reached the two-leave stage, the prescribed number of Jiffy Pots where the plants had been grown were transferred to a 150-cm² rectangular plastic pot, and water was introduced to a height of 3 cm, and a chemical diluent containing a compound was applied into the pot in an amount of 1 g/are. The chemical diluent was prepared by dissolving 1.5 g compound in 2 L of N,N-dimethylformamide (DMF) containing 2% (W/V) surfactant Tween™ 20 and then diluting it with water to adjust the total volume to 10 L.

Three weeks after treatment with the chemical, the effect on each weed was evaluated under the criteria shown in Table 6.

TABLE 6

| Index | Effect | Degree of suppression (weeding ratio) % |
|---|---|---|
| 0 | none | 0 |
| 1 | very slight | 1 to 20 |
| 2 | slight | 21 to 40 |
| 3 | moderate | 41 to 60 |
| 4 | high | 61 to 80 |
| 5 | excellent | 81 to 100 |

The results are shown in Tables 7 and 8.

TABLE 7

| Compound No. | S *Scirpus juncoides* var. *ohwianus* | S *Lindernia procumbens* (Krock.) Philcox | S *Lindernia dubia* subsp. *major* Pennell | R *Scirpus juncoides* var. *ohwianus* | R *Lindernia procumbens* (Krock.) Philcox | R *Lindernia dubia* subsp. *major* Pennell |
|---|---|---|---|---|---|---|
| 3 | 5 | 5 | 5 | 5 | 5 | 5 |
| 4 | 5 | 5 | 5 | 5 | 3 | 5 |
| 7 | 5 | 5 | 5 | 5 | 3 | 4 |
| 8 | 5 | 5 | 5 | 5 | 5 | 5 |
| 9 | 5 | 5 | 5 | 5 | 3 | 5 |
| 11 | 5 | 5 | 5 | 5 | 5 | 5 |
| 12 | 5 | 5 | 5 | 5 | 3 | 5 |
| 13 | 5 | 5 | 5 | 5 | 5 | 5 |
| 14 | 5 | 5 | 5 | 5 | 3 | 4 |
| 16 | 5 | 5 | 5 | 5 | 4 | 5 |

TABLE 7-continued

| Compound No. | S Scirpus juncoides var. ohwianus | S Lindernia procumbens (Krock.) Philcox | S Lindernia dubia subsp. major Pennell | R Scirpus juncoides var. ohwianus | R Lindernia procumbens (Krock.) Philcox | R Lindernia dubia subsp. major Pennell |
|---|---|---|---|---|---|---|
| 18 | 5 | 5 | 5 | 5 | 5 | 5 |
| 19 | 5 | 5 | 5 | 5 | 5 | 4 |
| 23 | 5 | 5 | 5 | 5 |   | 4 |
| 25 | 5 | 5 | 5 | 5 |   | 4 |
| 26 | 5 | 5 | 5 | 5 | 3 | 4 |
| 31 | 5 | 5 | 5 | 5 |   | 4 |
| 34 | 4 | 5 |   | 4 |   | 5 |
| 35 | 5 | 5 | 5 | 5 | 3 | 5 |
| comparison 1 | 5 | 5 | 5 | 2 | 0 | 1 |
| comparison 2 | 5 | 5 | 5 | 0 | 0 | 0 |

TABLE 8

| Compound No. | S Scirpus juncoides var. ohwianus | S Lindernia procumbens (Krock.) Philcox | S Lindernia dubia subsp. major Pennell | R Scirpus juncoides var. ohwianus | R Lindernia procumbens (Krock.) Philcox | R Lindernia dubia subsp. major Pennell |
|---|---|---|---|---|---|---|
| 36 | 5 | 5 | 5 | 5 | 5 | 5 |
| 37 | 5 | 5 | 5 | 5 | 5 | 5 |
| 38 | 5 | 5 | 5 | 5 | 5 | 5 |
| 39 | 5 | 5 | 5 | 5 | 5 | 5 |
| 40 | 5 | 5 | 5 | 5 | 5 | 5 |
| 41 | 5 | 5 | 5 | 5 | 4 | 5 |
| 43 | 5 | 5 | 5 | 4 |   | 5 |
| 44 | 5 | 5 | 5 | 4 |   | 5 |
| 45 | 5 | 5 | 5 | 4 |   | 5 |
| 46 | 5 | 5 | 5 | 5 |   | 5 |

S: sulfonylurea herbicide-sensitive; Scirpus juncoides var. ohwianus and Lindernia procumbens (Krock.) Philcox were produced in Kyoto Pref.; and Lindernia dubia subsp. major Pennell was produced in Makabe Town in Ibaraki Pref.
R: sulfonylurea herbicide-resistant; Scirpus juncoides var. ohwianus was produced in Iwamisawa City in Hokkaido; Lindernia procumbens (Krock.) Philcox was produced in Tajiri Town in Miyagi Pref.; and Lindernia dubia subsp. major Pennell was produced in Kawanishi Town in Yamagata Pref.

INDUSTRIAL APPLICABILITY

The herbicide of the present invention is useful for control of weeds including sulfonylurea herbicide-resistant weeds in paddy fields, and is also useful for reducing the number of active ingredients in a combined preparation.

The invention claimed is:

1. A compound represented by the formula:

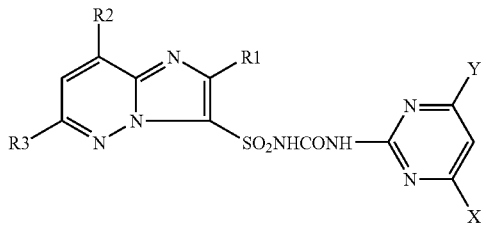

wherein R1 is a chlorine atom, R2 is a hydrogen atom, R3 is an ethyl group, and each of X and Y is a methoxy group, or a salt thereof.

2. A compound represented by the formula:

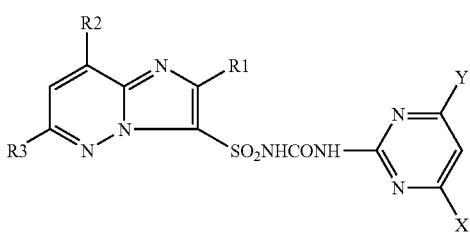

wherein R1 is a methyl group, R2 is a hydrogen atom, R3 is an ethyl group, and each of X and Y is a methoxy group, or a salt thereof.

* * * * *